United States Patent
Nguyen et al.

(10) Patent No.: US 9,127,325 B2
(45) Date of Patent: *Sep. 8, 2015

(54) METHOD AND APPARATUS FOR TREATING A CELLULOSIC FEEDSTOCK

(75) Inventors: Quang A. Nguyen, Chesterfield, MO (US); Murray J. Burke, Oakville (CA); Sunalie N. Hillier, Georgetown (CA)

(73) Assignee: Abengoa Bioenergy New Technologies, LLC., Chesterfield, MO (US)

( * ) Notice: Subject to any disclaimer, the term of this patent is extended or adjusted under 35 U.S.C. 154(b) by 627 days.

This patent is subject to a terminal disclaimer.

(21) Appl. No.: 13/014,327

(22) Filed: Jan. 26, 2011
(Under 37 CFR 1.47)

(65) Prior Publication Data
US 2012/0111321 A1    May 10, 2012

Related U.S. Application Data

(63) Continuation-in-part of application No. 12/181,565, filed on Jul. 29, 2008, and a continuation-in-part of
(Continued)

(30) Foreign Application Priority Data

| Jul. 24, 2008 | (CA) | 2638150 |
| Jul. 24, 2008 | (CA) | 2638152 |
| Jul. 24, 2008 | (CA) | 2638157 |
| Jul. 24, 2008 | (CA) | 2638159 |
| Jul. 24, 2008 | (CA) | 2638160 |
| Jan. 23, 2009 | (CA) | 2650913 |
| Jan. 23, 2009 | (CA) | 2650919 |

(51) Int. Cl.
*C13K 1/02* (2006.01)
*C12M 1/00* (2006.01)
(Continued)

(52) U.S. Cl.
CPC ............ *C13K 1/02* (2013.01); *C12M 45/06* (2013.01); *C12M 45/20* (2013.01); *C12P 7/10* (2013.01); *C12P 19/02* (2013.01); *C12P 2201/00* (2013.01); *Y02E 50/16* (2013.01)

(58) Field of Classification Search
CPC ........ C13K 1/02; C12M 45/06; C12M 45/20; C12P 7/10; C12P 19/02; C12P 2201/00; Y02E 50/16

USPC ........... 127/37, 1; 536/124; 366/169.1, 170.3, 366/172.1, 297
See application file for complete search history.

(56) References Cited

U.S. PATENT DOCUMENTS

| 319,299 A | 6/1885 | Morgan |
| 459,113 A | 9/1891 | Rymal |

(Continued)

FOREIGN PATENT DOCUMENTS

| CA | 1070537 | 1/1980 |
| CA | 1096374 B | 2/1981 |

(Continued)

OTHER PUBLICATIONS

International Search Report and the Written Opinion issued in PCT Application No. PCT/US2012/022552, dated May 15, 2012, 18 pages.

(Continued)

*Primary Examiner* — David C Mellon
(74) *Attorney, Agent, or Firm* — Armstrong Teasdale LLP

(57) ABSTRACT

Methods and apparatus for treating, pre-treating, preparing and conveying a cellulosic feedstock, such as for ethanol production, are disclosed. More specifically, the invention relates to methods and apparatus for treating a cellulosic feedstock by mixing and heating the cellulosic feedstock and/or by moistening and heating the cellulosic feedstock. The invention also relates to a holding tank, and a method of utilizing the holding tank whereby bridging may be reduced or eliminated and may result in a product stream from auto-hydrolysis or hydrolysis having an improved yield. The invention further relates to methods and apparatus for obtaining and conveying a cellulosic feedstock, which may be used for the subsequent production of a fermentable sugar stream from the cellulose and hemicellulose in the cellulosic feedstock wherein the fermentable sugar stream may be used for subsequent ethanol production. The invention also relates to a method and apparatus for withdrawing one or more feedstock stream from a holding tank.

40 Claims, 34 Drawing Sheets

Related U.S. Application Data application No. 12/181,596, filed on Jul. 29, 2008, and a continuation-in-part of application No. 12/181,640, filed on Jul. 29, 2008, and a continuation-in-part of application No. 12/181,666, filed on Jul. 29, 2008, now Pat. No. 8,449,680, and a continuation-in-part of application No. 12/181,724, filed on Jul. 29, 2008, and a continuation-in-part of application No. 12/361,103, filed on Jan. 28, 2009, and a continuation-in-part of application No. 12/361,149, filed on Jan. 28, 2009.

(51) Int. Cl.
*C12P 7/10* (2006.01)
*C12P 19/02* (2006.01)

(56) References Cited

U.S. PATENT DOCUMENTS

| | | |
|---|---|---|
| 1,073,425 A | 9/1913 | Lamert |
| 1,106,736 A | 8/1914 | Schuler |
| 1,173,825 A | 2/1916 | McWallen |
| 1,190,923 A | 7/1916 | Lindquist |
| 1,247,153 A | 11/1917 | Roberts |
| 1,560,855 A | 11/1925 | Queneau |
| 1,824,221 A | 9/1931 | Mason |
| 2,080,327 A | 5/1937 | McKinnis |
| 2,086,701 A | 7/1937 | Dreyfus |
| 2,263,608 A | 11/1941 | Brown |
| 2,333,739 A | 11/1943 | Puckett |
| 2,541,058 A | 2/1951 | Heritage et al. |
| 2,541,059 A | 2/1951 | Heritage et al. |
| 2,541,127 A | 2/1951 | Van Beckum |
| 2,570,042 A | 10/1951 | West |
| 2,595,827 A | 5/1952 | Boruff et al. |
| 2,615,883 A | 10/1952 | Sweeney et al. |
| 2,697,703 A | 12/1954 | Heritage et al. |
| 2,758,031 A | 8/1956 | Ozai-Durrani |
| 3,017,404 A | 1/1962 | Ball |
| 3,109,560 A | 11/1963 | Rosenleaf |
| 3,199,731 A | 8/1965 | Brauer et al. |
| 3,223,697 A | 12/1965 | Ball et al. |
| 3,357,437 A | 12/1967 | Maguire |
| 3,383,277 A | 5/1968 | Gordon et al. |
| 3,407,943 A | 10/1968 | Douglass, Jr. |
| 3,572,593 A | 3/1971 | Guarisco |
| 3,617,433 A | 11/1971 | Sutherland |
| 3,640,509 A | 2/1972 | Inamura et al. |
| 3,743,572 A | 7/1973 | Richter et al. |
| 3,817,826 A | 6/1974 | Hoye |
| 3,964,874 A | 6/1976 | Maruko et al. |
| 3,964,880 A | 6/1976 | Siegrist |
| 4,023,982 A | 5/1977 | Knauth |
| 4,055,673 A | 10/1977 | Mueller et al. |
| 4,062,304 A | 12/1977 | Herbold et al. |
| 4,119,025 A | 10/1978 | Brown |
| 4,136,207 A | 1/1979 | Bender |
| 4,160,695 A | 7/1979 | Dietrichs et al. |
| 4,181,796 A | 1/1980 | Dietrichs et al. |
| 4,186,658 A | 2/1980 | Brown |
| 4,196,827 A | 4/1980 | Leafdale |
| 4,200,692 A | 4/1980 | Puls et al. |
| 4,211,163 A | 7/1980 | Brown et al. |
| 4,237,226 A | 12/1980 | Grethlein |
| 4,281,934 A | 8/1981 | Krause et al. |
| 4,286,884 A | 9/1981 | Retrum |
| 4,296,864 A | 10/1981 | Misaka et al. |
| 4,316,748 A | 2/1982 | Rugg et al. |
| 4,331,447 A | 5/1982 | Kamada et al. |
| 4,341,353 A | 7/1982 | Hamilton et al. |
| 4,364,667 A | 12/1982 | Reiner |
| 4,412,485 A | 11/1983 | Brown |
| 4,427,453 A | 1/1984 | Reitter |
| 4,432,805 A | 2/1984 | Nuuttila et al. |
| 4,436,586 A | 3/1984 | Elmore |
| 4,451,567 A | 5/1984 | Ishibashi et al. |
| 4,461,648 A | 7/1984 | Foody |
| 4,470,851 A | 9/1984 | Paszner et al. |
| 4,483,625 A | 11/1984 | Fisher |
| 4,511,433 A | 4/1985 | Tournier et al. |
| 4,584,057 A | 4/1986 | Rowe et al. |
| 4,600,590 A | 7/1986 | Dale |
| 4,615,742 A | 10/1986 | Wright |
| 4,645,541 A | 2/1987 | Delong |
| 4,667,373 A | 5/1987 | Roder |
| 4,670,944 A | 6/1987 | Thrash |
| 4,676,363 A | 6/1987 | Buchmuller et al. |
| 4,746,404 A | 5/1988 | Laakso |
| 4,751,034 A | 6/1988 | Delong et al. |
| 4,752,579 A | 6/1988 | Arena et al. |
| 4,764,596 A | 8/1988 | Lora et al. |
| 4,775,239 A | 10/1988 | Martinek et al. |
| 4,798,651 A | 1/1989 | Kokta |
| 4,822,737 A | 4/1989 | Saida |
| 4,867,846 A | 9/1989 | Fleck |
| 4,869,786 A | 9/1989 | Hanke |
| 4,908,098 A | 3/1990 | Delong et al. |
| 4,908,099 A | 3/1990 | Delong |
| 4,911,558 A | 3/1990 | Teske |
| 4,947,743 A | 8/1990 | Brown et al. |
| 4,966,650 A | 10/1990 | Delong et al. |
| 4,997,488 A | 3/1991 | Gould et al. |
| 5,012,731 A | 5/1991 | Maisonneuve |
| 5,023,097 A | 6/1991 | Tyson |
| 5,034,099 A | 7/1991 | Nilsson |
| 5,047,332 A | 9/1991 | Chahal |
| 5,052,874 A | 10/1991 | Johanson |
| 5,100,066 A | 3/1992 | Frei |
| 5,114,488 A | 5/1992 | Huber et al. |
| 5,122,228 A | 6/1992 | Bouchette et al. |
| 5,135,861 A | 8/1992 | Pavilon |
| 5,176,295 A | 1/1993 | Stefanik |
| 5,181,804 A | 1/1993 | Wysong et al. |
| 5,188,298 A | 2/1993 | Gerber |
| 5,198,074 A | 3/1993 | Villavicencio et al. |
| 5,221,357 A | 6/1993 | Brink |
| 5,338,366 A | 8/1994 | Grace et al. |
| 5,348,871 A | 9/1994 | Scott et al. |
| 5,366,558 A | 11/1994 | Brink |
| 5,411,594 A | 5/1995 | Brelsford |
| 5,417,492 A | 5/1995 | Christian et al. |
| 5,424,417 A | 6/1995 | Torget et al. |
| 5,487,989 A | 1/1996 | Fowler et al. |
| 5,503,996 A | 4/1996 | Torget et al. |
| 5,504,259 A | 4/1996 | Diebold et al. |
| 5,536,325 A | 7/1996 | Brink |
| 5,571,703 A | 11/1996 | Chieffalo et al. |
| 5,597,714 A | 1/1997 | Farone et al. |
| 5,611,930 A | 3/1997 | Nguyen et al. |
| 5,628,830 A | 5/1997 | Brink |
| 5,677,154 A | 10/1997 | Van Draanen et al. |
| 5,705,216 A | 1/1998 | Tyson |
| 5,705,369 A | 1/1998 | Torget et al. |
| 5,730,837 A | 3/1998 | Black et al. |
| 5,733,758 A | 3/1998 | Nguyen |
| 5,735,916 A | 4/1998 | Lucas et al. |
| 5,791,779 A | 8/1998 | Smith, Sr. |
| 5,843,760 A | 12/1998 | Zhang et al. |
| 5,863,389 A | 1/1999 | White et al. |
| 5,916,780 A | 6/1999 | Foody et al. |
| 5,932,452 A | 8/1999 | Mustranta et al. |
| 6,022,419 A | 2/2000 | Torget et al. |
| 6,063,204 A | 5/2000 | Hester et al. |
| 6,090,595 A | 7/2000 | Foody et al. |
| 6,199,299 B1 | 3/2001 | Prough et al. |
| 6,228,177 B1 | 5/2001 | Torget |
| 6,330,767 B1 | 12/2001 | Carr et al. |
| 6,336,573 B1 | 1/2002 | Johanson |
| 6,409,841 B1 | 6/2002 | Lombard |
| 6,419,788 B1 | 7/2002 | Wingerson |
| 6,423,145 B1 | 7/2002 | Nguyen et al. |
| 6,498,029 B2 | 12/2002 | Keller, Jr. et al. |
| 6,557,267 B2 | 5/2003 | Wanger |
| 6,569,653 B1 | 5/2003 | Alard et al. |

(56) References Cited

U.S. PATENT DOCUMENTS

| | | |
|---|---|---|
| 6,572,734 B2 | 6/2003 | Baker |
| 6,620,292 B2 | 9/2003 | Wingerson |
| 6,648,251 B1 | 11/2003 | Chollet |
| 6,660,506 B2 | 12/2003 | Nguyen et al. |
| 6,737,258 B2 | 5/2004 | Hames et al. |
| 6,743,928 B1 | 6/2004 | Zeitsch |
| 6,908,995 B2 | 6/2005 | Blount |
| 6,927,048 B2 | 8/2005 | Verser et al. |
| 7,109,005 B2 | 9/2006 | Eroma et al. |
| 7,178,698 B2 | 2/2007 | Forslund et al. |
| 7,198,925 B2 | 4/2007 | Foody |
| 7,238,242 B2 | 7/2007 | Pinatti et al. |
| 7,396,434 B2 | 7/2008 | Rodriguez Rivera et al. |
| 7,445,691 B2 | 11/2008 | Snekkenes et al. |
| 7,461,591 B2 | 12/2008 | Babbini |
| 7,494,675 B2 | 2/2009 | Abbas et al. |
| 7,503,981 B2 | 3/2009 | Wyman et al. |
| 7,875,444 B2 | 1/2011 | Yang et al. |
| 7,901,511 B2 | 3/2011 | Griffin et al. |
| 7,937,851 B2 | 5/2011 | Rajagopalan et al. |
| 7,993,463 B2 | 8/2011 | Griffin et al. |
| 8,051,986 B2 | 11/2011 | Lees |
| 8,053,566 B2 | 11/2011 | Belanger et al. |
| 8,193,395 B2 | 6/2012 | Fenton et al. |
| 8,449,680 B2 * | 5/2013 | Burke et al. ............... 127/37 |
| 2002/0003032 A1 | 1/2002 | Nay et al. |
| 2002/0164731 A1 | 11/2002 | Eroma et al. |
| 2003/0089465 A1 | 5/2003 | Schaible et al. |
| 2004/0121436 A1 | 6/2004 | Blount |
| 2004/0154760 A1 | 8/2004 | Dean |
| 2004/0171136 A1 | 9/2004 | Holtzapple et al. |
| 2004/0231661 A1 | 11/2004 | Griffin et al. |
| 2004/0231811 A1 | 11/2004 | Engstrand et al. |
| 2005/0269048 A1 | 12/2005 | Rodriguez et al. |
| 2006/0088922 A1 | 4/2006 | Yang et al. |
| 2006/0163118 A1 | 7/2006 | Kelsey et al. |
| 2006/0169430 A1 | 8/2006 | Tarasenko |
| 2006/0188965 A1 | 8/2006 | Wyman et al. |
| 2006/0233864 A1 | 10/2006 | Power |
| 2006/0272518 A1 | 12/2006 | Babbini |
| 2006/0275895 A1 | 12/2006 | Jensen et al. |
| 2007/0037267 A1 | 2/2007 | Lewis et al. |
| 2007/0148751 A1 | 6/2007 | Griffin et al. |
| 2007/0209974 A1 | 9/2007 | Lees |
| 2007/0215300 A1 | 9/2007 | Upfal et al. |
| 2007/0218530 A1 | 9/2007 | Duck et al. |
| 2007/0227063 A1 | 10/2007 | Dale et al. |
| 2008/0026431 A1 | 1/2008 | Saito et al. |
| 2008/0038784 A1 | 2/2008 | D'Arnaud-Taylor |
| 2008/0227161 A1 | 9/2008 | Levie et al. |
| 2009/0029432 A1 | 1/2009 | Abbas et al. |
| 2009/0062516 A1 | 3/2009 | Belanger et al. |
| 2009/0069550 A1 | 3/2009 | Belanger et al. |
| 2009/0098616 A1 | 4/2009 | Burke et al. |
| 2009/0098617 A1 | 4/2009 | Burke et al. |
| 2009/0240088 A1 | 9/2009 | Fenton et al. |
| 2009/0246848 A1 | 10/2009 | Noel |
| 2010/0024806 A1 | 2/2010 | Burke et al. |
| 2010/0024807 A1 | 2/2010 | Burke et al. |
| 2010/0024808 A1 | 2/2010 | Burke et al. |
| 2010/0024809 A1 | 2/2010 | Burke et al. |
| 2010/0028089 A1 | 2/2010 | Burke et al. |
| 2010/0041119 A1* | 2/2010 | Christensen et al. ......... 435/162 |
| 2010/0124583 A1 | 5/2010 | Medoff |
| 2010/0186735 A1 | 7/2010 | Burke et al. |
| 2010/0186736 A1 | 7/2010 | Burke et al. |
| 2011/0011391 A1 | 1/2011 | Burke |
| 2012/0111321 A1 | 5/2012 | Nguyen et al. |

FOREIGN PATENT DOCUMENTS

| | | |
|---|---|---|
| CA | 1147105 A | 5/1983 |
| CA | 1173825 A | 9/1984 |
| CA | 1190923 A | 7/1985 |
| CA | 1267407 B | 4/1990 |
| CA | 1287705 C | 8/1991 |
| CA | 2037275 A1 | 8/1992 |
| CA | 1322366 C | 9/1993 |
| CA | 2063547 A1 | 9/1993 |
| CA | 2065939 A1 | 10/1993 |
| CA | 2339002 A1 | 2/2000 |
| CA | 2638150 A1 | 1/2010 |
| CA | 2638159 A1 | 1/2010 |
| CN | 200981760 | 11/2007 |
| EP | 0487793 A1 | 6/1992 |
| EP | 0884391 B1 | 1/2002 |
| EP | 1316620 A2 | 6/2003 |
| EP | 1036236 B1 | 7/2003 |
| FR | 777824 | 3/1935 |
| GB | 892506 | 3/1962 |
| GB | 1043460 A | 9/1966 |
| WO | 9213849 A1 | 8/1992 |
| WO | 9640970 A1 | 12/1996 |
| WO | 9732073 A1 | 9/1997 |
| WO | 0238787 A2 | 5/2002 |
| WO | 2004018645 A2 | 3/2004 |
| WO | 2004081193 A2 | 9/2004 |
| WO | 2004106624 A1 | 12/2004 |
| WO | 2005079190 A2 | 9/2005 |
| WO | 2005118165 A1 | 12/2005 |
| WO | 2006017655 A3 | 2/2006 |
| WO | 2006034591 A1 | 4/2006 |
| WO | 2006055362 A1 | 5/2006 |
| WO | 2006063467 A1 | 6/2006 |
| WO | 2007009463 A2 | 1/2007 |
| WO | 2007064296 A1 | 6/2007 |
| WO | 2007065241 A1 | 6/2007 |
| WO | 2007111605 A1 | 10/2007 |
| WO | 2008086115 A2 | 7/2008 |
| WO | 2008144903 A1 | 12/2008 |
| WO | 2009012779 A2 | 1/2009 |
| WO | 2009018469 A1 | 2/2009 |
| WO | 2009089439 A1 | 7/2009 |
| WO | 2010006840 A2 | 1/2010 |
| WO | 2010009547 A1 | 1/2010 |
| WO | 2010009548 A1 | 1/2010 |
| WO | 2010009549 A1 | 1/2010 |
| WO | 2010009550 A1 | 1/2010 |
| WO | 2010009551 A1 | 1/2010 |
| WO | 2010083600 A1 | 7/2010 |
| WO | 2010083601 A1 | 7/2010 |
| WO | 2011028554 A1 | 3/2011 |

OTHER PUBLICATIONS

International Search Report and the Written Opinion issued in PCT Application No. PCT/CA2009/001034, dated Oct. 20, 2009, 9 pages.

Taherzadeh, M. J. et al., "Pretreatment of Lignocellulosic Wastes to Improve Ethanol and Biogas Production: A Review," 2008, Int. J. Mol. Sci., (9) 1621-1651.

Bakker, R. R., et al., "Biofuel Production from Acid-Impregnated Willow and Switchgrass," 2nd World Conference on Biomass for Energy, Industry and Climate Protection, May 10-14, 2004, Rome, Italy, pp. 1467-1470.

*Abengoa Bioenergy New Technologies Inc. f/k/a Abengoa Bioenergy R&D, Inc. v. Mascoma Corporation*; Notice of Arbitration and Statement of Claim, submitted to American Arbitration Association Commercial Arbitration Tribunal on Nov. 2, 2011, pp. 1-14.

International Search Report issued in connection with PCT Application No. PCT/CA2010/000088, mailed as a corrected version on Jun. 17, 2010.

International Search Report and the Written Opinion issued in connection with international application No. PCT/CA2009/001033, mailed on Oct. 30, 2009.

International Search Report and the Written Opinion issued in connection with international application No. PCT/CA2009/001032, dated Oct. 27, 2009.

International Preliminary Report of Patentability issued in connection with International Application No. PCT/CA2009/001034, issued on Jan. 25, 2011.

(56) References Cited

OTHER PUBLICATIONS

Written Opinion of the International Searching Authority, dated Oct. 8, 2010, corresponding to International application No. PCT/CA2010/001091.
PCT International Search Report, dated Oct. 8, 2010, corresponding to International application No. PCT/CA2010/001091.
The Artisan Dualflo Tray, Product Brochure, Artisan Industries, Inc., Bulletin 9801, Edit Date 041703, 2 pages.
Fuel Ethanol Application Sheet, "CELLIC Ctec and Htec2—Enzymes for Hydrolysis of Lignocellulosic Materials," Novozymes A/S, Luna No. 2010-01668-01, 9 pages.
Flexitray Valve Trays, Product Brochure, Koch-Glitsch, Bulletin FTCVT-01, Revised Mar. 2010, 12 pages.
GEA Wiegand, GmbH, Process Engineering Division, "Bioethanol Technology", Ettlingen, Germany, Company Brochure, 16 pages.
GEA Wiegand, GmbH, Process Engineering Division, "Distillation Technology", Ettlingen, Germany, Company Brochure, 16 pages.
Propax Yeast Propagation Technology, Product Brochure, Meura S.A., Edited 2009, 2 pages.
Silwet L-77 Surfactant, Specimen Label, Helena Chemical Company, Copyright 2006, 2 pages.
Superfrac High Performance Trays, Product Brochure, Koch-Glitsch, Bulletin KGSF-1, Revised Mar. 2010, 16 pages.
"Biofuels Pilot Plant Under Way," Newsbriefs, Chemical Week, October 13/20, 2008, p. 4.
"Lessons Learned from Existing Biomass Power Plants," Feb. 2000, NREL/SR-570-26946, G. Wiltsee, Appel Consultants, Inc., Valencia, CA, 149 pages.
"Types of Lignin and Their Properties," 2001, Information Service from the Lignin Institute, 9/1:4 pages, www.lignin.org/01augdialogue.html.
"Enzyme Sugar-Ethanol Platform Project," NREL, U.S. Dept. of Energy by Midwest Research Institute, Battelle, Bechtel, 47 pages.
"Easy Steps for Optimal Yeast Rehydration," Laboratory Protocol, Scott Laboratories, Petaluma CA, 1 page.
Liu, H., et al., "Lignin-Metal Complexation to Eliminate Nonproductive Enzyme Adsorption by Lignin in Unwashed Lignocellulosic Substrates," 2010, 32nd Symposium on Biotechnology for Fuels and Chemicals, 28 pages.
Thomas, S.R., "Corn Stover Feedstock Variability," 2005, Feedstock Area Stage Gate Review Meeting, 34 pages.
Weiss, N.D., et al., "Catalyst Impregnation for High Solids Biomass Pretreatment," 2008, AIChE Annual Meeting, 24 pages.
Zimbardi, F., et al., "Acid Impregnation and Steam Explosion of Corn Stover in Batch Processes," 2007, Ind Crops and Products, 26:195-206.
"Process Design and Cost Estimate of Critical Equipment in the Biomass to Ethanol Process, Report 99-10600/17 Continuous Acid Hydrolysis Reactor," Jan. 22, 2011 Rev WEB, Subcontract ACO-9-29067-01, National Renewable Energy Laboratory, Golden, CO, Harris Group Inc., Seattle, WA, 14 pages.
"Transactions of the Institution of Chemical Engineers," 1993, 11 Institution of Chemical Engineers, London, the United Kingdom.
"Handbook of Pulp and Paper Technology," 1996, 2nd. edition., Kenneth W.Britt, ed., (New York: Van Nostrand Reinhold Company).
"Paper and Composites from Agro-Based Resources," 1996, Rowell, Young & Rowell, Eds., (Lewis Publishers).
Abstract of Chinese Patent Application CN 101310879 A, 2008, Institute of Process Engineering, Chinese Academy of Sciences.
Aden, A., et al., "Lignocellulosic Biomass to Ethanol Process Design and Economics Utilizing Co-Current Dilute Acid Prehydrolysis and Enzymatic Hydrolysis for Corn Stover," 2002, Technical Report published by National Renewable Energy Laboratory, 154 pages.
Al-Halaly, A.S.M., "A Study of Some Anatomical Chemical Properties and Specific Gravity of *Casuarina equisetifolia* Forst. Wood Grown in Iraq," 1985, AGRIS Record No. IQ8500239, Abstract, 1 page.
Antongiovanni, M., et al., "Variability in Chemical Composition of Straws," 1991, CIHEAM—Options Mediterraneennes, Serie Seminaires, 16:49-53.

Awafo, V.A., et al., "Evaluation of Combination Treatments of Sodium Hydroxide and Steam Explosion for the Production of Cellulase-Systems by Two *T. reesei* Mutants Under Solid-State Fermentation Conditions," 2000, Bioresource Tech, 73:235-245.
Azadbakht, M., et al., "Preparation of Lignin From Wood Dust as Vanillin Source and Comparison of Different Extraction Methods," Oct. 2004, Int J of Biol and Biotech, 1/4:535-537, Abstract Only, 1 page.
Ballerini, D., et al., "Ethanol Production from Lignocellulosics: Large Scale Experimentation and Economics," 1994, Bioresource Tech, 50:17-23.
Bigelow, M., et al., "Cellulase Production on Bagasse Pretreated with Hot Water," 2002, App Biochem and Biotech, 98-100:921-934.
Brownell, H.H., et al., "Steam-Explosion Pretreatment of Wood: Effect of Chip Size, Acid, Moisture Content and Pressure Drop," 1986, Biotechnol Bioeng, 28/6:792-801, Abstract Only, 1 page.
Coons, R., "DSM Launches Cellulosic Biofuel Project," Oct. 27, 2008, Chemical Week, 170/33:9.
Coons, R., "Novozymes Ramps Up Focus on Second-Generation Biofuels," Oct. 27, 2008, Chemical Week, 170/33:30.
Cullis, I.F., et al., "Effect of Initial Moisture Content and Chip Size on the Bioconversion Efficiency of Softwood Lignocellulosics," 2004, Biotechnol Bioeng, 85/4:413-421, Abstract Only, 1 page.
Cunningham, R.L., et al., "Improved Hemicellulose Recovery From Wheat Straw," 1985, Biotech and Bioeng Symp No. 15, Seventh Symposium on Biotechnology for Fuels and Chemicals, pp. 17-26.
Dasari, R.K., et al., "The Effect of Particle Size on Hydrolysis Reaction Rates and Rheological Properties in Cellulosic Slurries," 2007, Appl Biochem and Biotech, Session 2, 137-140/1-2, 289-299, Abstract Only.
Dowe, N., et al., "SSF Experimental Protocols-Lignocellulosic Biomass Hydrolysis and Fermentation, Laboratory Analytical Procedure (LAP)," Jan. 2008, NREL Technical Report, NREL/TP-510-42630, 19 pages.
Duff, S.J.B., et al., "Bioconversion of Forest Products Industry Waste Cellulosics to Fuel Ethanol: A Review", 1996, Bioresource Technology, 55:1-33.
Eggeman, T., et al., "Process and Economics Analysis of Pretreatment Technologies," 2005, Bioresource Technology, 96:2019-2025.
Emert, G.H., et al., "Gasohol/Biomass Developments: Economic Update of the Gulf Cellulose Alcohol Process," 1980, Chemical Engineering Progress, 76/9:47-52.
Flint, S.I., et al., "Recovery of Lignin During Nonstarch Polysaccharide Analysis," 1992, Cereal Chem, 69/4:444-447.
Foody, P., "Optimization of Steam Explosion Pretreatment," 1980, Final Report to DOE, Report No. DOE/ET23050-1, Contract No. AC02-79ET23050, Bibliographic Citation, 1 page.
Hames, B., et al., "Determination of Protein Content in Biomass, Laboratory Analytical Procedure (LAP)," May 2008, NREL Technical Report, NREL/TP-510-42625, 8 pages.
Hames, B., et al., "Preparation of Samples for Compositional Analysis, Laboratory Analytical Procedure (LAP)," Aug. 2008, NREL Technical Report, NREL/TP-510-42620, 12 pages.
Juhasz, T., et al., "Characterization of Cellulases and Hemicellulases Produced by *Trichoderma reesei* on Various Carbon Sources," 2005, Process Biochem, 40:3519-3525.
Katzen, R., et al., "Wood Hydrolysis. A Continuous Process," 1942, Industrial and Engineering Chemistry 34/3:314-322.
Kazi, K.M.F., et al., "Preimpregnation: An Important Step for Biomass Refining Processes," 1998, Biomass and Bioenergy, 15/2:125-141.
Keller, F.A., et al., "Yeast Adaptation on Softwood Prehydrolysate," 1998, Appl Biochem and Biotech, 70-72:137-148.
Kim, K.H., et al., "Continuous Countercurrent Extraction of Hemicellulose from Pretreated Wood Residues," 2001, Appl Biochem and Biotech, 91-93:253-267.
Kim, S.B., et al., "Diffusion of Sulfuric Acid within Lignocellulosic Biomass Particles and Its Impact on Dilute-Acid Pretreatment," 2002, Bioresource Technology 83:165-171.
Knappert, D., et al., "Partial Acid Hydrolysis of Cellulosic Materials as a Pretreatment for Enzymatic Hydrolysis," 1980, Biotech and Bioeng, 22:1449-1463.

(56) References Cited

OTHER PUBLICATIONS

Kolar, L., et al., "Agrochemical Value of Organic Matter of Fermenter Wastes in Biogas Production," 2008, Plant Soil Environ, 54/8:321-328.

Kotrba, R., "The Project of a Lifetime," Feb. 2006, Ethanol Producer Magazine, as republished in Biomassmagazine.com, 3 pages.

Kumar, R., et al., "The Impact of Dilute Sulfuric Acid on the Selectivity of Xylooligomer Depolymerization to Monomers," 2008, Carbohydrate Res, 343:290-300.

Linde, M., et al., "Steam Pretreatment of Acid-Sprayed and Acid-Soaked Barley Straw for Production of Ethanol," 2006, Appl Biochem and Biotech, 129-132:546-562.

Mosier, N., et al., "Features of Promising Technologies for Pretreatment of Lignocellulosic Biomass," 2005, Bioresource Technology, 96:673-686.

Nguyen, Q.A., et al., "NREL/DOE Ethanol Pilot-Plant: Current Status and Capabilities," 1996, Bioresource Technology, 58:189-196.

Nguyen, Q.A., et al., "Dilute Acid Pretreatment of Softwoods," 1998, Appl Biochem and Biotech, 70-72:77-87.

Nguyen, Q.A., et al., "Dilute Acid Hydrolysis of Softwoods", 1999, Appl Biochem and Biotech 77-79:133-142.

Nguyen, Q.A., et al., "Two-Stage Dilute-Acid Pretreatment of Softwoods," 2000, Appl Biochem and Biotech, 84-86:561-576.

Ohgren, K., et al., "High Temperature Enzymatic Prehydrolysis Prior to Simultaneous Saccharification and Fermentation of Steam Pretreated Corn Stover for Ethanol Production," 2007, Enzyme Microb Technol, 40/4:607-613.

Overend, R.P., et al., "Fractionation of Lignocellulosics by Steam-Aqueous Pretreatments," 1987, Phil Trans R Soc Lond A, 321:523-536.

Pan, X., et al., "Bioconversion of Hybrid Poplar to Ethanol and Co-Products Using an Organosolv Fractionation Process: Optimization of Process Yields," 2006, Biotech and Bioeng, 94/5:851-861.

Ramsay, J.A., et al., "Biological Conversion of Hemicellulose to Propionic Acid," 1998, Enzyme Microb Technol, 22:292-295.

Schell, D.J., et al., "Dilute-Sulfuric Acid Pretreatment of Corn Stover in Pilot-Scale Reactor," 2003, Appl Biochem and Biotech, 105-108:69-85.

Schell, D.J., et al., "A Bioethanol Process Development Unit: Initial Operating Experiences and Results with a Corn Fiber Feedstock," 2004, Bioresource Technology, 91:179-188.

Sharma-Shivappa, R.R., et al, "Conversion of Cotton Wastes to Bioenergy and Value-Added Products," 2008, Transactions of the ASABE, 51/6:2239-2246.

Sluiter, A., et al., "Determination of Ash in Biomass, Laboratory Analytical Procedure (LAP)," NREL Technical Report, NREL/TP-510-42622, Jan. 2008, 8 pages.

Sluiter, A., et al., "Determination of Extractives in Biomass, Laboratory Analytical Procedure (LAP)," NREL Technical Report, NREL/TP-510-42619, Jan. 2008, 12 pages.

Sluiter, A., et al., "Determination of Sugars, Byproducts, and Degradation Products in Liquid Fraction Process Samples, Laboratory Analytical Procedure (LAP)," NREL Technical Report, NREL/TP-510-42623, Jan. 2008, 14 pages.

Sluiter, A., et al., "Determination of Total Solids in Biomass and Total Dissolved Solids in Liquid Process Samples, Laboratory Analytical Procedure (LAP)," NREL Technical Report, NREL/TP-510-42621, Mar. 2008, 9 pages.

Sluiter, A., et al., "Determination of Structural Carbohydrates and Lignin in Biomass, Laboratory Analytical Procedure (LAP)," NREL Technical Report, NREL/TP-510-42618, Apr. 2008, 16 pages.

Sun, L., "Silicon-Based Materials from Rice Husks and Their Applications," 2001, Ind Eng Chem Res, 40/25:5861-5877, Abstract Only, 1 page.

Thompson, D.N., et al., "Post-Harvest Processing Methods for Reduction of Silica and Alkali Metals in Wheat Straw," 2002, 24th Symposium on Biotechnology for Fuels and Chemicals, Poster #1-30, 21 pages.

Tucker, M.P., et al, "Comparison of Yellow Poplar Pretreatment Between NREL Digester and Sunds Hydrolyzer," 1998, Appl Biochem and Biotech, 70-72:25-35.

Tucker, M.P., et al, "Effects of Temperature and Moisture on Dilute-Acid Steam Explosion Pretreatment of Corn Stover and Cellulase Enzyme Digestibility," 2003, Appl Biochem and Biotech, 105-108:165-177.

Tucker, M.P., et al, "Conversion of Distiller's Grain into Fuel Alcohol and a Higher-Value Animal Feed by Dilute-Acid Pretreament," 2004, Appl Biochem and Biotech, 113-116:1139-1159.

Viamajala, S., et al., "Catalyst Transport in Corn Stover Internodes," 2005, Appl Biochem and Biotech, 129-132:509-527.

Wyman, C.E., et al., "Comparative Sugar Recovery Data from Laboratory Scale Application of Leading Pretreatment Technologies to Corn Stover," 2005, Bioresource Technology, 96:2026-2032.

Wyman, C.E., "Coordinated Development of Leading Biomass Pretreatment Technologies," 2005, Bioresource Technology 96:1959-1966.

Yang, B., et al., "Chapter 6. Unconventional Relationships for Hemicellulose Hydrolysis and Subsequent Cellulose Digestion," 2004, Lignocellulose Biodegradation, ACS Symposium Series 889, American Chemical Society, pp. 100-125.

On-Line Moisture Measurement and Control Manufacturing Industries Worldwide, Product Information, online: Process Sensors Corporation <http://processsensors.com/index.html?gclid=CKT27fXvJOCFREWagodclkUcw>, 2 pages, downloaded Dec. 30, 2011.

Metso Automation, Metso Automation's Newsletter for Neles and Jamesbury products, "Biofuels—a growth market for Metso", (Summer 2008), online: Metso <http://valveproducts.metso.com/metsoautomation/DocDB/catalogs/catalog.taf?pg_parent=397>, 11 pages.

SunOpta Inc., News Release, "SunOpta Announces Sale of Cellulosic Ethanol Facility to China Resources Alcohol Corporation," (Jun. 23, 2006), online: SunOpta Inc. <http://investor.sunopta.com/releasedetail.cfm?ReleaseID=287111>, 2 pages.

Buell Classifier Fisher-Klosterman, Leaflet, "Operation Principles and Efficiency," 2008, 4 pages.

Abengoa Bioenergy, Press Release, "Abengoa Bioenergy Awarded DOE Financial Assistance Agreement" (Feb. 28, 2007), online: Abengoa Bioenergy <http://www.abengoabioenergy.com/corp/web/en/prensa/noticias/historico/2007/20071015_noticias.html>, 1 page.

Abengoa Bioenergy, Press Release, "Abengoa Bioenergy Opens Pilot Plant for the Energy of the Future" (Oct. 15, 2007), online: Abengoa Bioenergy <http://www.abengoabioenergy.com/corp/web/en/prensa/noticias/historico/2007/20071015_noticias.html>, 1 page.

Annual Report Under Section 13 or 15(d) of the Securities Exchange Act of 1934, for Bluefire Ethanol Fuels, Inc., U.S. Securities and Exchange Commission, Feb. 2008, 102 pages.

Annual Report Under Section 13 or (15)d of the Securities Exchange Act of 1934, for CleanTech Biofuels, Inc., U.S. Securities and Exchange Commission, Mar. 28, 2008, 78 pages.

"Building a Bridge to the Corn Ethanol Industry. Corn Stover to Ethanol at High Plains Corporation's York, Nebraska Co-Located Plant Site", Merrick & Company, Final Report of Jan. 2000, 17 pages.

"Clean Cities: Ethanol Basics" (Oct. 2008), NREL, U.S. Department of Energy, <http://www.afdc.energy.gov/afdc/pdfs/43835.pdf>, 6 pages.

"Fuel Ethanol: Background and Public Policy Issues", (Mar. 3, 2006), CRS Report for Congress, Yacobucci, B.D., online: U.S. Department of State, Foreign Press Centre <http://fpc.state.gov/documents/organization/62837.pdf>, 26 pages.

Kitani, O., et al., "Biomass Handbook," 1989, pp. 470-474 (Gordon and Breach Science Publishers: New York).

Wooley, R., et al., "Lignocellulosic Biomass to Ethanol Process Design and Economics Utilizing Co-Current Dilute Acid Prehydrolysis and Enzymatic Hydrolysis Current and Futuristic Scenarios," 1999, NREL Technical Report, TP-580-26157, 132 pages.

Moiser, N.S.,"Cellulosic Ethanol—Biofuel Beyond Corn," 2006, Bio Energy, ID-335, Purdue University, 4 pages.

(56) References Cited

OTHER PUBLICATIONS

Overend, R.P., "The Lignocellulosic Bottleneck: Material Properties, Architecture and Pretreatment", Slideshow, 25 pages.

Roberts, A.W., "Design Considerations and Performance Evaluation of Screw Conveyors", online: The South African Institute of Materials Handling <http://www.saimh.co.za/beltcon/beltcon11/beltcon1114.htm>, 11 pages.

"Ethanol Annual Report FY 1990", SERI, TP-231/3996, Prepared for the U.S. DOE, Jan. 1991, Contract No. DE-AC02-83CH10093, Texeira, R.H. and Goodman, B.J., editors, 344 pages.

"Ethanol Market Penetration," U.S. Department of Energy, Energy Efficiency & Renewable Energy, Alternative Fuels & Advanced Vehicles Data Center, online: U.S. Department of Energy <http://www.afdc.energy.gov/afdc/ethanol/market.html>, 2 pages.

Outputs from the EPOBIO Workshop, Greece, "Products from Plants—From Crops and Forests to Zero Waste Biorefineries", May 15-17, 2007, 49 pages.

"Process Design and Cost Estimate of Critical Equipment in the Biomass to Ethanol Process," Subcontract ACO-9-29067-01, Acid Hydrolysis Reactors Batch System, Report 99-10600/18, NREL, (Prepared by Harris Group Inc., Seattle, Washington, 2001), 36 pages.

"Research Advances: NREL Leads the Way", 2007, Cellulosic Ethanol, Brochure, NREL/BR-510-40742, Mar. 2007, online: National Renewable Energy Laboratory, <http://www.nrel.gov/biomass/pdfs/40742.pdf>, 8 pages.

"Softwood Biomass to Ethanol Feasibility Study, Final Report: Jun. 14, 1999," NREL/SR-510-27310, Aug. 2004, Subcontractor Report published by National Renewable Energy Laboratory, Merrick & Company, 122 pages.

"Fuel Ethanol Production", U.S. Department of Energy Office of Science, Genomics Science Program, archived website (2009): U.S. Department of Energy Office of Science <http://genomicscience.energy.gov/biofuels/ethanolproduction.shtml>, 6 pages.

International Search Report and the Written Opinion issued in connection with PCT Application No. PCT/CA2009/001035, dated Nov. 5, 2009, 7 pages.

International Search Report and the Written Opinion issued in connection with PCT Application No. PCT/CA2009/001036, dated Nov. 13, 2009, 6 pages.

International Search Report and the Written Opinion issued in connection with PCT Application No. PCT/US2010/46561, dated Dec. 20, 2010, 16 pages.

International Search Report and the Written Opinion issued in connection with PCT Application No. PCT/CA2010/000087, mailed on May 4, 2010, 10 pages.

International Search Report and the Written Opinion issued in connection with PCT Application No. PCT/CA2010/000088, mailed on May 14, 2010, 15 pages.

De Castro, F.B., "The Use of Steam Treatment to Upgrade Lignocellulosic Materials for Animal Feed," 1994, Thesis, University of Aberdeen, 214 pages.

Esteghlalian, A., et al., "Modeling and Optimization of the Dilute-Sulfuric-Acid Pretreatment of Corn Stover, Poplar and Switchgrass," 1997, Bioresource Technology, 59:129-136.

Fan, L.T., et al., "Evaluation of Pretreatments for Enzymatic Conversion of Agricultural Residues," 1981, Biotechnology & Bioengineering Symposium, 11:29-45 (Proceedings of the Third Symposium on Biotechnology in Energy Production and Conservation, Gatlinburg, TN, May 12-15, 1981).

Ghose, T.K., "Measurement of Cellulase Activities," 1987, Pure and Appl. Chem., 59/2:257-268.

Grethlein, H.E., et al., "Common Aspects of Acid Prehydrolysis and Steam Explosion for Pretreating Wood," 1991, Bioresource Technology, 36:77-82.

Grethlein, H.E., "Chemical Breakdown of Cellulosic Materials," 1978, J. Appl. Chem. Biotechnol. 28:296-308.

Grohmann, K., et al., "Optimization of Dilute Acid Pretreatment of Biomass," Proceedings of the Seventh Symposium on Biotechnology for Fuels and Chemicals, May 14-17, 1986, 24 pages.

Nguyen, Q.A., et al., "An Integrated Model for the Technical and Economic Evaluation of an Enzymatic Biomass Conversion Process," 1991, Bioresource Technology, 35:275-282.

Teleman, et al., "Progress-Curve Analysis Shows that Glucose Inhibits the Cellotriose Hydrosysis Catalysed by Cellobiohydrolase II from *Trichoderma reesi*," 1995, European J Biochem, 231:250-258.

Thomas, S., et al., "Biofuels Program C-Milestone Completion Report," FY02, DOE Biofuels Program, Report #373, 2002, 51 pages.

Office action issued in Canadian Application No. 2,638,152, dated Feb. 8, 2011, 4 pages.

International Search Report and the Written Opinion issued in connection with PCT Application No. PCT/CA2009/001032, mailed on Oct. 27, 2009, 11 pages.

Activator 90, Product Brochure, 2009, Loveland Products Inc., No. 6566_05/09, 1 page.

Amistco Tower Trays, Product Brochure, Amistco Separation Products, Inc., 8 pages.

\* cited by examiner

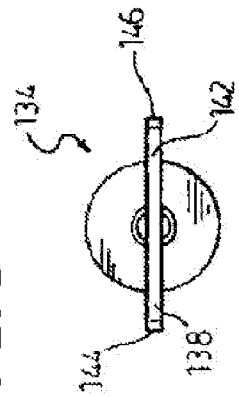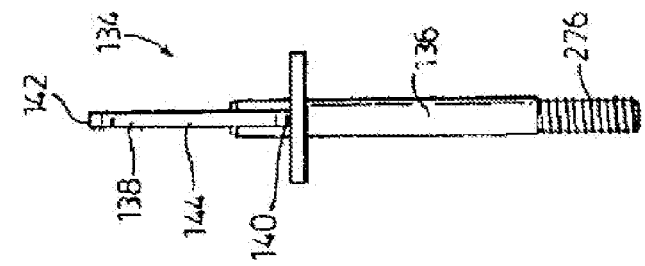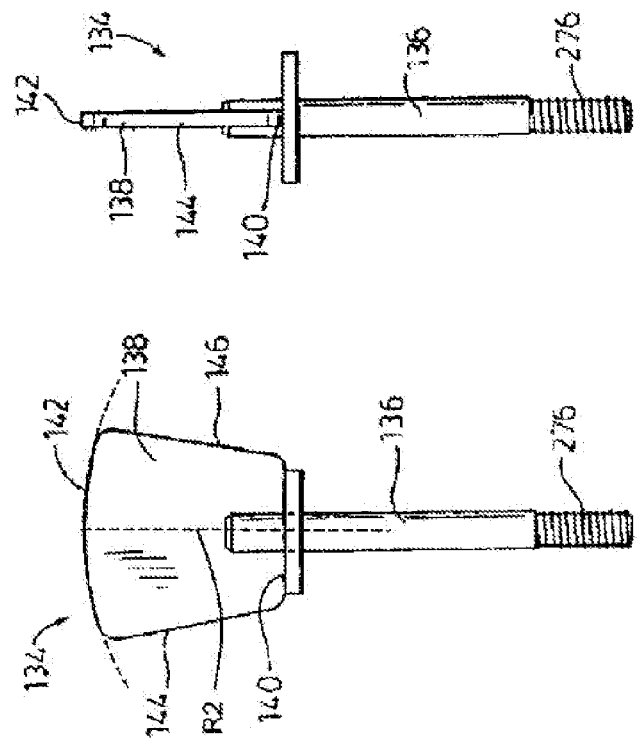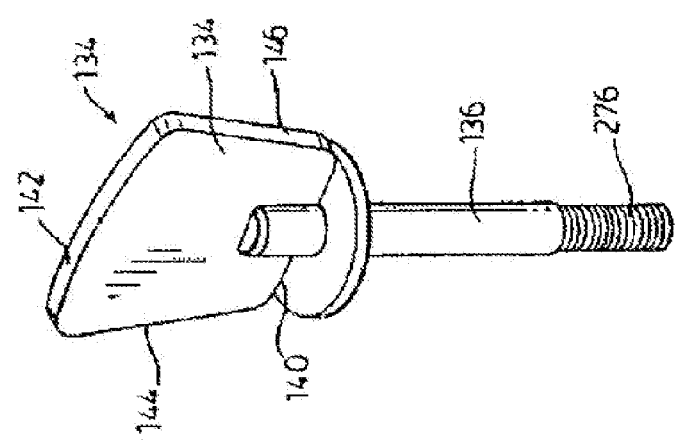

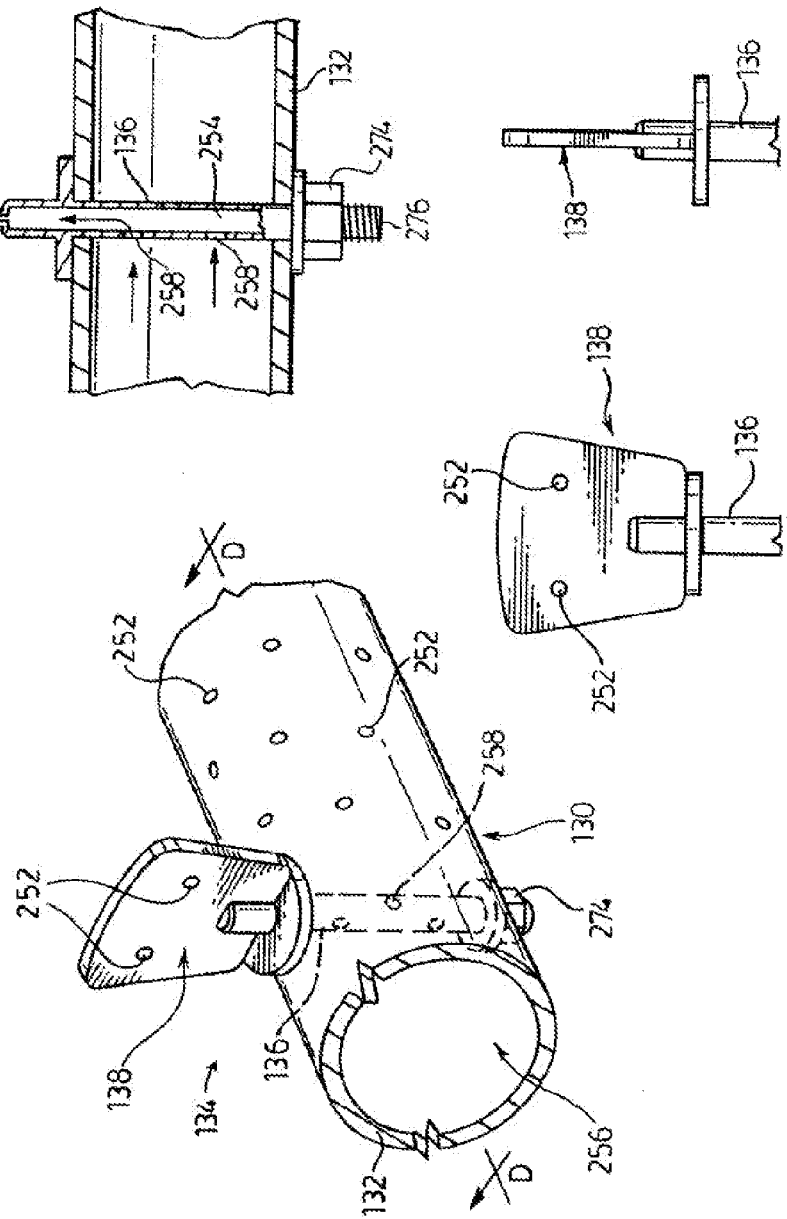

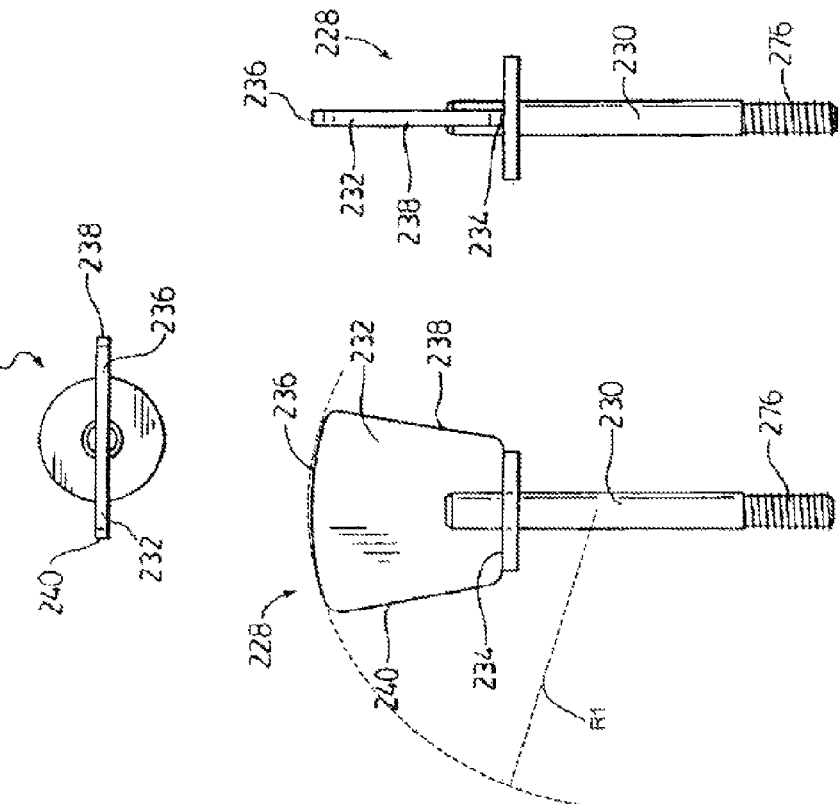
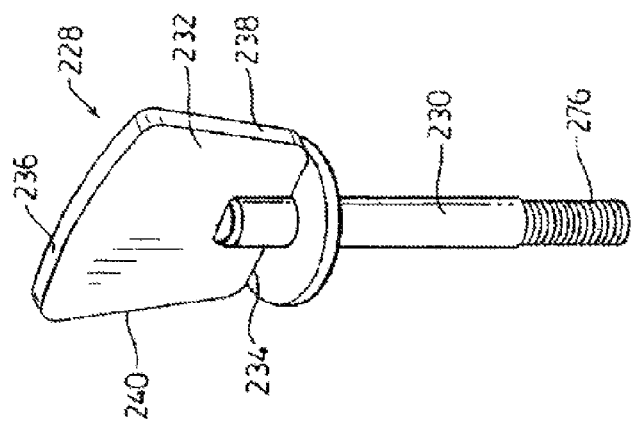
FIG. 25D
FIG. 25C
FIG. 25B
FIG. 25A

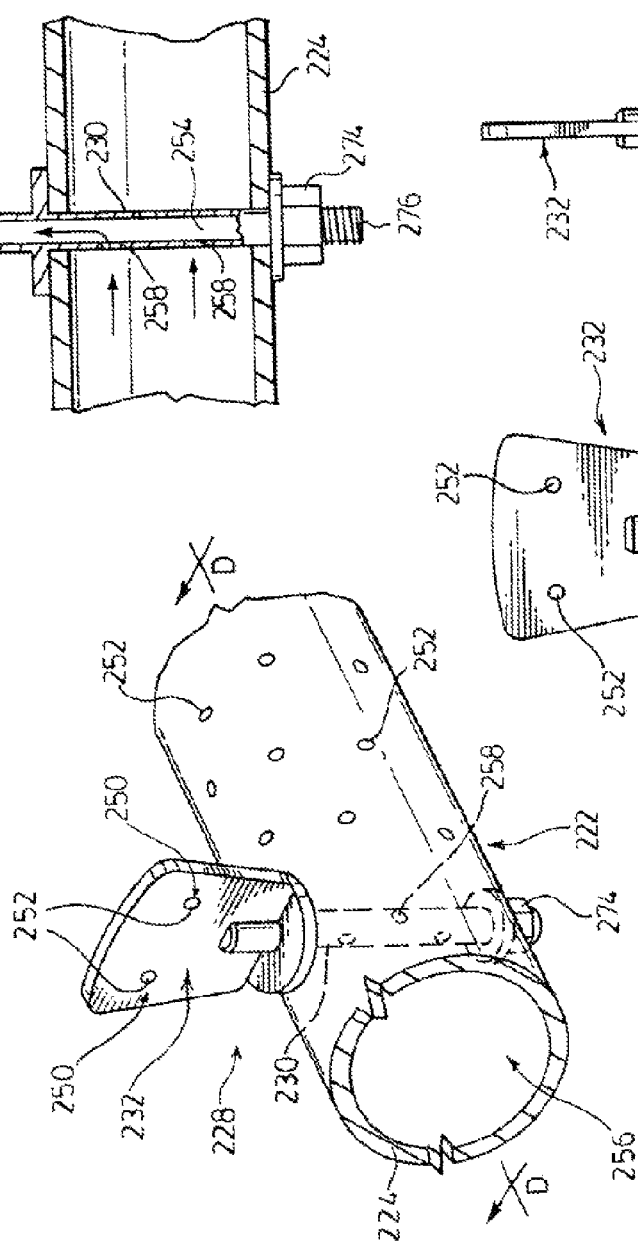
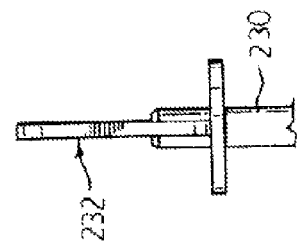
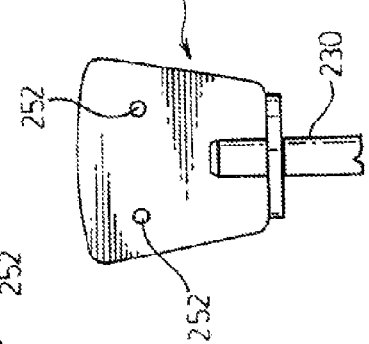
FIG. 26A
FIG. 26B
FIG. 26C
FIG. 26D

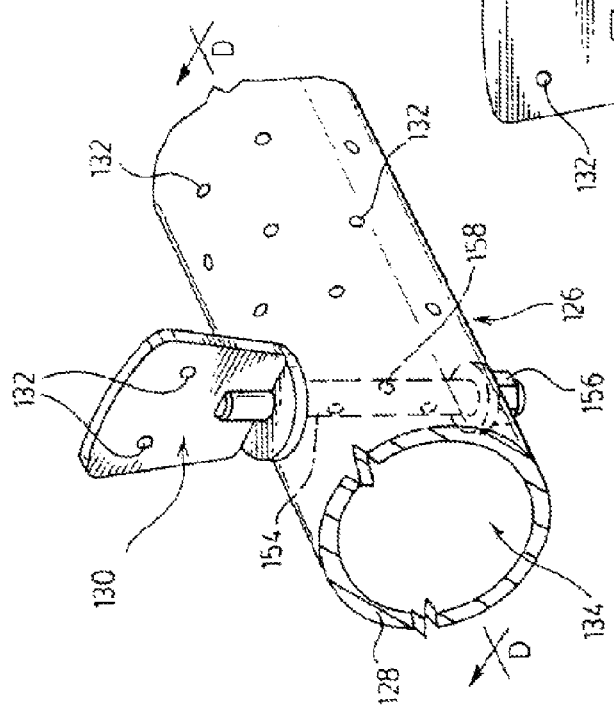
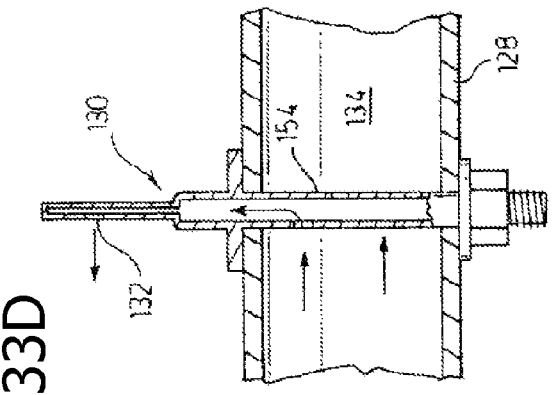
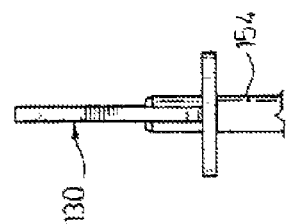
FIG. 33D
FIG. 33C
FIG. 33B
FIG. 33A

METHOD AND APPARATUS FOR TREATING A CELLULOSIC FEEDSTOCK

REFERENCE TO RELATED APPLICATIONS

This application is a Continuation-in-Part application of: (1) U.S. application Ser. No. 12/181,565, filed Jul. 29, 2008, which claims priority to Canadian Patent Application No. 2,638,150 filed on Jul. 24, 2008(2) U.S. application Ser. No. 12/181,596, filed Jul. 29, 2008, which claims priority to Canadian Patent Application No. 2,638,160 filed on Jul. 24, 2008(3) U.S. application Ser. No. 12/181,640, filed Jul. 29, 2008, which claims priority to Canadian Patent Application No. 2,638,159 filed on Jul. 24, 2008(4) U.S. application Ser. No. 12/181,666, filed Jul. 29, 2008, which claims priority to Canadian Patent Application No. 2,638,152 filed on Jul. 24, 2008(5) U.S. application Ser. No. 12/181,724, filed Jul. 29, 2008, which claims priority to Canadian Patent Application No. 2,638,157 filed on Jul. 24, 2008(6) U.S. application Ser. No. 12/361,103, filed Jan. 28, 2009, which claims priority to Canadian Patent Application No. 2,650,919 filed on Jan. 23, 2009; and (7) U.S. application Ser. No. 12/361,149, filed Jan. 28, 2009, which claims priority to Canadian Patent Application No. 2,650,913 filed on Jan. 23, 2009.

GOVERNMENT LICENSE RIGHTS

This invention was made with Government support under DOE Cooperative Agreement Nos. DE-FC36-03GO13142 and DE-FC36-07GO17028. The Government has certain rights in this invention.

FIELD OF THE INVENTION

The invention relates to a method and apparatus for preparing a cellulosic feedstock for the subsequent production of a fermentable sugar stream from the cellulose and hemicellulose in the cellulosic feedstock wherein the fermentable sugar stream may be used for subsequent ethanol production. More specifically, the invention relates to a method and apparatus for treating a cellulosic feedstock by mixing and heating the cellulosic feedstock.

More specifically, the invention relates to a holding tank, and a method of utilizing the holding tank whereby bridging may be reduced or eliminated.

More specifically, the invention relates to a method and apparatus for treating a cellulosic feedstock by moistening and heating the cellulosic feedstock.

More specifically, the invention relates to a holding tank, and a method of utilizing the holding tank to prepare a cellulosic feedstock that may result in a product stream from autohydrolysis or hydrolysis having an improved yield.

The invention also relates to a method and apparatus for treating a cellulosic feedstock for subsequent ethanol production. More specifically, the invention relates to a method and apparatus for preparing the cellulosic feedstock for the subsequent production of a fermentable sugar stream from the cellulose and hemicellulose in the cellulosic feedstock.

The invention further relates to a method and apparatus for obtaining and conveying a cellulosic feedstock, which may be used for the subsequent production of a fermentable sugar stream from the cellulose and hemicellulose in the cellulosic feedstock wherein the fermentable sugar stream may be used for subsequent ethanol production. More specifically, the invention relates to a method and apparatus for withdrawing one or more feedstock stream from a holding tank.

More specifically, the invention relates to a method and apparatus for withdrawing one or more feedstock streams from a holding tank.

BACKGROUND OF THE INVENTION

Several processes for the production of ethanol are known. Generally, the production of fuel ethanol involves the fermentation of sugars with yeast. Typically, the sugars are derived from grains, such as corn and wheat. The starches in the grains are subjected to enzymatic hydrolysis in order to produce the sugars, which are then subjected to fermentation to produce ethanol.

Plant materials are a significant source of fermentable sugars, such as glucose that can be transformed into biofuels. However, the sugars in plant materials are contained in long polymeric chains of cellulose and hemicellulose. Utilizing current fermentation processes, it is necessary to break down these polymeric chains into monomeric sugars, prior to the fermenting step.

Recently, processes have been developed for utilizing plant materials, such as corncobs, straw, and sawdust, to produce sugars for ethanol fermentation. Such processes typically comprise pre-treating the feedstock to increase the accessibility of the cellulose to hydrolysis enzymes, and subjecting the cellulose to cellulase enzyme systems to convert the cellulose into glucose.

Methods of converting plant biomass into fermentable sugars are known in the art and in general comprise two main steps: a pre-treatment step to activate the plant structure, and an enzymatic or chemical hydrolysis step to convert the polymeric chains of cellulose and hemicellulose into monomeric sugars. Several approaches have been used for the pre-treatment step, e.g., autohydrolysis, acid hydrolysis, ammonia activation, kraft pulping, organic solvent pulping, hot water pre-treatment, ammonia percolation, lime pre-treatment, caustic soda pulping, or alkali peroxide pre-treatment. Early pre-treatment steps included grinding or milling the feedstock into a powder, which was then mixed with water to form a slurry.

More recently, solvent based pre-treatments, alkali pre-treatments, and acidic pre-treatments have also been described. PCT publication WO/2007/009463 to Holm Christensen describes an alternate pre-treatment, which does not involve the addition of acids, bases, or other chemicals. This pre-treatment process involves soaking the cellulosic material in water, conveying the cellulosic material through a heated and pressurized reactor, and pressing the cellulosic material to produce a fiber fraction and a liquid fraction. During the soaking step, approximately 2.5-3.5 kg of liquid per 1 kg of fiber is added, and is removed again during pressing. The overall pre-treatment process can take about 27 minutes. After pressing, the cellulosic material is exposed to hydrolysis enzymes.

Each pre-treatment technology has a different mechanism of action on the plant structure, inducing either physical and/or chemical modifications. However, the main objective of the pre-treatment is to provide accessibility of the plant material to the enzymes.

SUMMARY OF THE INVENTION

The commercial viability of a hydrolysis process is dependent on the character of the feedstock provided to the hydrolysis unit. Typically, this requires that a feedstock is activated such that a significant portion (e.g., greater than 75%) of the cellulose and hemicellulose of the feedstock is accessible to hydrolysis enzymes. If such an activated feedstock is provided to an enzymatic hydrolysis unit, then at least 60%, preferably more than 75% and more preferably over 90% of the cellulose and hemicelluloses may be converted to monomeric sugars. This sugar rich process stream may subsequently be subjected to fermentation to produce an alcohol stream. The alcohol stream from the fermentation stage (i.e., the raw alcohol stream) may have an ethanol content of about 3-22% v/v, preferably about 5-15% and more preferably more about 8-12%.

An activated feedstock for enzymatic hydrolysis is preferably prepared by autohydrolysis, which is preferably conducted in a steam explosion reactor also known as a hydrolyzer, (also known as a digester). Autohydrolysis is a process of breaking down hemicellulose and cellulose by exposure to high temperatures, steam and pressure, sometimes in the presence of an added chemical agent, such as an organic or inorganic acid, e.g., sulphuric acid. When performed in the presence of an added acid, the reaction is known as acid hydrolysis.

During autohydrolysis, the degree of polymerization of cellulose may be reduced from about 10,000 to about 1,500-1,000. This process is preferably carried out above the glass transition temperature of lignin (120-160° C.). Depending upon the severity of the reaction, degradation products may be produced, such as furfural, hydroxyl-methylfurfural, formic acid, levulinic acid and other organic compounds.

During a steam explosion treatment (more commonly called autohydrolysis if no externally added catalyst), a cellulosic feedstock is subjected to elevated heat (e.g., 180° C. to 220° C.) and pressure (e.g., 130 psig to 322 psig) optionally in the presence of suitable chemicals (e.g., organic and/or inorganic acids, ammonia, caustic soda, sulfur dioxide, solvents etc.) in a pressurized vessel. Preferably, external chemical addition is not utilized, in which case, the only catalyst that may be present may be acetic acid that is generated in situ. The treated cellulosic feedstock is then released from the pressurized vessel such that the pressure is rapidly reduced (e.g., 1 second or less). The biomass may exit the hydrolyzer into a reduced pressure, preferably atmospheric pressure and, more preferably into a vacuum. The rapid decrease in pressure results in the biomass separating into individual fibers or bundles of fibers. This step opens the fiber structure and increases the surface area. The lignin remains in the fiber along with cellulose and residual hemicellulose. Accordingly, the explosive release of pressure, combined with the high temperature and pressure treatment results in the physico-chemical modification of the cellulosic feedstock that is then suitable for feeding to an enzymatic hydrolysis unit.

In order for the steam explosion process to be able to produce an activated feedstock that is capable of producing such a sugar rich process stream, the temperature and moisture level of the cellulosic feedstock that is fed to a steam explosion reactor preferably is relatively uniform and preferably has a temperature from about 50 to about 70° C., and more preferably 50-65° C. and a moisture content from about 30 to 60 wt % (preferably 45 to about 55 wt %). Moisture content is the quantity of water contained in a material, and on a weight basis, is the weight of water in the material divided by the mass of the material.

Without being limited by theory, it is believed that an unexpected increase in the conversion of the feedstock to fermentable sugars may be achieved if the moisture content of the feedstock fed to the steam explosion reactor is lower, provided that sufficient water is present for hydrolyzing and/or activating the feedstock. If the feedstock is too dry, then there may be insufficient water molecules present in the water and hence not all of the feedstock will be activated and/or hydrolyzed (i.e., the hydrolysis reaction/activation will not occur at all possible sites). Accordingly, it might be presumed that a substantial excess of water should be used to ensure water molecules are available at each hydrolysis/activation site. Surprisingly, it has been determined that if the cellulosic feedstock that is fed to a steam explosion reactor has an excess of moisture then a smaller percentage of the available sites of the feedstock are activated and/or hydrolyzed than would be expected. It is believed that this is due to the high moisture content acting as a barrier to heat transfer through the fiber structure. The external fiber reaches the process temperature far in advance to the internal fiber, hence resulting in very uneven heat transfer and the resulting uneven autohydrolysis reaction. Further, during the autohydrolysis process additional water may be provided to the process by way of direct injected steam in order to raise the fiber temperature from the inlet temperature to the outlet temperature of the reactor. If the inlet moisture content of the fiber is at saturation, then the additional water will be free water in the autohydrolysis reactor resulting in washing of the soluble hemicellulose from the fiber and causing subsequent accumulation of hemicellulose within the reactor. Over time, the accumulated hemicellulose will tend to break down to inhibitor compounds and deposit degraded sugars on the internal components of the reactor. These deposits will become an obstruction to the flow of the biomass.

It has also been determined that if the cellulosic feedstock that is fed to a hydrolyzer has a temperature that is too high, then some percentage of the hemicellulose sugars will be degraded to inhibitory compounds prior to starting the autohydrolysis reaction and further amounts during the autohydrolysis reaction itself. Conversely, if the fiber is too cold entering the hydrolyzer (e.g. autohydrolysis reactor), the first one third to one half of the reactor vessel may act as a pre-heating device rather than as an autohydrolysis reactor, resulting in incomplete autohydrolysis. Accordingly, it is preferred to have very consistent fiber temperature year round as well as from night to day time operation, for the fiber that is fed to the hydrolyzer reactor. Further, it may be preferred that the fiber in the feedstock fed to the autohydrolysis unit have a relatively uniform temperature profile. For example, it is preferred that the core of the blocks of material have a temperature that is within 80%, preferably 90% of the temperature of the exterior surface of the material. Accordingly, for example, if the temperature of the exterior surface of the material is from 50 to 70° C., then the temperature of the core of the material is preferably from 45 to 63° C.

Alternately, and in addition, it is preferred that the fiber in the feedstock fed to the autohydrolysis unit have a relatively uniform temperature profile. For example, it is preferred that the core of the feedstock material have a temperature that is within 80%, more preferably 90%, most preferably 95% of the temperature of the exterior surface of the material. Accordingly, for example, if the temperature of the exterior surface of the material is from 50 to 70° C., then the temperature of the core of the material is preferably from 45 to 63° C.

It has also been determined that the fiber requires time for the moisture that is added to become equilibrated throughout the entire fiber particle. It has been determined that under laboratory conditions, it may take from 5 to 9 minutes to equilibrate the moisture content of the fiber. Under industrial conditions it will be longer. Preferably, the autohydrolysis reaction time in the vessel is typically about 5 to 6 minutes or less. Accordingly, it may be preferred that a soaking or impregnation stage is conducted prior to the autohydrolysis reaction. It is preferred that the fiber in the feedstock fed to the autohydrolysis unit have a relatively uniform moisture profile. For example, it is preferred that the core of the blocks of material have a moisture content that is within 80%, more preferably 90%, most preferably 95% of the moisture content of the exterior surface of the material. Accordingly, for example, if the moisture content of the exterior surface of the material is from 45 to 55 wt %, then the moisture content of the core of the material is preferably from 40.5 to 49.5 wt %.

A feedstock having a moisture content from about 45 to about 55 wt % may be prepared by obtaining relatively dry plant material which is broken down into small chips, e.g., from about 0.05 to about 2 inches, and then combining the chip with water (e.g., steam and/or a fine mist spray, such as droplets of water of between 600 μm and 900 μm in diameter). This material may then be transported to a hydrolysis or auto hydrolysis reactor. This material is difficult to transport as the material is essentially a solid (having insufficient water to form even a slurry). Accordingly, the material has a tendency to interlock and may result in process vessels or flow passages between equipment becoming blocked.

Accordingly, embodiments of the present invention relate to a cellulosic feedstock pre-treatment apparatus which mixes the feedstock, optionally with heating and/or moisture addition, to prepare the feedstock for hydrolysis, and a method of use thereof. Subsequent to this soaking or impregnation stage, it is preferred to subject the feedstock to an autohydrolysis reaction.

In one broad aspect, an apparatus for conveying a cellulosic feedstock is provided. The apparatus comprises an enclosed volume having a length along which the cellulosic feedstock is conveyed. The enclosed volume has a lower surface comprising a plurality of longitudinally extending portions. Each longitudinally extending portion has an inner surface that is arcuate in transverse section. A plurality of conveyance members are provided within the enclosed volume. Each conveyance member is associated with one of the inner surfaces and configured to sweep the one of the inner surfaces.

In various aspects, an apparatus for conveying a moisture-impregnated cellulosic feedstock is provided. The apparatus comprises an enclosed volume having a length along which the cellulosic feedstock is conveyed. The enclosed volume has a lower surface comprising a plurality of longitudinally extending portions. Each longitudinally extending portion has an inner surface that is arcuate in transverse section. A plurality of conveyance members are provided within the enclosed volume. Each conveyance member is associated with one of the inner surfaces and configured to sweep the one of the inner surfaces.

In various other aspects, an apparatus for conveying an acid-impregnated cellulosic feedstock is provided. The apparatus comprises an enclosed volume having a length along which the cellulosic feedstock is conveyed. The enclosed volume has a lower surface comprising a plurality of longitudinally extending portions. Each longitudinally extending portion has an inner surface that is arcuate in transverse section. A plurality of conveyance members are provided within the enclosed volume. Each conveyance member is associated with one of the inner surfaces and configured to sweep the one of the inner surfaces.

Embodiments in accordance with this broad aspect may be advantageous because the apparatus may convey the cellulosic material in a substantially continuous fashion, while preventing blockages from occurring, and preventing material from becoming stuck in the apparatus or having a residence time that is excessive. Furthermore, embodiments in accordance with this broad aspect may be advantageous because the enclosed volume may prevent the cellulosic material from drying out, and from losing heat. Further, embodiments in accordance with this broad aspect may allow the cellulosic material to be conveyed through the enclosed volume while being mixed. Accordingly, the temperature and moisture content of the cellulosic feedstock may be substantially homogenous throughout the feedstock. This cellulosic feedstock is preferably used for subsequent ethanol production. For example, the heated moistened feedstock may be subsequently subjected to hydrolysis, preferably autohydrolysis followed by enzymatic hydrolysis.

In some embodiments, each conveyance member comprises a longitudinally extending rotary shaft, and a conveying member (e.g., a plurality of paddles or a continuous screw on a shaft) extending outwardly from the shaft and in the case of discrete members such as paddles, staggered axially along the shaft.

In some embodiments, the conveying member and the lower surface are configured to maintain a space between the conveying member and the lower surface of less than 6.5 mm. In accordance with this embodiment, if the conveying member comprises a plurality of paddles, then the paddles and the lower surface are configured to maintain a space between a given paddle and the lower surface of less than 6.5 mm when the given paddle is adjacent the lower surface. The spacing may vary depending upon the size of the particulate matter in the feedstock. The larger the size of the particulate matter, the larger the spacing may be. Preferably, the spacing is less than the maximum particle size and, more preferably, less than the median particle size. For example, if each portion has a lower surface that is semi circular, the conveyance member associated with each portion may be configured to sweep the lower surface. As the shafts rotate, particulate matter will be continually moved through the chamber despite the lower surface of the apparatus having a smooth, continuous lower surface.

In some embodiments, the conveying member comprises a plurality of paddles each comprising a generally planar blade having a radial inner edge attached to stem, a radial outer edge opposite the radial inner edge, and opposing first and second side edges extending between the radial inner and outer edges, and the radial outer edge is curved to match an arc swept by the outer edge when the shaft rotates.

In some embodiments, each blade is canted, wherein the first side edge is axially nearer the outlet and rotationally trailing relative to a second side edge.

In some embodiments, the first side edge of one paddle axially overlaps the second side edge of a next adjacent paddle.

In some embodiments, adjacent shafts are spaced transversely apart from each other and are generally parallel and rotate in opposite directions.

In some embodiments, at least some of the paddles have an arcuate radial outer edge that is shaped to mate with at least one of the inner surfaces.

In some embodiments, each inner surface defines a first sector of a circle having a first radius and a radial outer edge of each paddle describes a second sector of a circle having a second radius as it rotates, and the second radius is essentially the same as the first radius of at least one of the inner surfaces.

In some embodiments, the paddles are staggered circumferentially along the shaft.

In some embodiments, the enclosed volume comprises an upper inner arcuate surface having first and second transversely opposed lower longitudinally extending sides, wherein one of the longitudinally extending portions has an upper outer side configured to merge with the first lower longitudinally extending side, and another of the longitudinally extending portions has an upper outer side configured to merge with the second lower longitudinally extending side.

In some embodiments, the longitudinally extending portions are positioned side-by-side.

In further embodiments, the apparatus may be configured to provide heat and/or moisture to the cellulosic feedstock, in order to maintain or raise the feedstock to a desired moisture content and temperature as it is conveyed, or to pre-treat the cellulosic feedstock by further moistening and heating the cellulosic feedstock.

In some such embodiments, the conveyance members have fluid injection ports. In further embodiments, each conveyance member comprises a longitudinally extending rotary shaft and the shaft comprises a fluid conduit extending longitudinally therethrough. In yet further embodiments, the shaft comprises a fluid conduit extending longitudinally therethrough and at least one of the stem and the paddles comprise injection ports.

In a further broad aspect, a method is provided for conveying a cellulosic feedstock. The method comprises providing a cellulosic feedstock being less than 100% saturated with moisture, preferably less than 50% moisture on a weight basis and more preferably less than 15 wt % (e.g., 5-15 wt %). Moisture content is the quantity of water contained in a material, and on a weight basis, is the weight of water in the material divided by the mass of the material. The cellulosic feedstock is introduced into a longitudinally extending enclosed volume, and conveyed longitudinally through the enclosed volume while being heated. The cellulosic feedstock is mixed as it is conveyed through the enclosed volume.

Embodiments in accordance with this broad aspect may be advantageous because the heating and mixing of the feedstock may produce a more uniform temperature and moisture content of the feedstock thereby enhancing downstream hydrolysis of the feedstock. Furthermore, the process permits the heating and mixing of the feedstock while requiring relatively small amounts of heat and energy. Accordingly, the process may prevent overheating of the fibers in the feedstock, thereby preventing degradation of the fibers.

In some embodiments, the method further comprises operating the enclosed volume at less then 100% fill volume, whereby an upper portion of the enclosed volume is open. Preferably, the process is operated such that the enclosed volume may operate at a low fill factor, for example from 10 to 50 and preferably about 30%.

In some embodiments, the step of mixing the cellulosic feedstock comprises projecting a portion of the cellulosic feedstock into the upper open portion of the enclosed volume while conveying the cellulosic feedstock longitudinally through the enclosed volume.

In some embodiments, the enclosed volume has a plurality of longitudinally extending portions, each portion has an inner surface that is arcuate in transverse section, and the method further comprises conveying the cellulosic feedstock longitudinally along each inner surface.

In some embodiments, the enclosed volume has a lower surface, and the method further comprises sweeping a lower surface to convey the cellulosic feedstock through the enclosed volume.

In some embodiments, the lower surface comprises a plurality of longitudinally extending portions, and the method further comprises rotating a plurality of conveyance members to pass conveying members of each conveyance member proximate one of the inner surfaces such that conveying members of each conveyance member contact the cellulosic feedstock and urge the cellulosic feedstock along the length of each inner surface.

In some embodiments, the method further comprises maintaining a residence time of less than 10 minutes.

In some embodiments, the feedstock is mixed such that the feedstock has a generally uniform moisture content of 30 to 60% by weight, preferably 45% to 55% by weight, upon exiting the enclosed volume.

In some embodiments, the method further comprises conveying the cellulosic feedstock downwardly to a holding tank upon exiting the enclosed volume.

In some embodiments, the method further comprises subsequently subjecting the cellulosic feedstock to a downstream hydrolysis process, preferably autohydrolysis followed by enzymatic hydrolysis.

In a further broad aspect, a method for conveying a cellulosic feedstock is provided. The method comprises (i) providing a cellulosic feedstock being less than 100% saturated with moisture; (ii) introducing the cellulosic feedstock into a longitudinally extending enclosed volume, wherein the enclosed volume has a length along which the cellulosic feedstock is conveyed, the enclosed volume having a lower surface comprising a plurality of longitudinally extending portions, each portion having an inner surface that is arcuate in transverse section; (iii) conveying the cellulosic feedstock longitudinally through the enclosed volume while heating the cellulosic feedstock, wherein the cellulosic feedstock is conveyed by a plurality of conveyance members provided within the enclosed volume, each conveyance member being associated with one of the inner surfaces and configured to sweep the one of the inner surfaces; and (iv) mixing the cellulosic feedstock as it is conveyed through the enclosed volume.

In another broad aspect, a method for conveying a cellulosic feedstock is provided. The method comprises: (i) providing a cellulosic feedstock; (ii) introducing the cellulosic feedstock into a longitudinally extending enclosed volume, wherein the enclosed volume has a length along which the cellulosic feedstock is conveyed, the enclosed volume having a lower surface comprising a plurality of longitudinally extending portions, each portion having an inner surface that is arcuate in transverse section; (iii) conveying the cellulosic feedstock longitudinally through the enclosed volume while heating the cellulosic feedstock, wherein the cellulosic feedstock is conveyed by a plurality of conveyance members provided within the enclosed volume, each conveyance member being associated with one of the inner surfaces and configured to sweep the one of the inner surfaces; and (iv) mixing the cellulosic feedstock as it is conveyed through the enclosed volume.

A further broad aspect provides a method for conveying a cellulosic feedstock. The method comprises: (i) providing a cellulosic feedstock having a moisture content of less than 50 weight percent; (ii) introducing the cellulosic feedstock into a longitudinally extending enclosed volume and conveying the cellulosic feedstock longitudinally through the enclosed volume while heating the cellulosic feedstock; and (iii) mixing the cellulosic feedstock as it is conveyed through the enclosed volume.

Embodiments of the present invention provide a method and apparatus for transporting a cellulosic feedstock. The method and apparatus relate to a holding tank that can be positioned downstream from a cellulosic feedstock pre-treatment process, and that can be utilized to further prepare the cellulosic feedstock for, e.g., auto hydrolysis or hydrolysis.

In one broad aspect, a method of preparing a cellulosic feedstock for ethanol production is provided. The method comprises passing the cellulosic feedstock through an impregnation chamber to an outlet of the impregnation chamber, passing the cellulosic feedstock from the outlet of the impregnation chamber to a holding tank having an inlet and an outlet, and conveying the cellulosic feedstock downwardly and laterally as it travels through the holding tank.

In various embodiments, the method of preparing a cellulosic feedstock for ethanol production comprises passing the cellulosic feedstock through an impregnation chamber to an outlet of the impregnation chamber; passing the cellulosic feedstock from the outlet of the impregnation chamber to a holding tank, the holding tank having (i) at least one sidewall defining a passage having an upper portion and a lower portion, the lower portion having a greater cross sectional area than the upper portion; (ii) at least one inlet adjacent the upper portion; and, (iii) at least one outlet adjacent the lower portion, at an elevation below the inlet; and conveying the cellulosic feedstock downwardly and laterally as it travels through the holding tank.

In various other embodiments, the method of preparing a cellulosic feedstock for ethanol production comprises passing the cellulosic feedstock through an impregnation chamber to an outlet of the impregnation chamber; passing the cellulosic feedstock from the outlet of the impregnation chamber to a holding tank, the holding tank having (i) at least one sidewall defining a passage having an upper portion and a lower portion, the lower portion having a cross sectional area and the upper portion having cross sectional area, the cross section areal of the lower portion being at least equal to the cross sectional area of the upper portion; (ii) at least one inlet adjacent the upper portion; and, (iii) at least one outlet adjacent the lower portion, at an elevation below the inlet; and conveying the cellulosic feedstock downwardly and laterally as it travels through the holding tank.

Embodiments in accordance with this broad aspect also include methods of preparing fermentable sugars from a cellulosic feedstock. In some embodiments, the method comprises passing the cellulosic feedstock through an impregnation chamber to an outlet of the impregnation chamber; passing the cellulosic feedstock from the outlet of the impregnation chamber to a holding tank, the holding tank having an inlet and an outlet; and, conveying the cellulosic feedstock downwardly and laterally as it travels through the holding tank, wherein the residence time of the cellulosic feedstock in the holding tank is from about 5 to about 45 minutes.

In other embodiments, the method of preparing fermentable sugars from a cellulosic feedstock comprises passing the cellulosic feedstock through an impregnation chamber to an outlet of the impregnation chamber; passing the cellulosic feedstock from the outlet of the impregnation chamber to a holding tank, the holding tank having an inlet and an outlet; conveying the cellulosic feedstock downwardly and laterally as it travels through the holding tank; and passing the cellulosic feedstock from the outlet of the holding tank to a hydrolysis reactor.

Embodiments in accordance with this broad aspect may be advantageous because the lateral movement of the feedstock assists in preventing the feedstock from plugging the apparatus. In particular, if the holding tank had walls that extended vertically and defined a vertical passage therethrough, then the feedstock would travel vertically downwardly. Due to the nature of the feedstock, the feedstock has a tendency to bridge the vertically extending passage, resulting in some, or possibly all, of the passage becoming blocked. Bridging of the passage can result in the need for manual intervention, as well as monitoring, to ensure that feed material is supplied to downstream process equipment on a continuous basis. Further, if the holding tank is provided with a steam jacket, overly long holdup of material in the holding tank could result in degradation of some of the cellulose and hemicellulose in the feedstock.

In some embodiments, the method further comprises maintaining a temperature in the holding tank between about 50° Celsius and about 75° Celsius. Such embodiments may be advantageous because the elevated temperature may prepare the feedstock exiting the holding tank to be at a predetermined temperature for the next process stage. Further, if the feedstock entering the holding tank is at the predetermined temperature for the next process stage, the feedstock may be maintained at a desired temperature as it passes through the holding tank.

In some embodiments, the cellulosic feedstock moves from the inlet to the outlet of the holding tank in about 10 to about 30 minutes.

In some embodiments, the inlet of the holding tank is disposed at an elevation above the outlet of the holding tank, and the cellulosic feedstock migrates from the inlet towards the outlet of the holding tank under the force of gravity.

In some embodiments, the holding tank comprises an outlet, and the method further comprises conveying the cellulosic feedstock laterally across the outlet.

In some embodiments, the step of conveying the cellulosic feedstock laterally across the outlet comprises actively withdrawing the cellulosic feedstock from essentially an entirety of the outlet.

In some embodiments, the step of conveying the cellulosic feedstock laterally across the outlet comprises withdrawing a generally equal amount of cellulosic feedstock from each portion of the outlet.

In some embodiments, the step of conveying the cellulosic feedstock laterally across the outlet comprises withdrawing a first portion of the cellulosic feedstock in a first lateral direction and withdrawing a second portion of the cellulosic feedstock in a second lateral direction.

In another broad aspect, a holding tank for a cellulosic feedstock, moisture-impregnated cellulosic feedstock, and/or an acid-impregnated cellulosic feedstock is provided. The holding tank apparatus comprises at least one sidewall defining a passage. The passage has an upper portion and a lower portion, and the lower portion has a greater cross-sectional area than the upper portion. At least one inlet is provided adjacent the upper portion, and at least one outlet is provided adjacent the lower portion, at an elevation below the inlet.

Embodiments in accordance with this broad aspect may be advantageous because providing the lower portion with a greater cross-sectional area than the upper portion may prevent cellulosic material from adhering or sticking to the sidewalls as the cellulosic material passes through the holding tank. Accordingly, each portion of cellulosic feedstock that passes through the holding tank may have essentially the same residence time in the passage. This may be advantageous in helping to ensure that the feedstock exiting the holding tank has a more uniform temperature and/or moisture content.

In various embodiments, a holding tank for a cellulosic feedstock, moisture-impregnated cellulosic feedstock, and/or an acid-impregnated cellulosic feedstock is provided which comprises at least one sidewall defining a passage having an upper portion having a cross sectional area and a lower portion having a cross sectional area, the cross sectional area of the lower portion being at least equal to the cross sectional area of the upper portion; at least one inlet adjacent the upper portion; and, at least one outlet adjacent the lower portion, at an elevation below the inlet.

In some embodiments, a holding tank for a cellulosic feedstock, moisture-impregnated cellulosic feedstock, and/or an acid-impregnated cellulosic feedstock is provided which comprises at least one sidewall defining a passage having an upper portion and a lower portion, the lower portion having a greater cross sectional area than the upper portion; at least one inlet adjacent the upper portion; at least one outlet adjacent the lower portion, at an elevation below the inlet; at least one discharge member below the outlet, the discharge member comprising one or more screw conveyors, one or more paddle conveyors, one or more sweeping conveyors, one or more sweeping arms, one or more rotational disks, or one or more metering screws; and a collection and conveyance member in fluid communication with the at least one discharge member.

In some embodiments, the sidewalls comprise a first sidewall and a second sidewall opposed to the first sidewall, and the first and second sidewalls diverge relative to each other from the upper portion to the lower portion.

In some embodiments, the sidewalls comprise a third sidewall and a fourth sidewall opposed to the third sidewall. The third and fourth sidewalls extend between the first and second sidewalls, and the third and fourth sidewalls diverge relative to each other from the upper portion to the lower portion.

In some embodiments, the holding tank apparatus further comprises at least one discharge member adjacent the outlet. The discharge member may serve to withdraw the cellulosic feedstock from the outlet and direct it towards one or more hydrolysis reactors.

In some embodiments, the at least one discharge member comprises a base and an open top that is at least as large as, and is in vertical registration with, the outlet, and at least a first discharge member outlet that is laterally positioned.

In some embodiments, the at least one discharge member comprises at least one screw conveyor mounted above the base.

In some embodiments, the at least one discharge member comprises a first pair of screw conveyors, and each screw conveyor in the first pair rotates about respective first and second generally parallel axes. In some embodiments, the axes extend at an angle of less than 45° relative to horizontal. In further embodiments, the axes are generally horizontal.

In some embodiments, the screw conveyors are rotated in the same direction and feed material from above towards the first discharge member outlet.

In some embodiments, the screw conveyors have a first pitch adjacent the first discharge member outlet, and a second pitch narrower than the first pitch distal to the first discharge member outlet. Such embodiments may be advantageous because a generally equal amount of feedstock may be withdrawn from each portion of the lower end.

In some embodiments, the screw conveyors each have a first flight and a second flight, and the first flight has a first pitch and is disposed adjacent the first discharge member outlet, and the second flight has second pitch narrower than the first pitch and is disposed along the shaft upstream from the first flight. In some further embodiments, each screw conveyor comprises a third flight intermediate the first and second flights, and the third flight has an intermediate pitch that is wider than the first pitch and narrower than the wider pitch.

In some embodiments, the discharge member further comprises a second pair of screw conveyors. In some such embodiments, the screw conveyors of the second pair are rotatable about parallel axes. Preferably, the axes are generally horizontal. Further, each screw conveyor in the second pair preferably rotates in the same direction.

In some embodiments, the second pair of screw conveyors urges material from above towards a second discharge member outlet that is laterally positioned and spaced away from the first discharge member outlet.

In some embodiments, the second discharge member outlet is laterally opposed to the first discharge member outlet. In some further embodiments, the screw conveyors of first pair rotate opposite to the screw conveyors of second pair.

In some embodiments, the holding tank apparatus further comprises a heating jacket provided on at least a portion of the sidewalls. In some embodiments, the heating jacket is provided on the sidewalls.

In another aspect, a holding tank for an acid-impregnated cellulosic feedstock is provided. The holding tank for an acid-impregnated cellulosic feedstock comprises a plurality of sidewalls defining a passage having an upper portion having a cross sectional area and a lower portion having a cross sectional area, the cross sectional area of the lower portion being at least equal to the cross sectional area of the upper portion; at least one inlet adjacent the upper portion; at least one outlet adjacent the lower portion, at an elevation below the inlet; and, at least one discharge member comprising a base and an open top that is at least as large as, and is in vertical registration with, the at least one outlet, wherein the holding tank is constructed of acid-resistant materials.

In still another aspect, an apparatus for conveying acid-impregnated cellulosic feedstock is provided. The apparatus for conveying acid-impregnated cellulosic feedstock a holding tank comprises (i) a plurality of sidewalls defining a passage having an upper portion having a cross sectional area and a lower portion having a cross sectional area, the cross sectional area of the lower portion being at least equal to the cross sectional area of the upper portion, (ii) at least one inlet adjacent the upper portion, (iii) at least one outlet adjacent the lower portion, at an elevation below the inlet, and (iv) at least one discharge member comprising a base and an open top that is at least as large as, and is in vertical registration with, the at least one outlet, wherein the holding tank is constructed of acid-resistant materials; an impregnation vessel in fluid communication with the holding tank; and a hydrolysis reactor in fluid communication with the holding tank.

Accordingly, embodiments of the present invention relate to a cellulosic feedstock pre-treatment process, which comprises the addition of moisture to a cellulosic feedstock, while mixing the feedstock, to prepare the feedstock for hydrolysis. Subsequent to this soaking or impregnation stage, it is preferred to subject the feedstock to an autohydrolysis reaction.

In one broad aspect, a method is provided for treating a cellulosic feedstock, such as for subsequent ethanol production. The method comprises conveying the cellulosic feedstock through an enclosed volume. The method further comprises adding moisture to the cellulosic feedstock simultaneously at multiple spaced-apart moisture injection points as the cellulosic feedstock travels through the volume, and heating the cellulosic feedstock as it travels through the volume to obtain a heated moistened feedstock. In some embodiments, the heated moistened feedstock is subsequently subjected to hydrolysis, preferably autohydrolysis followed by enzymatic hydrolysis.

In various embodiments, the method for treating a cellulosic feedstock comprises a) conveying the cellulosic feedstock having a moisture content through an enclosed volume, wherein the enclosed volume comprises i) a shell defining a treatment chamber having a lower inner surface, the shell having an inlet and an outlet spaced longitudinally apart from the inlet to define an axial length, ii) a conveyance member housed within the shell and configured to sweep the lower inner surface and, iii) a plurality of injection ports provided in at least one of the shell and the conveyance member; b) adding moisture to the cellulosic feedstock simultaneously at multiple spaced-apart moisture injection points as the cellulosic feedstock travels through the volume; and, c) heating the cellulosic feedstock as it travels through the volume and obtaining a heated moistened feedstock.

In some embodiments, a method for treating a cellulosic feedstock comprises a) conveying the cellulosic feedstock having a moisture content through an enclosed volume, wherein the enclosed volume comprises i) a shell defining a treatment chamber having a lower inner surface, the shell having an inlet and an outlet spaced longitudinally apart from the inlet to define an axial length, ii) a conveyance member housed within the shell and configured to sweep the lower inner surface and, iii) a plurality of injection ports provided in at least one of the shell and the conveyance member; b) adding moisture to the cellulosic feedstock simultaneously at multiple spaced-apart moisture injection points as the cellulosic feedstock travels through the volume; and, c) heating the cellulosic feedstock as it travels through the volume and obtaining a heated moistened feedstock.

In some embodiments, the volume comprises an impregnation chamber defined by chamber walls having an inner surface, and the impregnation chamber extends longitudinally along an axial length from an intake to an outlet, and the cellulosic feedstock is urged through the chamber by a conveyance member.

In some embodiments, the step of adding moisture comprises adding moisture to increase the moisture content of the cellulosic feedstock from about 5-15 wt % to about 45-55 wt %. In some embodiments, the method further comprises adding heated water as at least part of the moisture. In some embodiments, the method further comprises adding a catalyst with the moisture. Preferably, the heated water is at a temperature up to 70° C. and preferably about 50-60° C.

In some embodiments, the step of heating the cellulosic feedstock comprises heating the cellulosic feedstock from less than about 30° Celsius at the inlet, to at least about 65° Celsius at the outlet.

In some embodiments, the plurality of injection points comprises a plurality of ports extending through the chamber wall commencing proximate the inlet and the method further comprising introducing moisture to the cellulosic feedstock at least during its initial travel through the impregnation chamber. In some further embodiments, the injection points are provided in a first third of the axial length of the impregnation chamber.

In some embodiments, the step of heating the cellulosic feedstock comprises heating the cellulosic feedstock to about 50-70° Celsius at the outlet. In some embodiments, the step of heating the cellulosic feedstock comprises heating the moisture prior to contacting the moisture with the feedstock.

In some embodiments, the step of heating the cellulosic feedstock comprises indirectly heating the cellulosic feedstock by heating at least one of the chamber walls and the conveyance member.

In some embodiments, the conveyance member extends longitudinally through the impregnation chamber and is configured to urge the cellulosic feedstock axially through the impregnation chamber as the conveyance member rotates.

In some embodiments, the conveyance member comprises a rotary shaft extending longitudinally through the impregnation chamber and a plurality of paddles extending radially outwardly from the shaft, and the method further comprises rotating the shaft to urge the cellulosic feedstock axially through the impregnation chamber.

In some embodiments, the conveyance member includes moisture injection points, and the method further comprises introducing moisture to the volume as the conveyance member rotates.

In some embodiments, the conveyance member includes a fluid conduit extending longitudinally through the shaft and a plurality of paddle ducts in communication with the fluid conduit and extending through the paddle to an outer surface thereof, and the step of adding moisture to the cellulosic feedstock comprises injecting moisture into the feedstock through the paddle ducts.

In some embodiments, the conveyance member comprises a rotary shaft extending longitudinally through the impregnation chamber, and a plurality of paddles extending radially outwardly from the shaft, and the paddles are configured relative to the impregnation chamber to sweep at least a lower circumferential portion of the inner surface of the chamber walls when the feedstock is conveyed through the chamber.

In some embodiments, the conveyance member comprises a rotary shaft extending longitudinally through the impregnation chamber and a plurality of paddles extending radially outwardly from the shaft and the paddles are spaced and configured such that the lower circumferential portion of the chamber is swept along generally the entire axial length of the chamber as the feedstock is conveyed through the chamber.

In some embodiments, the volume has a residence time of less than about ten minutes. Such embodiments may be advantageous because the process may be substantially fast, and may prevent overheating of the fibers, thereby preventing degradation of the fibers.

In some embodiments, the method further comprises monitoring the moisture content of the feedstock and introducing an amount of moisture to produce a predetermined moisture content of the heated moistened feedstock.

In some embodiments, the method further comprises providing a feedstock comprising cellulosic material that has a moisture content of less than about 50 wt % and comprises fibers that have a length in the range of about 4 mm to about 7 mm. More preferably, the feedstock comprises a moisture content from 5 to 45 wt % and more preferably from 10 to 30 wt %.

In some embodiments, the method further comprises subsequently subjecting the cellulosic feedstock to a downstream hydrolysis process.

In another broad aspect, apparatus for treating a cellulosic fiber feedstock, moisture-impregnated cellulosic fiber feedstock, and an acid-impregnated cellulosic fiber feedstock are provided. The apparatus comprises a shell defining a treatment chamber having a lower inner surface. The treatment chamber has an inlet and an outlet spaced longitudinally apart from the inlet to define an axial length. A conveyance member is housed within the shell and is configured to sweep the lower inner surface. A plurality of injection ports are provided in at least one of the shell and the conveyance member.

In some embodiments, the plurality of injection ports comprises about 1 to 20 injection ports.

In some embodiments, the plurality of injection ports are positioned along at least a first portion of the axial length of the shell, wherein the first portion extends from the inlet towards the outlet.

In some embodiments, the conveyance member comprises at least a first rotary shaft and a plurality of paddles joined to the first shaft and extending radially outwardly therefrom.

In some embodiments, the paddles and the lower inner surface are configured to maintain a minimum space between the paddles and the lower inner surface of less than 6.5 mm.

In some embodiments, the paddles comprise blades, and the blades are generally planar members, having a radially inner edge attached to a stem, a radially outer edge opposite the radially inner edge, and opposing first and second side edges extending between the radially inner and outer edges. The radially outer edge may be curved to match an arc swept by the outer edge when the first shaft rotates.

In some embodiments, each blade is canted, wherein the first side edge is axially nearer the outlet and rotationally trailing relative to a second side edge.

In some embodiments, axially adjacent paddles extend from the shaft at different angular positions around to the shaft axis.

In some embodiments, the first side edge of one paddle axially overlaps the second side edge of a next adjacent paddle.

In some embodiments, the conveyance member comprises a second shaft, spaced transversely apart from and extending generally parallel to the first shaft and the lower inner surface is scallop shaped in transverse section.

In some embodiments, the conveyance member comprises a second shaft, spaced transversely apart from and extending generally parallel to the first shaft, each shaft has a plurality of paddles attached thereto, and the lower inner surface has a first portion below the first shaft and a second portion below the second shaft wherein, when viewed in transverse cross section, the first portion defines an arc at a constant distance to the first shaft and the second portion defines an arc at a constant distance to the second shaft.

In some embodiments, the second shaft rotates in an opposite direction to the first shaft.

In some embodiments, the apparatus further comprises a first heated fluid supply in fluid communication with the injection ports. In some embodiments, the first heated fluid supply comprises water heated to a temperature from about 60 to about 70° C. In some embodiments, the first heated fluid supply comprises a catalyst.

In some embodiments, the apparatus further comprises a jacket surrounding at least a portion of the shell and defining an enclosure between the jacket and the shell. In some embodiments, the apparatus further comprises a second heated fluid supply associated with the enclosure. In some embodiments, the second heated fluid supply comprises steam.

In some embodiments, the shaft comprises a conduit extending longitudinally therethrough. In some further embodiments, the conveyance member includes injection ports. In yet further embodiments, at least one of the stem and the paddles comprise injection ports.

In some embodiments, the apparatus further comprises a moisture sensor that measures the moisture content of the cellulosic fiber feedstock and a controller operatively controlling an amount of moisture introduced through the injection ports. Accordingly, a predetermined moisture content of the cellulosic fiber feedstock is obtained at the outlet. In some embodiments, the moisture sensor is upstream of the inlet. In some embodiments, the predetermined moisture content of the cellulosic fiber feedstock is from 45 to 55 wt %.

An advantage of this process is that the temperature of the feedstock may be kept sufficiently low to prevent charring of the fibers. Charring of the fibers results in degradation of the sugars in the cellulose and hemicellulose. This degradation reduces the percentage of sugars that may be liberated for fermentation, thereby decreasing the possible yield of the process. Further, the degradation may produce by products that are undesirable in downstream process streams. Charring may be reduced or prevented by using a lower temperature water supply to the heating jacket of the treatment chamber, a lower temperature of the water that is used to provide moisture and/or by avoiding fibers being retained too long in contact with a heated wall of the treatment chamber. For example, if steam is not used to provide moisture to the fibers in the treatment chamber, but water at, e.g., 50-60° C. is used, the feedstock will be heated but will not be raised to a temperature at which degradation may occur.

A feedstock having a moisture content from about 30 to about 60 wt % may be prepared by obtaining relatively dry plant material which is broken down into small chips, e.g., from about 0.05 to about 2 inches, and then combining the chips with water (e.g., steam and/or a fine mist spray, or droplets of water of between 600 μm and 6000 μm in diameter). This material may then be transported to a hydrolysis or autohydrolysis reactor, and preferably is subjected to autohydrolysis and then subsequently enzymatic hydrolysis. This material is difficult to transport as the material is essentially a solid (having insufficient water to form even a slurry). Accordingly, the material has a tendency to interlock and may result in process vessels or flow passages between equipment becoming blocked. Also, since this material is essentially discrete blocks of material (e.g., wood chips), the gaps between the blocks are filled with air. Accordingly, the mass and heat transfer characteristics of this material result in it being difficult to obtain a relatively uniform distribution of heat and moisture in the material. This lack of uniformity can result in decreased yield and/or contamination during downstream autohydrolysis or enzymatic hydrolysis.

Embodiments of the present invention provide a method and apparatus for conveying a cellulosic feedstock. The method and apparatus relate to a holding tank that can be positioned downstream from a cellulosic feedstock pre-treatment process, preferably an impregnation process wherein moisture is added to the feedstock but the feedstock is not converted to a slurry, that can be utilized to further prepare the cellulosic feedstock for subsequent production of a sugar stream, which is preferably fermented to produce alcohol. Preferably, the feedstock is subsequently subjected to a hydrolysis process. The hydrolysis process may be autohydrolysis and, more preferably, comprises autohydrolysis followed by enzymatic hydrolysis.

In one broad aspect, a method for preparing a cellulosic feedstock for subsequent ethanol production is provided. The method comprises obtaining a cellulosic feedstock having a moisture content of 30 wt % to 60 wt %; passing the cellulosic feedstock through a heated holding tank; withdrawing the cellulosic feedstock from the holding tank; and, subsequently subjecting the cellulosic feedstock to hydrolysis.

In various embodiments, a method for preparing a cellulosic feedstock is provided which comprises (a) obtaining an acid-impregnated feedstock; (b) passing the cellulosic feedstock through a holding tank; (c) withdrawing the cellulosic feedstock from the holding tank; and, (d) subsequently subjecting the cellulosic feedstock to hydrolysis.

In still other embodiments, a method for preparing a cellulosic feedstock is provided which comprises (a) passing an acid-impregnated cellulosic feedstock through a holding tank; (b) withdrawing the acid-impregnated cellulosic feedstock from the holding tank; and, (c) subsequently subjecting the acid-impregnated cellulosic feedstock to hydrolysis.

In some embodiments, the moisture content of the cellulosic feedstock is between 45% and 55%.

In some embodiments, the step of passing the cellulosic feedstock through a heated holding tank comprises passing the cellulosic feedstock downwardly through the heated holding tank. In further embodiments, the cellulosic feedstock is passed downwardly through the heated holding tank under the force of gravity.

In some embodiments, the cellulosic feedstock has a residence time of up to 60 minutes in the heated holding tank. In some further embodiments, the cellulosic feedstock has a residence time of between 5 minutes and 45 minutes in the heated holding tank. In yet further embodiments, the cellulosic feedstock has a residence time of between 10 minutes and 30 minutes in the heated holding tank.

In some embodiments, the heated holding tank is heated by passing a heated fluid through a heating jacket provided on at least a portion of the heated holding tank.

In some embodiments, the cellulosic feedstock enters the heated holding tank at a temperature of between 50° C. and 70° C. In some further embodiments, the cellulosic feedstock enters the heated holding tank at a temperature between 50° C. and 65° C.

In some embodiments, the method further comprises maintaining the cellulosic feedstock at a temperature of between 50° C. and 70° C. while in the heated holding tank. In alternate embodiments, the cellulosic feedstock enters the heated holding tank at a first temperature, and exits the heated holding tank at a second temperature higher than the first temperature. In some such embodiments, the first temperature is below 50° C., and the second temperature is between 50° C. and 70° C.

In some embodiments, the heated holding tank has a lower open end, and the step of withdrawing the cellulosic feedstock from the holding tank comprises withdrawing cellulosic feedstock from essentially the entirety of the lower open end.

In some embodiments, the method further comprises monitoring a temperature of the cellulosic material in the heated holding tank. In some further embodiments, the method comprises adjusting an amount of heat applied to the heated holding tank based on the temperature of the cellulosic material in the holding tank.

In some embodiments, the method comprises obtaining the cellulosic feedstock from a water impregnation reactor.

In accordance with another broad aspect, holding tank apparatus for preparing a cellulosic feedstock, moisture-impregnated cellulosic feedstock, and/or an acid-impregnated cellulosic feedstock are provided. The holding tank apparatus comprises at least one sidewall defining a passage having an upper portion and a lower portion. At least one inlet is provided adjacent the upper portion, wherein, in use, the inlet is in fluid communication with a water impregnation reactor provided upstream from the holding tank. At least one outlet is provided adjacent the lower portion, wherein, in use, the outlet is in fluid communication with hydrolysis reactor positioned downstream from the holding tank. At least one conveyor is positioned adjacent to at least one outlet. A heating jacket is provided on at least a portion of the apparatus.

In some embodiments, the heating jacket is provided on the sidewalls of the holding tank.

In some embodiments, the at least one conveyor conveys the cellulosic feedstock laterally across the outlet. Preferably, the outlet extends across the lower portion of the passage. In some further embodiments, the holding tank has a longitudinal axis, and each of the at least one conveyors comprises a screw conveyor extending transversely to the longitudinal axis and provided in a housing positioned adjacent the outlet, and the housing comprises a second heating jacket.

In some embodiments, the holding tank is operable to provide a residence time of up to 60 minutes. In some further embodiments, the holding tank is operable to provide a residence time of between 5 minutes and 45 minutes.

In some embodiments, the holding tank has a longitudinal axis and at least one of the at least one sidewalls diverges from the longitudinal axis from the upper portion to the lower portion.

An advantage of this process is that the temperature of the feedstock is maintained at a suitable temperature for feeding to a steam explosion reactor while the temperature may be kept sufficiently low to prevent charring of the fibers. Charring of the fibers results in degradation of the sugars in the cellulose and hemicellulose. This degradation reduces the percentage of sugars that may be liberated for fermentation, thereby decreasing the possible yield of the process. Further, the degradation may produce by-products that are undesirable in downstream process streams. Further additional time may be provided to enhance the uniformity of the water distribution in the fiber chips such that water is available at essentially all sites for hydrolysis.

Accordingly, embodiments of the present invention relate to a cellulosic feedstock pre-treatment process, which comprises the addition of moisture to a cellulosic feedstock to prepare the feedstock for pre treatment (i.e. autohydrolysis). More specifically, embodiments of the present invention involve determining an amount of moisture to be added to a cellulosic feedstock to obtain a predetermined moisture content in the cellulosic feedstock that may then be subjected to an autohydrolysis reaction and a subsequent steam explosion.

In one broad aspect, a method is provided for treating a cellulosic feedstock, such as for subsequent ethanol production. The method comprises determining an initial moisture content of the cellulosic feedstock; adding an amount of moisture to the cellulosic feedstock to obtain a predetermined moisture content of the cellulosic feedstock; and subsequently subjecting the cellulosic feedstock to hydrolysis, preferably autohydrolysis followed by enzymatic hydrolysis.

Embodiments in accordance with this broad aspect may be advantageous because the moisture content of the cellulosic feedstock may be monitored and controlled to prevent the feedstock having an excess of moisture, which may result in an incomplete autohydrolysis and/or accumulation of degraded sugars in the reactor or an insufficient amount of water that will hinder activation and may result in a portion of the cellulosic feedstock not having the water molecule present for the autohydrolysis reaction to occur. In various embodiments, the method for treating a cellulosic feedstock comprises a) intermittently determining an initial moisture content of the cellulosic feedstock; b) adding an amount of moisture to the cellulosic feedstock to obtain a predetermined moisture content of the cellulosic feedstock; and, c) subsequently subjecting the cellulosic feedstock to hydrolysis, wherein steps b) and c) are conducted automatically.

In some embodiments, the step of adding an amount of moisture to the cellulosic feedstock comprises determining the amount of moisture required to obtain the predetermined moisture content based on the weight of the cellulosic feedstock and the initial moisture content of the cellulosic feedstock, and adding the amount of moisture.

In some embodiments, the steps of determining the initial moisture content and adding the amount of moisture are performed automatically and/or continuously.

In other embodiments, the method for treating a cellulosic feedstock comprises a) determining an initial moisture content of the cellulosic feedstock; b) determining an initial mass of the cellulosic feedstock; and c) adding an amount of an acidic liquid medium having a predetermined acid concentration to the cellulosic feedstock to obtain an acid-impregnated cellulosic feedstock having a predetermined moisture content and acid content.

In various embodiments, the method for treating a cellulosic feedstock, the method comprises a) determining an initial moisture content of the cellulosic feedstock; b) introducing the cellulosic feedstock into a treatment vessel; c) determining the mass feed rate of the cellulosic feedstock into the treatment vessel; and d) introducing an acidic liquid medium having a predetermined acid concentration into the treatment vessel at a predetermined rate to provide an acid-impregnated cellulosic feedstock having a predetermined moisture content and acid content.

In some embodiments, the initial moisture content is less than 15 wt % based on the total weight of the cellulosic feedstock. In further embodiments, the predetermined moisture content is about 30 to 60 wt % based on the total weight of the cellulosic feedstock.

In some embodiments, the method further comprises determining a weight of the cellulosic feedstock as the cellulosic feedstock is conveyed to a mixing vessel.

In some embodiments, the method further comprises conveying the cellulosic feedstock through a mixing vessel, and adding at least a portion of the amount of moisture to the cellulosic feedstock while the cellulosic feedstock is conveyed through the mixing vessel.

In some embodiments, the method further comprises adding moisture to the cellulosic feedstock through multiple inlet ports provided on the mixing vessel.

In some embodiments, the method further comprises completing addition of the amount of moisture prior to conveying the cellulosic feedstock through a downstream portion of the mixing vessel.

In some embodiments, the method further comprises adding at least a portion of the amount of moisture prior to conveying the cellulosic feedstock through a mixing vessel.

In some embodiments, the method further comprises passing the cellulosic feedstock downwardly into the mixing vessel while exposing the cellulosic feedstock to droplets of water of between 600μ and 6000μ in diameter.

In some embodiments, the method further comprises heating the cellulosic feedstock while conveying the cellulosic feedstock through a mixing vessel, and completing addition of the amount of moisture prior to conveying the cellulosic feedstock through a downstream portion of the mixing vessel, wherein the cellulosic feedstock has a temperature less then 50° C. prior to entering the mixing vessel and a temperature from 50° C. to 70° C. after exiting the mixing vessel.

In some embodiments, the method further comprises adding a hydrolysis catalyst with the moisture.

In some embodiments, the cellulosic feedstock is heated while the amount of moisture is added.

In some embodiments, the initial moisture content of each segment of cellulosic feedstock is determined and the amount of moisture to obtain a predetermined moisture content is provided to that segment of the cellulosic feedstock.

In another broad aspect, a cellulosic feedstock treatment apparatus is provided. The apparatus comprises a moisture sensor that provides an output value corresponding to an initial moisture content of the cellulosic feedstock. The apparatus further comprises a weight scale that provides an output value corresponding to a weight of the cellulosic feedstock. A processor is coupled to the moisture sensor and the weight sensor. The processor is configured to determine an amount of moisture to be added to the cellulosic feedstock based on the weight of the cellulosic feedstock and the initial moisture content of the cellulosic feedstock to obtain treated cellulosic feedstock having a predetermined moisture content. A mixing vessel is provided downstream from the weight sensor. In various embodiments, the cellulosic feedstock treatment apparatus comprises a) a moisture sensor adapted for intermittently providing an output value corresponding to an initial moisture content of the cellulosic feedstock; b) a weight sensor providing an output value corresponding to a weight of the cellulosic feedstock; c) a processor coupled to the moisture sensor and the weight sensor, the processor being configured to determine an amount of moisture to be added to the cellulosic feedstock based on the weight of the cellulosic feedstock and the initial moisture content of the cellulosic feedstock to obtain treated cellulosic feedstock having a predetermined moisture content; and, d) a mixing vessel downstream from the weight sensor.

In some embodiments, the weight sensor comprises a weighing conveyor.

In some embodiments, the mixing vessel comprises a longitudinally extending volume having an inlet, an opposed outlet, and a conveyance member positioned inside the volume.

In some embodiments, the apparatus comprises a passage extending from the weight sensor to the inlet wherein at least a portion of the passage extends downwardly. In further embodiments, the portion comprises at least one moisture injection port. In some embodiments, at least one moisture injection port is configured to provide discrete droplets of water of between 600μ and 6000μ in diameter.

In some embodiments, an upstream portion of the mixing vessel has multiple water injection ports. In further embodiments, a downstream portion of the mixing vessel has an absence of water injection ports.

In some embodiments, the mixing vessel has a heating jacket.

In some embodiments, the apparatus comprises a downstream autohydrolysis reactor.

In some embodiments, the processor provides a signal to at least one moisture addition member and the signal is lagged by an amount of time corresponding to the time for a segment of cellulosic feedstock to travel from the moisture sensor to a moisture addition zone containing the at least one moisture addition member.

In some embodiments the conveyance member comprises paddles (or flights) mounted on a shaft wherein steam may flow through the paddles and or shaft. Accordingly, the feedstock may be indirectly heated by the paddles and/or shaft. Alternately, moisture injection ports may be provided in the shaft and/or paddles.

Embodiments of the present invention provide a method and apparatus for withdrawing a cellulosic feedstock from a vessel by actively withdrawing feedstock from different portions of the outlet of a vessel and, preferably, withdrawing a feedstock evenly from across the outlet. An advantage of this design is that a generally uniform residence time of the feedstock in the vessel may be achieved. For example, the variance of the residence time may be up to 5 minutes, preferably, less than 3 minutes and more preferably less than 2 minutes. Accordingly, the tendency of the portion of a feedstock that is adjacent a heated surface in the vessel, such as a surface in thermal contact with a heating jacket, to be degraded by overheating may be reduced and, preferably, eliminated.

Alternately, or in addition, embodiments of the present invention provide a method and apparatus for withdrawing a cellulosic feedstock from a vessel in a direction transverse to the direction of travel of the material through the vessel. Accordingly, if the vessel is oriented such that they passage therethrough is generally vertical, the feedstock is withdrawn generally horizontally. A plurality of feedstock streams, each of which may be conveyed in a different direction may be obtained.

According to a first broad aspect, holding tank apparatus for preparing a cellulosic feedstock, moisture-impregnated cellulosic feedstock, and/or an acid-impregnated cellulosic feedstock are provided. The holding tank apparatus comprises at least one sidewall defining a volume having an upper portion and a lower portion. At least one inlet is provided adjacent the upper portion, and at least one outlet is provided adjacent the lower portion, at an elevation below the inlet. At least one screw conveyor is provided for conveying the cellulosic feedstock laterally across the outlet. The at least one screw conveyor has a variable pitch along its length. Providing the at least one screw conveyor with a variable pitch along its length may allow for a generally equal amount of cellulosic feedstock to be withdrawn from all portions of the outlet.

In some embodiments, the at least one screw conveyor has a first end and a second end, and the pitch at the first end differs from the pitch at the second end. In some further embodiments, the at least one screw conveyor comprises a first region having a first range of pitch, and a second region having a second range of pitch. In yet further embodiments, the at least one screw conveyor comprises an intermediate region between the first region and the second region, and the intermediate region has a third range of pitch between the first range of pitch and the second range of pitch.

In some embodiments, the at least one screw conveyor has a first end and a second end, and the pitch decreases from the first end to the second end and, preferably, varies at a constant rate between the first end and the second end.

In some embodiments, the outlet defines a plurality of portions and the pitch varies such that approximate equal portions of feedstock are withdrawn from each portion of the outlet.

In some embodiments, the at least one screw conveyor comprises a plurality of screw conveyors and at least one of the screw conveyors conveys the cellulosic feedstock in a first direction and at least one of the screw conveyors conveys the cellulosic feedstock in a second direction. In a further embodiment, the first direction and the second direction are substantially opposite.

In some embodiments, the at least one screw conveyor comprises a plurality of screw conveyors and at least two adjacent two screw conveyors have a length and convey the cellulosic feedstock in a first direction and the pitch of the screw conveyors at any location along the length of the screw conveyors is essentially the same.

In some embodiments, the apparatus comprises a plurality of screw conveyors having a length, and a first pair of the screw conveyors conveys cellulosic feedstock in the first direction, and a second pair of the screw conveyors conveys cellulosic feedstock in the second direction.

In some such embodiments, the pitch of the first pair of screw conveyors at any location along the length is essentially the same and the pitch of the second pair of screw conveyors at any location along the length is essentially the same. In some further embodiments, the first pair of screw conveyors conveys cellulosic feedstock in the first direction, and the second pair of screw conveyors conveys the cellulosic feedstock in a second direction opposite to the first direct, and the pitch of the first pair of screw conveyors is a mirror image of the pitch of the second pair of the screw conveyors.

In some embodiments, the first pair of screw conveyors is rotatable in a first direction, and the second pair of screw conveyors is rotatable in a second direction opposite to the first direction.

In some embodiments the at least one screw conveyor extends across all of the outlet.

In some embodiments, the apparatus further comprises a heating jacket provided on at least a portion of the apparatus. Such embodiments may be advantageous because the heating jacket may elevate or maintain the temperature of the cellulosic feedstock, which may render the cellulosic feedstock further accessible to auto hydrolysis, preferably followed by enzymes hydrolysis.

In some embodiments, the lower portion of the holding tank has a greater cross sectional area then the upper portion of the holding tank. Such embodiments may be advantageous because cellulosic material may be prevented from adhering or sticking to the sidewalls as the cellulosic material passes through the holding tank. Accordingly, each portion of cellulosic feedstock that passes through the holding tank may have essentially the same residence time in the volume.

In some embodiments, the sidewalls comprise a first sidewall and a second sidewall opposed to the first sidewall, and the first and second sidewalls diverge relative to each other from the upper portion to the lower portion.

In some embodiments, the sidewalls comprise a third sidewall and a fourth sidewall opposed to the third sidewall, and the third and fourth sidewalls extend between the first and second sidewalls, and the third and fourth sidewalls diverge relative to each other from the upper portion to the lower portion.

In another broad aspect, a method of preparing a cellulosic feedstock for ethanol production is provided. The method comprises passing the cellulosic feedstock through an impregnation chamber to an outlet of the impregnation chamber; passing the cellulosic feedstock from the outlet of the impregnation chamber to an inlet of a holding tank, the holding tank having an outlet; passing the cellulosic feedstock downwardly through the holding tank; maintaining a generally constant residence time in the holding tank; and subsequently subjecting the cellulosic feedstock to a downstream hydrolysis process.

In various embodiments, the method comprises passing the cellulosic feedstock through an impregnation chamber to an outlet of the impregnation chamber; passing the cellulosic feedstock from the outlet of the impregnation chamber to an inlet of a holding tank, the holding tank having an outlet; passing the cellulosic feedstock downwardly through the holding tank; maintaining a generally constant average residence time in the holding tank; and subsequently subjecting the cellulosic feedstock to a downstream hydrolysis process.

In some embodiments, the method further comprises maintaining a temperature in the holding tank between about 50° Celsius and about 75° Celsius.

In some embodiments, the method further comprises maintaining a variance of the residence time of each portion of the amount of up to 5 minutes.

In some embodiments, the method further comprises maintaining a residence time in the holding tank from about 10 to about 45 minutes.

In some embodiments, the method further comprises conveying the cellulosic feedstock laterally across an outlet of the holding tank. In some such embodiments, the cellulosic feedstock is actively withdrawn from essentially the entirety of the outlet. Further, in some such embodiments a generally equal amount of cellulosic feedstock is withdrawn from each portion of the outlet. Further, in some such embodiments, the cellulosic feedstock is conveyed in at least two different lateral directions.

In some embodiments, a screw conveyor having different pitches is utilized to convey the cellulosic feedstock laterally across the outlet of the holding tank.

Embodiments of the present invention provide a method and apparatus for preparing a cellulosic feedstock for ethanol production. The method and apparatus relate to an apparatus, such as a holding tank, that may be positioned downstream from a cellulosic feedstock pre-treatment process, such as a mixing vessel that impregnates the cellulosic feedstock with heat and moisture, and upstream from hydrolysis reactors, such as an autohydrolysis reactor.

Further, embodiments in accordance with this invention may be advantageous because obtaining two streams and feeding the two streams into different hydrolysis reactors allows for the hydrolysis reactors to be operated on a batch basis and to be operated such that at least one hydrolysis reactor is out of phase with another hydrolysis reactor. That is, a first hydrolysis reactor may be filled from a first stream while a second hydrolysis reactor is operated to hydrolyze a cellulosic feedstock obtained from a second stream. Accordingly, the overall process may be a continuous process, while the hydrolysis process may be operated on a batch process.

As the material is transported to one or more process units (e.g., hydrolysis units) wherein the feedstock will be broken down, such as in the preparation of a fermentable sugar stream, the material preferably travels downward through a vessel or conduit from which it must then be withdrawn. For example, the material may be passed through a hopper, a holding tank with a bottom outlet, a process vessel with a bottom outlet or the like and, preferably a holding tank. As the material is preferably substantially a solid, it does not flow freely. Therefore, while the material may travel downwardly under the influence of gravity, not all portions will travel downwardly at the same rate. The portions closer to the wall of a vessel may have a tendency to stick to the sidewall or travel downwardly slower due to friction between the sidewall and the material adjacent the sidewall. This may result in different residence times for some portions of the feedstock. If the sidewall is heated (e.g. surrounded by a heating jacket), portions of the material closer to the sidewall may overheat if the residence time is too long, causing sugar in the feedstock to degrade. Accordingly, it is preferred that the feedstock is actively withdrawn from such equipment to obtain the multiple process streams.

In accordance with one aspect of the instant invention, there is provided a method of preparing a cellulosic feedstock for ethanol production, comprising: (a) passing the cellulosic feedstock through a vessel to at least one outlet of the vessel; (b) passing the cellulosic feedstock out of the at least one outlet of the vessel and obtaining at least two streams of cellulosic feedstock; and, (c) feeding the at least two streams to different hydrolysis reactors.

In any embodiment, step (b) may comprise conveying the cellulosic feedstock laterally across the outlet of the vessel, preferably in different directions.

In any embodiment, the method may further comprise operating the different hydrolysis reactors on a batch basis and operating at least one hydrolysis reactor out of phase with another hydrolysis reactor. Preferably, a first hydrolysis reactor is filled from a first stream while a second hydrolysis reactor is operated to hydrolyze cellulosic feedstock obtained from a second stream.

In any embodiment, the method may further comprise passing the cellulosic feedstock downwardly through the vessel.

In any embodiment, the vessel may comprise at least four conveying devices proximate the at least one outlet of the vessel, and step (b) may comprise utilizing at least two conveying devices to convey a first portion of the cellulosic feedstock in a first direction to obtain the first stream, and utilizing at least two conveying devices to convey a second portion of the cellulosic feedstock in a second direction to obtain the second stream. Preferably, a first portion of cellulosic feedstock for the first stream is drawn from a first portion of the outlet and a second portion of cellulosic feedstock for the second stream is drawn from a second portion of the outlet. For example, the first portion may comprise one side of the outlet and the second portion may comprise a second side of the outlet (e.g., the outlet may be essentially divided in half with each side comprising a portion). In such a case, two conveying devices that operate to withdrawn the feedstock to form a first steam may be positioned under one side and two conveying devices that operate to withdrawn the feedstock to form a second steam may be positioned under the other side.

In any embodiment, the at least one inlet of the vessel is preferably disposed at an elevation above the at least one outlet of the vessel, and the cellulosic feedstock is preferably conveyed from the at least one inlet towards the at least one outlet of the vessel under the force of gravity.

In any embodiment, the residence time of the cellulosic in the vessel is preferably up to 60 minutes, and, more preferably between 10 minutes and 30 minutes.

In any embodiment, the method may further comprise applying heat to the cellulosic feedstock in the vessel.

In any embodiment, steps (a) to (c) are preferably performed on a continuous basis.

It will be appreciated that, in any embodiment, the cellulosic feedstock conveyed through the vessel is a solid and may be of any composition disclosed herein.

In accordance with another aspect of the instant invention, there is also provided an apparatus for use in preparing a cellulosic feedstock, moisture-impregnated cellulosic feedstock, and/or an acid-impregnated cellulosic feedstock for ethanol production, comprising: (a) at least one sidewall defining a volume having an upper portion and a lower portion; (b) at least one inlet adjacent the upper portion; (c) at least one outlet adjacent the lower portion; (d) at least a first conveyor proximate the at least one outlet configured to convey a first portion of the cellulosic feedstock laterally across the at least one outlet in a first direction; and, (e) at least a second conveyor proximate the at least one outlet configured to convey a second portion of the cellulosic feedstock laterally across the at least one outlet in a second direction.

In any embodiment, the first and second conveyors are preferably positioned adjacent each other.

In any embodiment, the first conveyor preferably conveys cellulosic feedstock towards an outlet of the first conveyor, and the second conveyor preferably conveys cellulosic feedstock towards an outlet of the second conveyor.

In any embodiment, the first direction is preferably generally opposite to the second direction.

In any embodiment, all of the outlet is preferably exposed to the conveyors.

In any embodiment, the conveyors may be provided in a housing having at least one conveyor outlet in a lower surface thereof for each conveyor.

In any embodiment, each conveyor may comprise at least one rotatably mounted helical screw, and preferably at least two helical screws that are rotatable in the same direction. Alternately, or in addition, in any embodiment, one or more, and preferably each conveyor comprises at least one rotatably mounted helical screw having a variable pitch.

In any embodiment, the apparatus may further comprise a housing for the conveyors and a heating jacket disposed at least partially around the housing.

In accordance with another aspect of the instant invention, there is also provided an apparatus for use in preparing a cellulosic feedstock for ethanol production comprising (a) at least one sidewall defining a volume having an upper portion and a lower portion; (b) at least one inlet adjacent the upper portion; (c) at least one outlet adjacent the lower portion; (d) at least one discharge member below the outlet, the discharge member comprising one or more screw conveyors, one or more paddle conveyors, one or more sweeping conveyors, one or more sweeping arms, one or more rotational disks, or one or more metering screws.

It will be appreciated that each of the embodiments may be used by itself in the method or aspect provided in accordance with this invention. It will further be appreciated that each of the embodiments may be used with any other embodiments or embodiments such that the embodiments may be used individually or all together in combination or in any sub-combination.

BRIEF DESCRIPTION OF THE DRAWINGS

FIG. 17A is a perspective illustration of an embodiment of a paddle of the present invention;

FIG. 17B is a front plan view of the paddle of FIG. 17A;

FIG. 17C is a side plan view of the paddle of FIG. 17A;

FIG. 17D is a top plan view of the paddle of FIG. 17B;

FIG. 18A is a partial perspective illustration of an embodiment of a conveyance member of the present invention, wherein the paddle of the conveyance member comprises injection ports;

FIG. 18B is a partial front plan view of the paddle of FIG. 18A;

FIG. 18C is a partial side plan view of the paddle of FIG. 18A;

FIG. 18D is a transverse cross-section taken along line D-D in FIG. 18A;

FIG. 25A is a perspective illustration of an embodiment of a paddle of the present invention;

FIG. 25B is a front plan view of the paddle of FIG. 25A;

FIG. 25C is a side plan view of the paddle of FIG. 25A;

FIG. 25D is a top plan view of the paddle of FIG. 25B;

FIG. 26A is a partial perspective illustration of an embodiment of a conveyance member of the present invention, wherein the paddle of the conveyance member comprises injection ports;

FIG. 26B is a partial front plan view of the paddle of FIG. 26A;

FIG. 26C is a partial side plan view of the paddle of FIG. 26A;

FIG. 26D is a transverse cross-section taken along line D-D in FIG. 26A;

FIG. 33A is a partial perspective illustration of the conveyance member shown in FIG. 31, wherein the conveyance member optionally includes paddles having moisture injection ports;

FIG. 33B is a partial front plan view of the paddle shown in FIG. 33A;

FIG. 33C is a side plan view of the paddle shown in FIG. 33A;

FIG. 33D is a longitudinal cross-section taken along line D-D in FIG. 33A; and,

DETAILED DESCRIPTION OF THE PREFERRED EMBODIMENTS

Figure 1:
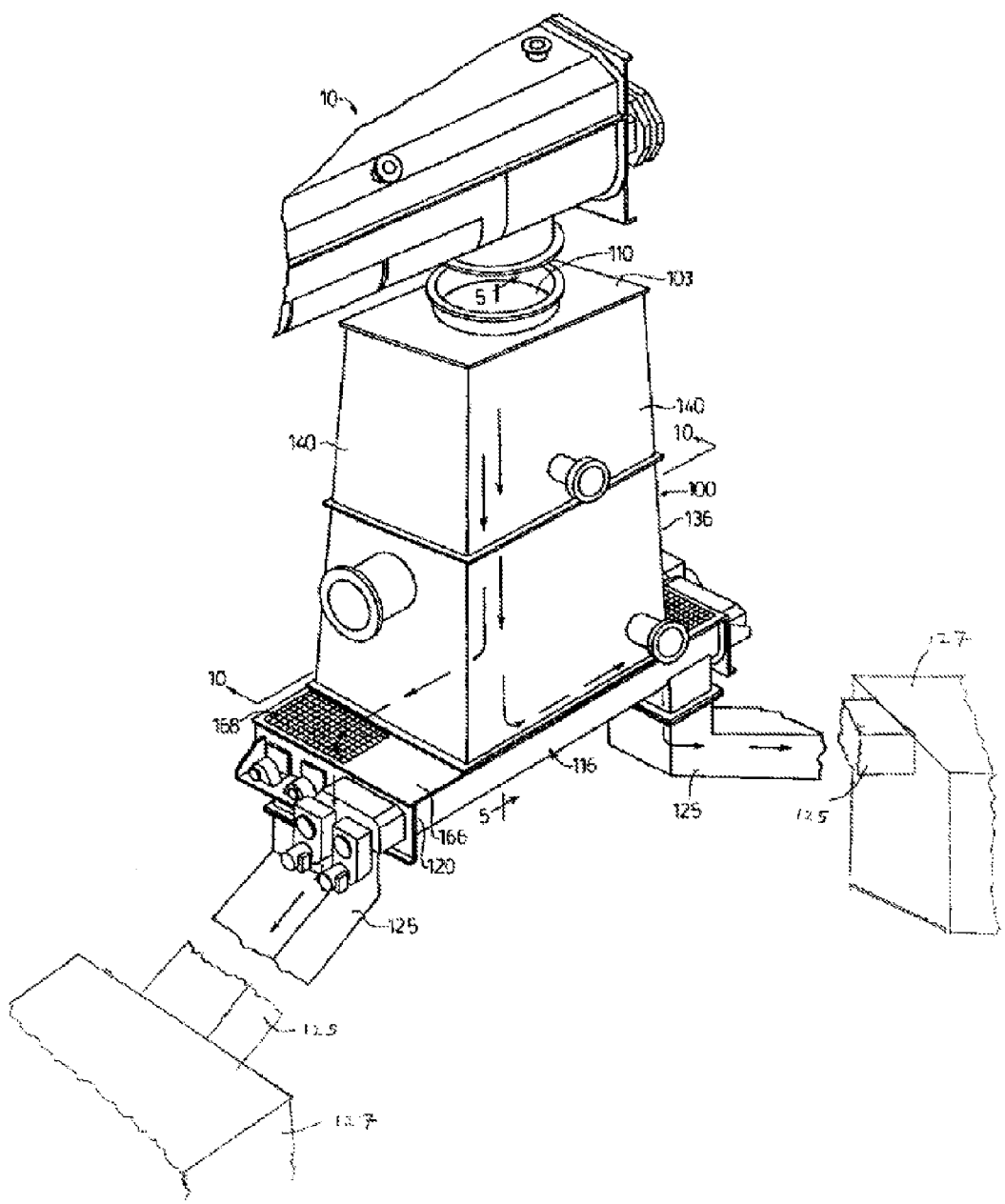
FIG. 1 is a perspective illustration of an embodiment of a holding tank of the present invention, showing an impregnation chamber positioned upstream from the holding tank.

The cellulosic feedstock is preferably a lignocellulosic feedstock. A lignocellulosic feedstock is derived from plant materials. As used herein, a "lignocellulosic feedstock" refers to plant fiber containing cellulose, hemicellulose and lignin. Generally, the feedstock comprises woody and/or non-woody cellulosic biomass provided by, for example, plant biomass, agricultural wastes, forestry residues, and sugar processing residues. In some embodiments, the feedstock may be derived from trees, preferably deciduous trees such as poplar (e.g., wood chips). In particular, the feedstock may also include wood and forestry wastes such as, for example, recycled wood pulp fiber, sawdust, hardwood, softwood, forest thinnings, orchard thinnings, or combinations thereof. Accordingly, in various embodiments, the feedstock comprises a woody biomass. Alternately or in addition, the feedstock may also be derived from agricultural residues such as, but not limited to corn stover, wheat straw, barley straw, rice straw, switchgrass, sorghum, bagasse, rice hulls, corn cobs, canola straw, oat straw, oat hulls, corn fiber, sorghum stover, soybean stover and combinations thereof. Preferably, the lignocellulosic feedstock comprises agricultural residues and wood biomass, more preferably wood biomass and most preferably deciduous. The feedstock may also comprise grasses, such as cord grass, rye grass, reed canary grass, miscanthus, or combinations thereof. Suitable sugar-processing residues include, for example, sugar cane bagasse, sweet sorghum, beet pulp, and combinations thereof. The applicants contemplate other sources of plant materials comprising cellulose, hemicellulose and/or lignin, such as algae, for use in deriving cellulosic feedstocks and any of those may be used.

In various preferred embodiments the feedstock comprises a non-woody biomass selected from the group consisting of corn stover, wheat straw, barley straw, sorghum, switchgrass, miscanthus, and combinations thereof. In various other preferred embodiments, the feedstock comprises corn stover, wheat straw, oat straw, barley straw, switchgrass, hardwood, and combinations thereof. In particular preferred embodiments, the feedstock comprises corn stover. In these and various other preferred embodiments, the feedstock comprises wheat straw. Still further, in these and various other preferred embodiments, the feedstock comprises switchgrass.

The lignocellulosic feedstock is preferably cleaned, e.g., to remove ash, silica, metal strapping (e.g., from agricultural products), stones and dirt. The size of the components of the lignocellulosic feedstock may also be reduced. The size of the components of the feedstock may be from about 0.05 to about 2 inches, preferably from about 0.1 to about 1 inch, and more preferably from about 0.125 to about 0.5 inches in length. For example, the cellulosic feedstock may comprise fibers, e.g., chopped straw, of a length of between about 0.16 inches and about 0.28 inches. Any process machinery that is able to crush, grind or otherwise decrease the particle size may be utilized.

I.

Embodiments of the present invention provide methods and apparatus for treating a cellulosic feedstock for subsequent ethanol production. The methods and apparatus of preferred embodiments serve to heat or maintain the temperature of the cellulosic feedstock to obtain a relatively uniform temperature and moisture level of the feedstock, while reducing, and preferably essentially preventing, the charring or other degradation of the cellulose and hemicellulose during this stage. Accordingly, the methods and apparatus provide a cellulosic feedstock which is suitable for the production of a fermentation precursor stream. The cellulosic feedstock may be subsequently treated to liberate sugars in the cellulose and hemicellulose and produce a sugar stream that may then be subjected to fermentation to obtain a high yield alcohol stream. Embodiments of apparatus of the present invention are shown in FIGS. 1-10. It will be appreciated that although the methods are described with reference to the apparatus and vice versa, the methods may be carried out with alternate apparatus, and the apparatus may be used according to alternate methods. Furthermore, although the methods are described as continuous processes, it will be appreciated that the methods may be carried out as a semi-continuous or batch processes.

Embodiments of the present invention provide enhanced uniformity of residence time of the feedstock in a holding tank. In particular, despite withdrawing the feedstock laterally with respect to the direction of flow through the holding tank, a generally uniform residence time for all portions of the feedstock that are concurrently withdrawn from the holding tank may be obtained.

The feedstock is preferably treated with water so as to have a moisture content upon entry to holding tank 100 of between about 30 and about 60 wt. %, preferably between about 45 and about 55 wt %. For example, referring to FIGS. 1 and 2, an embodiment of a holding tank apparatus 100 of the present invention is shown wherein the holding tank 100 is positioned downstream from a water impregnation reactor such as impregnation chamber 10, which is preferably used to pre-treat the feedstock prior to the feedstock entering holding tank 100. Impregnation chamber 10 is preferably configured to pre-treat the cellulosic feedstock, for example by moistening and/or heating the cellulosic feedstock.

Figure 2:
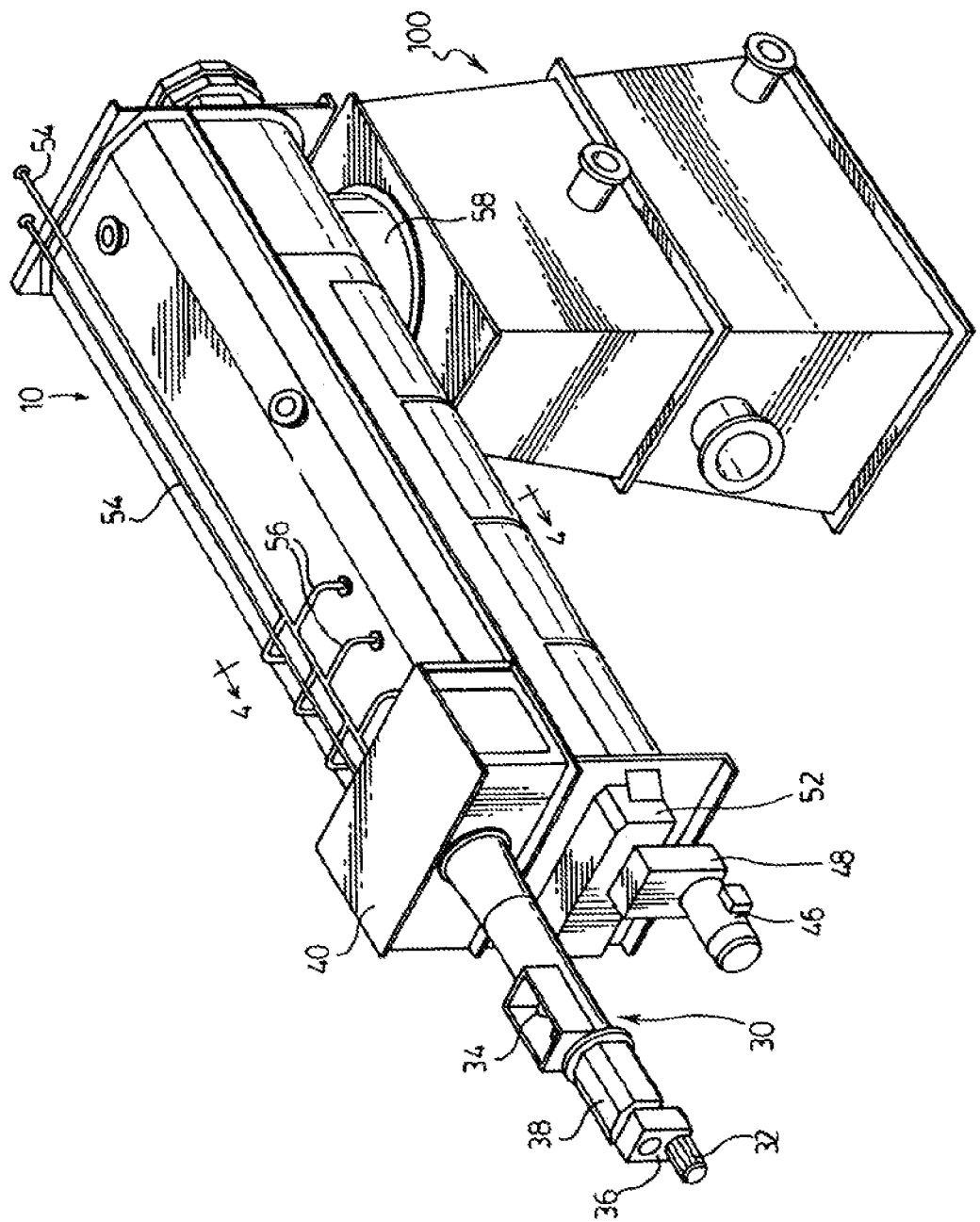
FIG. 2 is a perspective illustration of the impregnation chamber of FIG. 1.
Figure 3:
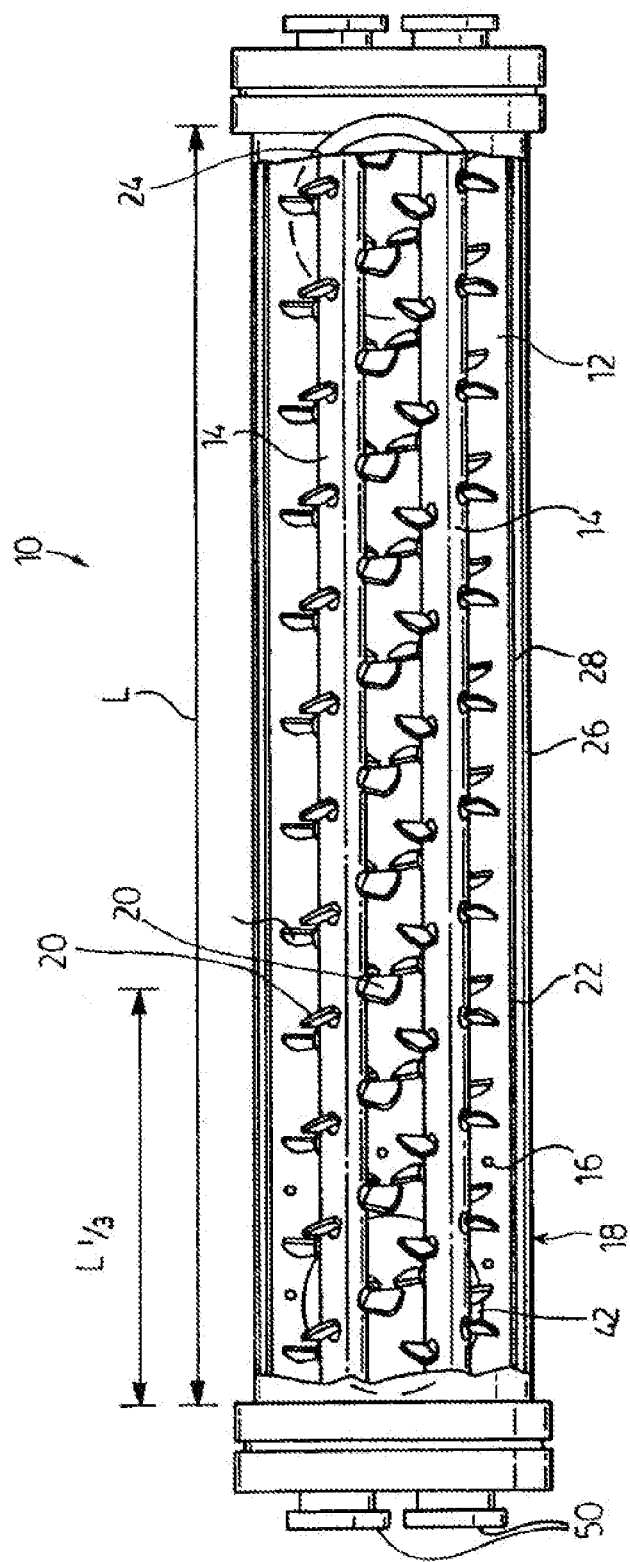
FIG. 3 is a top cutaway view of the impregnation chamber of FIG. 1.
Figure 4:
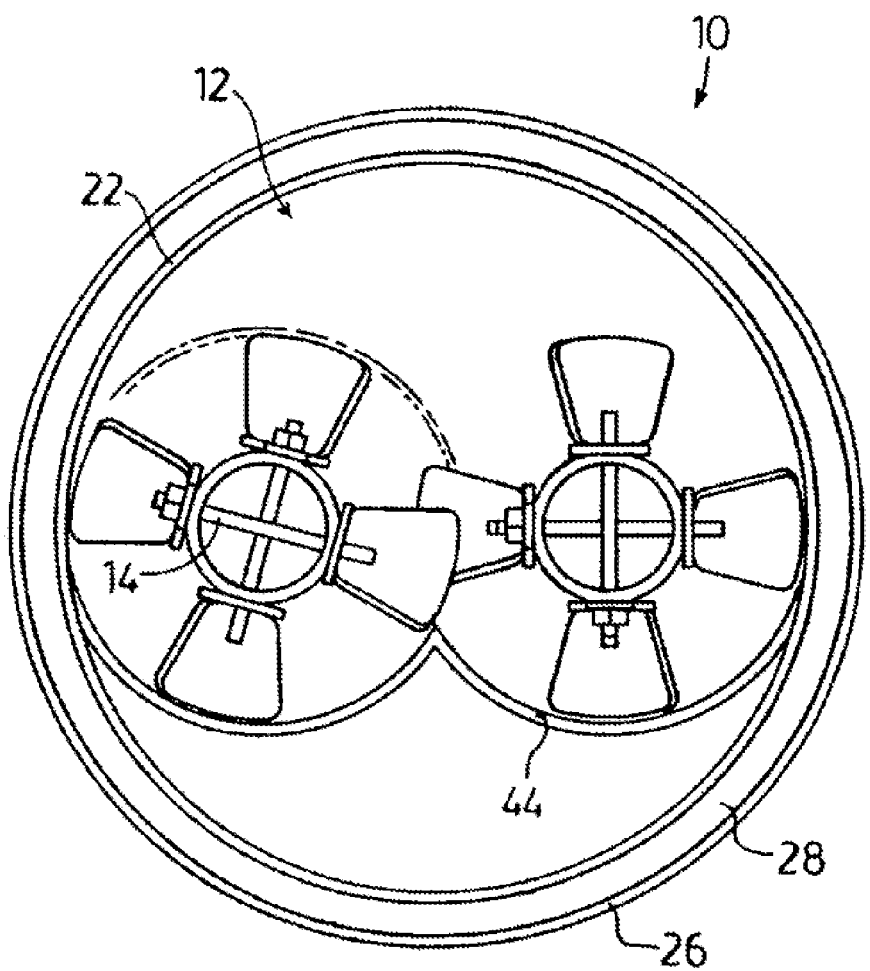
FIG. 4 is a cross section taken along line 4-4 in FIG. 2.

A preferred impregnator 10 is exemplified in FIGS. 2-4. As shown therein, in some embodiments, an impregnator feeder 30, namely a feeder that conveys feedstock into impregnation chamber 12, is preferably positioned upstream of mixing or impregnation chamber 12. Feeder 30 may be of any design. Preferably, feeder 30 is of a design that inhibits, and preferably prevents, the flow of moisture upstream of feeder 30. For example, a rotating valve or the like may be provided to segment such upstream flow. Preferably impregnation feeder is a screw feeder comprising a motor 32 drivingly connected to a screw or auger 34 positioned below an inlet, such as via a transmission or gear reduction assembly provided in housing 36. The shaft on which screw 34 is provided may be rotatably mounted in housing 38 such that auger 34 is a cantilevered plug screw conveyor. Accordingly, feeder 30 produces a plug of material that prevents upstream migration of moisture. The plug may be conveyed into inlet housing 40 that is mounted to impregnation chamber 12. The feedstock may then pass downwardly into impregnation chamber 12.

Impregnator 10 may comprise an inlet 42 positioned below inlet housing 40, one or more conveyance members 14 for urging the cellulosic feedstock along the length of chamber 12, one or more moisture injection ports 16, which may be provided on paddles 20 of conveyance member 14 and/or inner wall 22 of impregnator 10, for injecting moisture into the cellulosic feedstock one or more heating jackets 18 provided outward of inner wall 22 for heating the cellulosic feedstock, and an outlet 24. Heating jacket 18 may comprise an outer wall 26 spaced from inner wall 22 to define a passage 28 through which a heated fluid, e.g. water, may pass.

As exemplified in FIG. 2, one or more conduits 54 may convey water to a plurality of branch conduits 56 extending to different locations on the upper portion of chamber 12. The end of these conduits are in fluid flow communication with the interior of chamber 12, via, e.g., a moisture addition member such as a nozzle or an open ended pipe or the like.

As exemplified, conveyance members 14 are rotatably mounted in chamber 12 and are drivenly connected to a motor 46. As exemplified, motor 46 is drivingly connected to conveyance members 14 via a transmission or gear reduction assembly provided in housing 48. The gear reduction assembly may be drivingly connected to ends 50 of conveyance members 14 that are positioned inside housing 52.

In order to prevent material stagnating in impregnator 10, impregnator 10 may have a bottom wall 44 that has two or more portions each of which has a conveyance member 1 associated therewith. Bottom wall 44 and conveyance member 14 are preferably configured such that bottom wall 44 is swept as conveyance member 14 rotates. For example, as exemplified in FIG. 4, bottom wall 44 may be scallop shaped, e.g., have two inverted arches or troughs. Further details regarding various embodiments of optional impregnation chamber 14 may be found in U.S. patent application Ser. Nos. 12/181,565; 12/181,596; 12/181,640; 12/181,666; 12/181,724 filed on Jul. 29, 2008 and Ser. Nos. 12/361,103 and 12/361,149 filed on Jan. 28, 2009, the entire contents of which are incorporated herein by reference. In alternate embodiments, impregnation chamber 10 may pre-treat the cellulosic feedstock in another manner, and the invention is not limited in this regard.

After the cellulosic feedstock is optionally pre-treated in impregnation chamber 10, it is directed to holding tank apparatus 100, e.g., via outlet passage 58 that is downstream from outlet 24 of chamber 12, where it is held or contained for a residence time, such that for example, moisture added in impregnation chamber 10 has sufficient time to penetrate into the feedstock so that the feedstock is ready for downstream processing. Alternately, or in addition, the feedstock may require additional time for all portions of the feedstock to be raised to a predetermined temperature that is suitable for downstream processing. Alternately, the feedstock entering holding tank 100 may be at the predetermined conditions for downstream processing and holding tank is used as a reservoir to hold prepared feedstock such that downstream processes may operate on a continuous basis. From holding tank 100, the cellulosic feedstock may be directed to one or more hydrolysis reactors, preferably one or more autohydrolysis reactors followed by one or more enzymatic hydrolysis reactors (not shown) positioned downstream from the holding tank apparatus 100, such that the cellulose may be hydrolyzed to produce sugars that are suitable for fermentation to ethanol.

After the cellulosic feedstock is optionally pre-treated in mixing vessel 10, it is directed to holding tank apparatus 100, e.g., via outlet passage 58 that is downstream from outlet 24 of chamber 12, where it is preferably held or contained for a residence time, such that for example, moisture added in mixing vessel 10 has sufficient time to penetrate into the feedstock so that the feedstock is ready for downstream processing. Alternately, or in addition, the feedstock may require additional time for all portions of the feedstock to be raised to a predetermined temperature that is suitable for downstream processing. Alternately, the feedstock entering holding tank 100 may be at the predetermined conditions for downstream processing and holding tank is used as a reservoir to hold prepared feedstock such that downstream processes may operate on a continuous basis.

In accordance with this invention, from a vessel that preferably has a downwardly extending passage for the feedstock (e.g. holding tank 100), the cellulosic feedstock is directed to one or more downstream process units, preferably hydrolysis reactors, more preferably autohydrolysis reactors followed preferably by one or more enzymatic hydrolysis reactors (not shown), positioned downstream from the holding tank apparatus 100 such that the cellulose may be hydrolyzed to produce sugars that are suitable for fermentation to ethanol.

Figure 5:
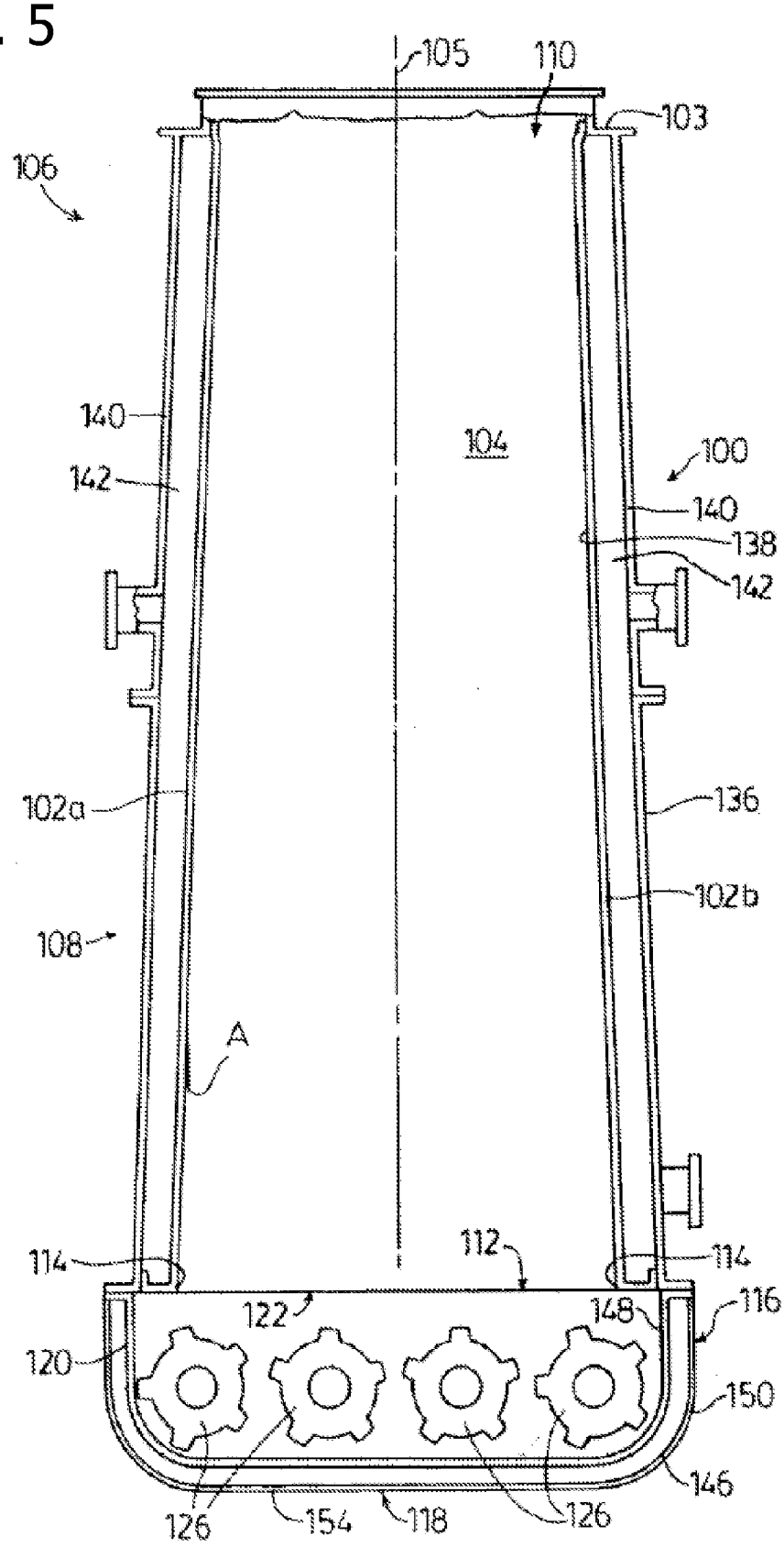
FIG. 5 is a cross section taken along line 5-5 in FIG. 1.

As exemplified in FIGS. 1 and 5, holding tank 100 is preferably oriented such that the passage through holding tank 100 extends generally downwardly and the passage there through is configured so as to reduce, and preferably essentially prevent, bridging of feedstock in holding tank 100. Further, the passage from impregnator 10 to holding tank 100 preferably extends generally downwardly. Accordingly, it is preferred that the passage through holding tank 100 extends generally downwardly and that the passage has a greater cross sectional area at the lower end then the upper end. More preferably, the cross sectional area continually increases in the downward direction. This may be achieved by constructing the passage of the holding tank with one or more walls that diverge in the downward direction.

If the feedstock passing downwardly through holding tank 100 interlocks, it may form a blockage by a process known as bridging. The blockage may extend all the way across the passage in holding tank 100 thereby preventing downward movement of feedstock and causing a gap in the supply of feedstock to the downstream process unit. Alternately, it may block only part of the passage. In any event, intervention would then be required to remove the blockage. The interruption of feedstock delivery to the downstream process unit could require part of a plant to be shut down while the blockage is removed thereby reducing throughput and also requiring the plant to be brought back to steady state operating conditions once the blockage is cleared. Accordingly, the holding tank may require monitoring to permit intervention at an early stage should bridging occur. By increasing the cross sectional area in the downstream direction, the tendency of the feedstock to form a blockage of the passage is reduced and may be eliminated.

Figure 10:
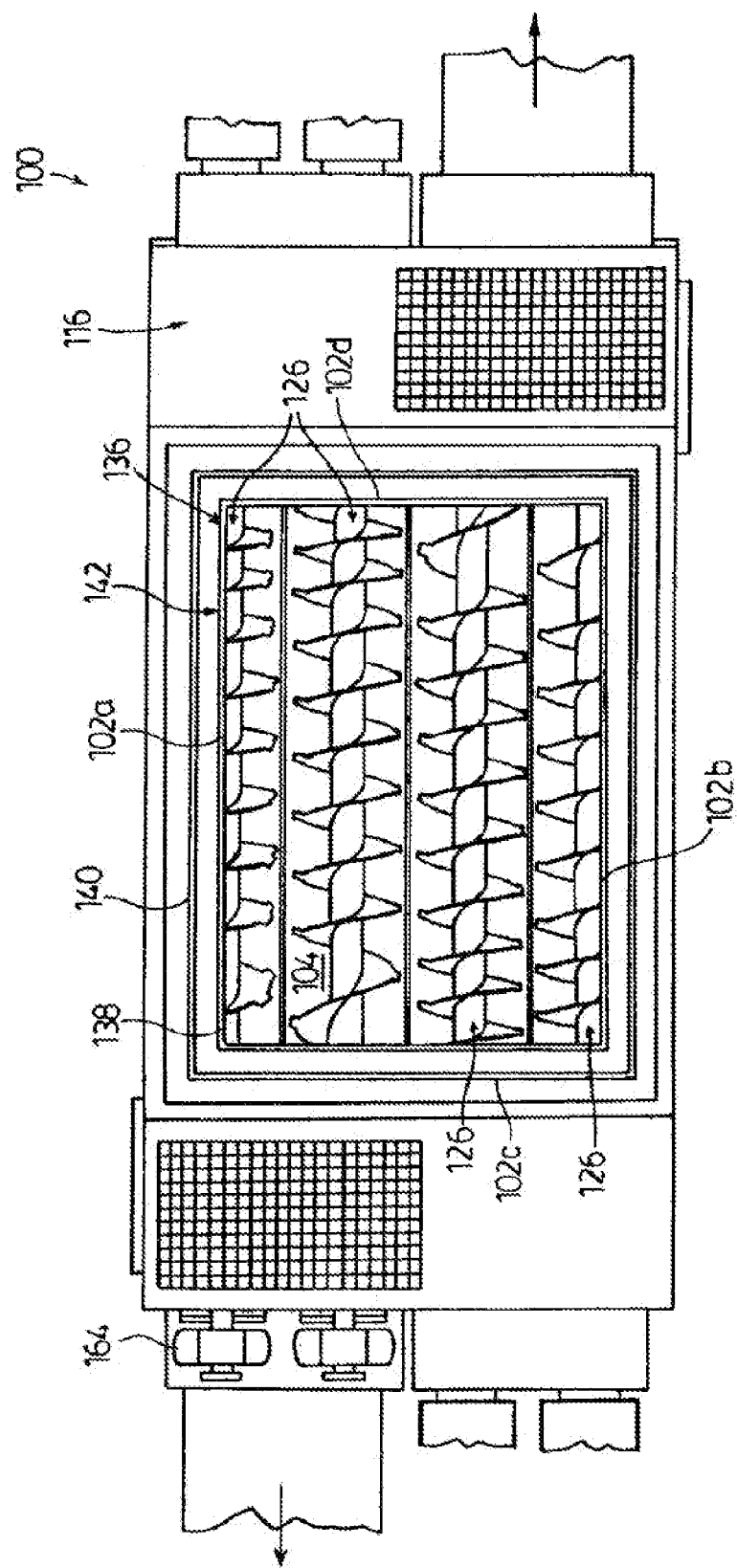
FIG. 10 is a cross-section taken along line 10-10 in FIG. 1.

As exemplified in FIGS. 5 and 10, holding tank 100 comprises at least one sidewall 102, which defines a volume or passage 104. In the embodiment shown, holding tank apparatus 100 comprises four sidewalls, namely front wall 102a, and a spaced apart opposed rear wall 102b, and a side wall 102c and a spaced apart opposed side wall 102d, and further comprises a top wall 103. Accordingly, passage 104, which is defined by sidewalls 102a, 102b, 102c and 102d is rectangular in transverse section. In other embodiments, holding tank apparatus 100 may comprise, for example, a single rounded sidewall so as to have a transverse section that is circular, elliptical or the like. It will be appreciated that any other transverse section may be utilized.

Passage 104 is preferably longitudinally extending, for example along axis 105, and comprises an upper portion 106, and a lower portion 108. Passage 104 preferably extends vertically. However passage may extend generally vertically (i.e., at an angle to the vertical such that feedstock will flow downwardly therethrough under the force of gravity). In some embodiments, volume 104 may have a length along axis 105 of between about 5 ft and about 20 ft.

An inlet 110 is provided adjacent upper portion 106, and an outlet 112 is provided adjacent lower portion 108, at an elevation below the inlet 110. In the embodiment shown, inlet 110 is defined by an opening in top wall 103, and outlet 112 is defined by the lower ends 114 of sidewalls 102. It will be appreciated that inlet 110 may comprise the entirety of the top end of holding tank 100 and accordingly, a top wall 103 may not be required. It will be appreciated that in a preferred embodiment, no lower surface is provided for passage 104 and that the lower end of passage 104 is open. Accordingly, feedstock may flow downwardly through passage 104 unimpeded until it encounters feedstock stored in holding tank 100 or until it encounters housing 116. As exemplified, inlet 110 is in fluid communication with and receives cellulosic feedstock from outlet 24 of impregnator 10 (e.g., it is downstream of outlet conduit 58), and outlet 112 is preferably in fluid communication with and directs cellulosic feedstock to one or more autohydrolysis reactors (not shown).

Referring still to FIG. 5, in a preferred embodiment, lower end of 108 of passage 104 has a greater cross sectional area than upper end 106 of passage 104. That is, a transverse cross section taken through passage 104 adjacent outlet 112 has a greater cross sectional area than a transverse section taken through passage 104 adjacent inlet 110. For example, the cross sectional area taken adjacent outlet 112 may have an area of between about 40 ft² and about 60 ft² and the cross sectional area taken adjacent inlet 110 may have an area of between about 20 ft² and about 40 ft².

Sidewalls 102 may be configured in a variety of ways in order to provide lower end 108 with a greater cross sectional area than upper end 106. In the embodiment shown, sidewall 102a and sidewall 102b are opposed to each other, and sidewall 102c and sidewall 102d are opposed to each other, and each of the sidewalls diverge from axis 105 going from inlet 110 to outlet 112. Accordingly, passage 104 is substantially frusto-pyramidal, and lower end 108 has a greater cross sectional area than upper end 106. In an alternate embodiment, sidewalls 102a and 102b may extend substantially parallel to axis 105, and sidewalls 102c and 102d may diverge from axis 105. In yet another alternate embodiment, holding tank apparatus 100 may comprise a single rounded sidewall defining a frustoconical passage 104. In yet another embodiment, sidewalls 102 may be stepped. It is preferred that sidewalls 102 continually diverge and that they continually diverge for the entire length of passage 104 as exemplified. Preferably, they diverge at an angle A from the vertical from about 1° to about 20°, preferably from about 2° to about 5°. It will also be appreciated that inner surface 138 of sidewalls 102 are preferably smooth and clear of projections that could be a source causing bridging to occur.

Providing lower portion 108 with a greater cross sectional area than upper portion 106 may aid in preventing cellulosic material from adhering or sticking to sidewalls 102 as the cellulosic material passes through holding tank apparatus 100. Accordingly, each portion of cellulosic feedstock that passes through holding tank apparatus 100 may have essentially the same residence time in passage 104.

In alternate embodiments, lower portion 108 of passage 104 may not have a greater cross sectional area than upper portion 106 of passage 104. For example, each of sidewalls 102 may extend essentially vertically and parallel to each other.

In some embodiments, the feedstock may travel directly downwardly to the next process unit, e.g. a steam explosion reactor. In such a case, it is preferred the passage continually increase in cross sectional area (as opposed to using a hopper). However, it is preferred that the feedstock, after traveling downwardly through passage 104, is conveyed laterally (transverse to axis 105). Further, it is preferred that the feedstock is actively withdrawn from holding tank 104 instead of permitting the feedstock to passively exit therefrom. Accordingly holding tank 100 may further comprise or be provided with at least one conveyor adjacent outlet 112 that is configured to actively convey the cellulosic feedstock laterally across outlet 112 to withdraw the cellulosic feedstock from passage 104. Referring to FIGS. 5 to 8, in the embodiment shown, the at least one conveyor comprises a plurality of screw conveyors 126, which are housed in a housing 116. The conveyor may be any transport mechanism known in the art to actively transport feedstock laterally from outlet 112. For example, the conveyor may comprise an auger, a screw conveyor, tabbed flight screw with bars, or the like that extends transversely to axis 105.

In accordance with this invention, after traveling through passage 104, the feedstock is conveyed laterally (transverse to axis 105). Further, it is preferred that the feedstock is actively withdrawn from holding tank 104 instead of permitting the feedstock to passively exit therefrom. Accordingly holding tank 100 may further comprise or be provided with at least two conveyors adjacent outlet 112 that are configured to actively convey the cellulosic feedstock laterally across outlet 112 to withdraw the cellulosic feedstock from passage 104. Referring to FIGS. 5 to 8, in the embodiment shown, each conveyor comprises a plurality of screw conveyors 126 (e.g., two), which are housed in a housing or discharge unit 116. The conveyor may be any transport mechanism known in the art to transport, and preferably actively transport, feedstock laterally from outlet 112. For example, the conveyor may comprise an auger, a screw conveyor, tabbed flight screw with bars, a belt conveyor or the like that extends transversely to axis 105.

In the embodiment shown, housing 116 comprises a base 118, sidewalls 120, and an open top 122. Open top 122 is preferably at least as large as outlet 112, and is in vertical registration with outlet 112, such that material passing through outlet 112 may pass directly downwardly through open top 122. Accordingly, all of outlet 112 may be exposed to the conveyors in housing 116. It will be appreciated that in alternate embodiments, sidewalls 102 of passage 104 may provide the sidewalls of housing 116. That is, sidewalls 102 may extend beyond outlet 112. Accordingly, in such an embodiment, outlet 112 of passage 104 may not be defined by ends 114 of sidewalls 102, and rather, may be defined by a portion of sidewalls 102 above ends 114.

Housing 116 comprises at least first and second housing outlets 124a, 124b, through which cellulosic feedstock conveyed by screw conveyors 126 exits housing 116. Cellulosic feedstock exiting housing outlet(s) 124a, 124b may pass into two or more conduits 125, which may, for example, lead to two or more, e.g., autohydrolysis reactors 127 (see FIG. 1). Accordingly, outlet 124a may be coupled to a first conduit 125, which leads to a first hydrolysis reactor 127, and outlet 124b may be coupled to a second conduit 125, which leads to a second hydrolysis reactor 127.

Preferably each conduit 125 is provided with one or more screw conveyors or the like extending in the direction of conduit 125. An advantage of having more then one outlet 124a, 124b is that two treated feedstock streams may be provided from holding tank 100, each of which may be fed to a different downstream process vessel, e.g. a different steam explosion reactor.

Figure 6:
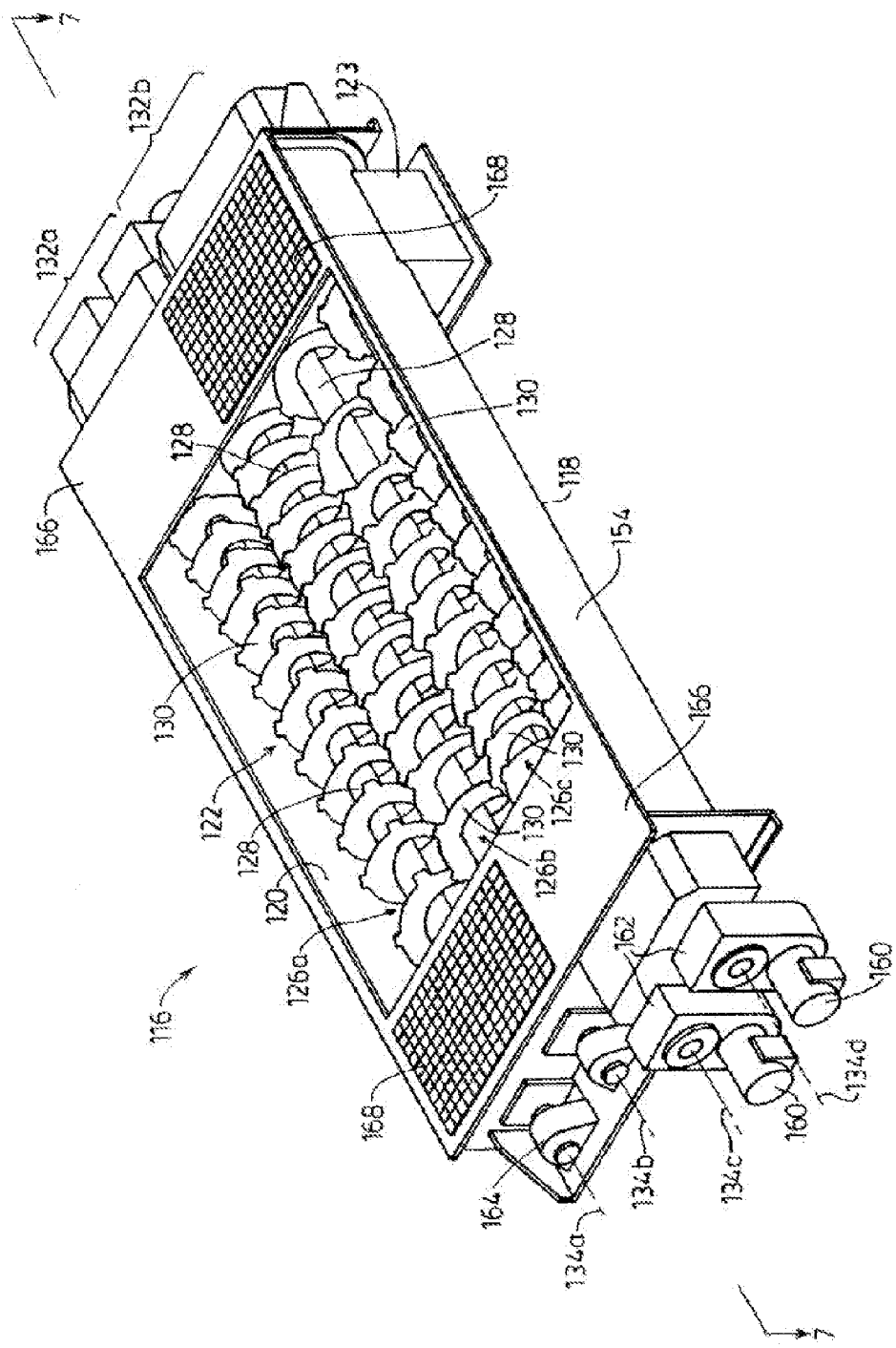
FIG. 6 is a perspective view of an embodiment of discharge member of the present invention, shown removed from a holding tank.
Figure 7:
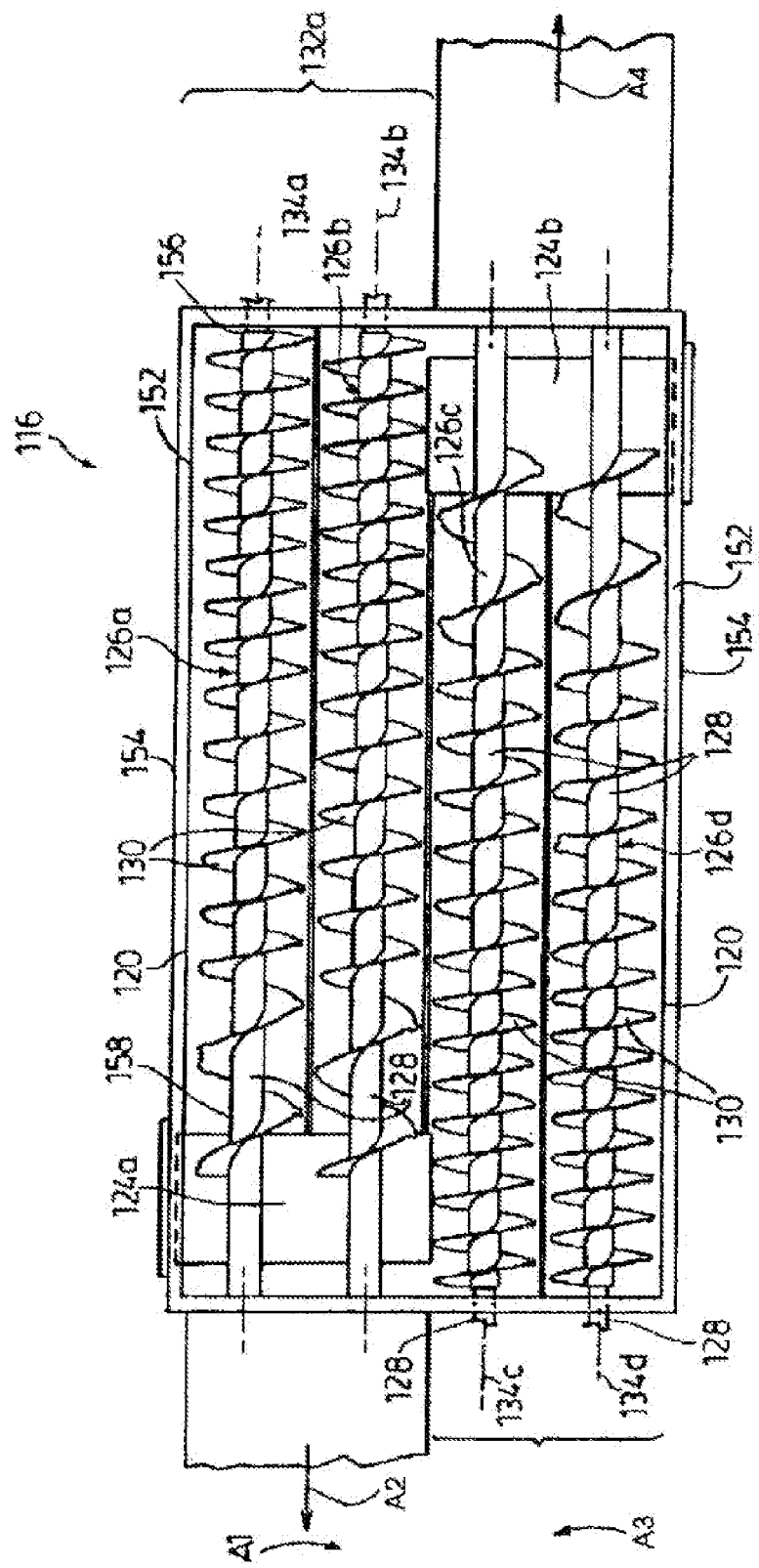
FIG. 7 is a cross-section taken along line 7-7 in FIG. 6.
Figure 8:
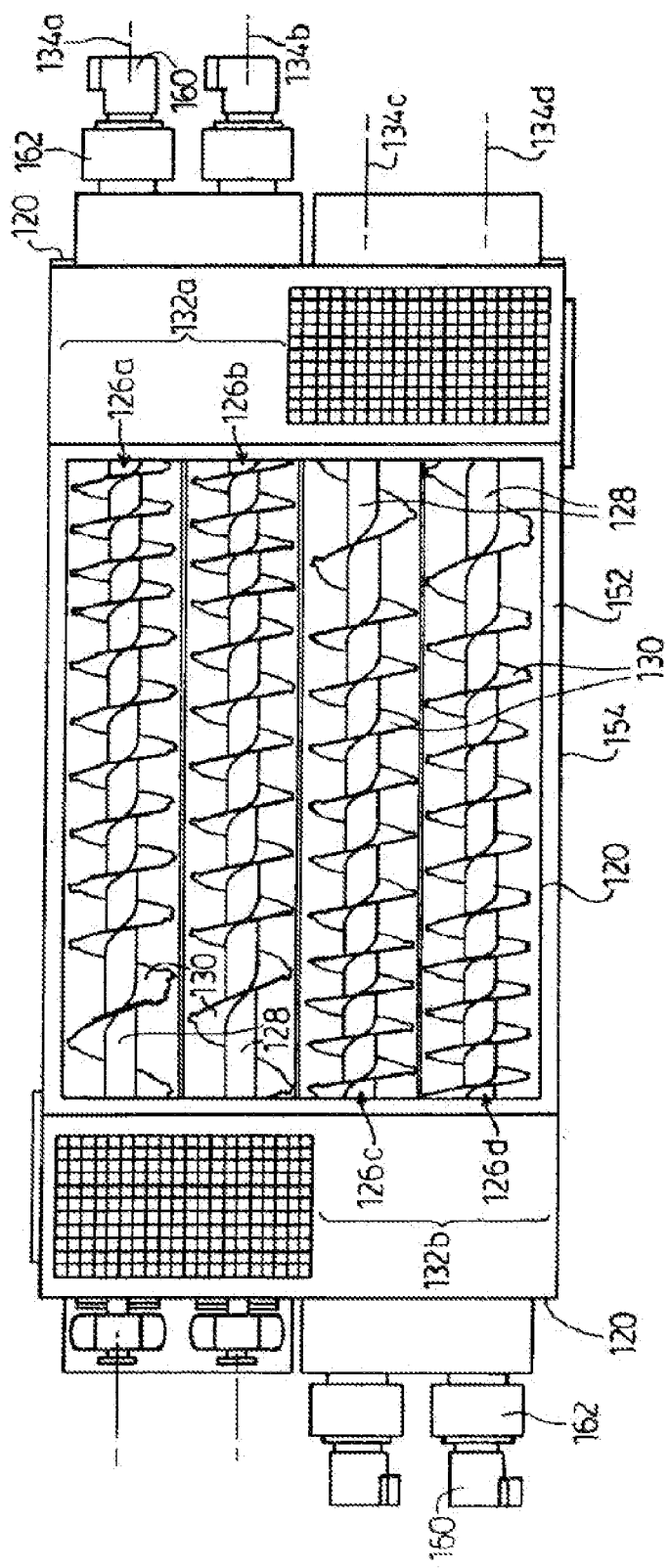
FIG. 8 is a top view of the discharge member of FIG. 6.
Figure 9:
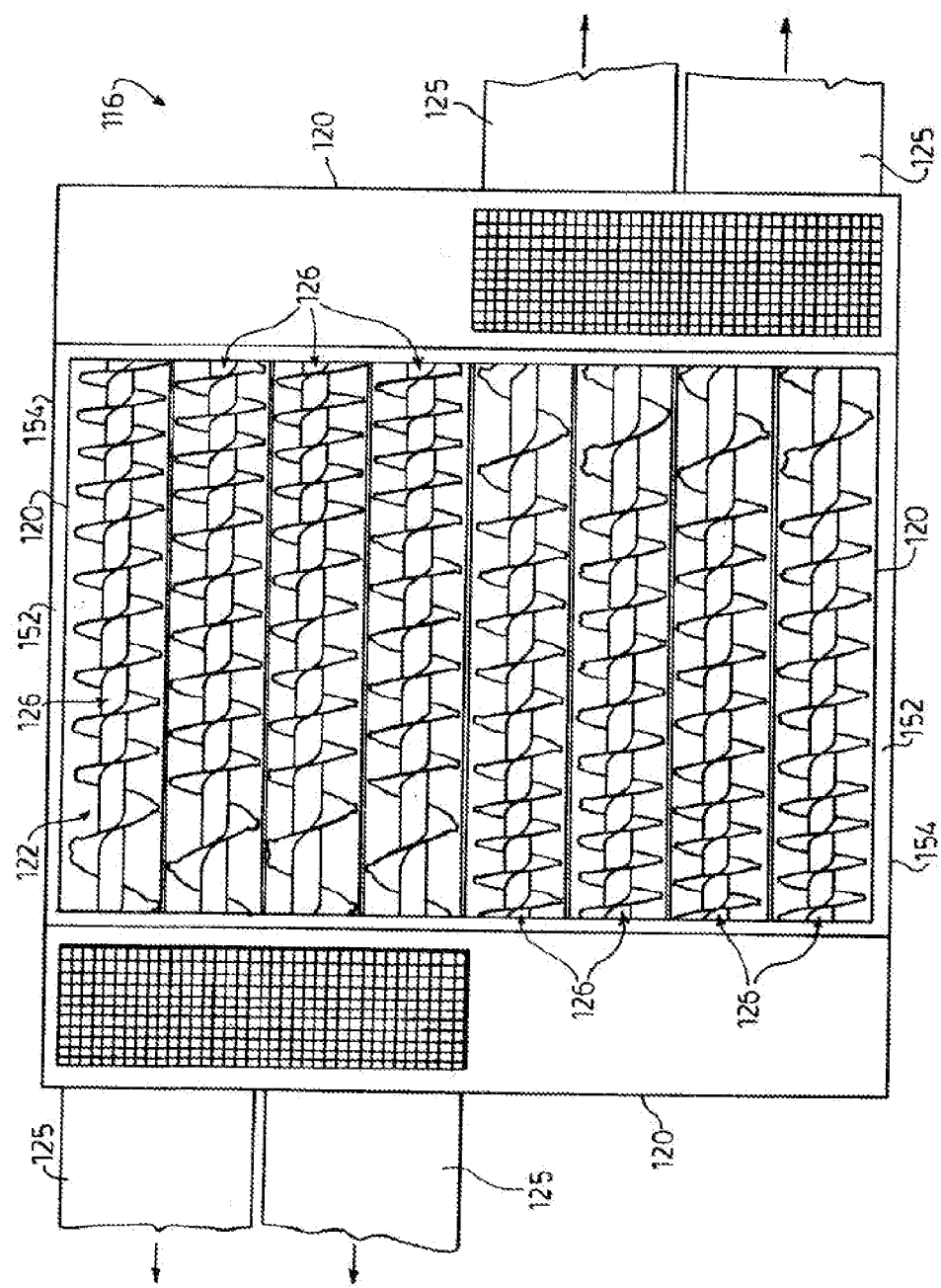
FIG. 9 is a top view of an alternate embodiment of a discharge member of the present invention.

As exemplified, housing 116 comprises two housing outlets 124a, 124b, defined in base 118 (see FIG. 7). Preferably, each outlet 124 is positioned such that it is not underneath passage 104 (laterally spaced from passage 104) and preferably more then one outlet 124 is provided. An advantage of positioning outlets 124 laterally from passage 104 is that feedstock may be withdrawn from all of outlet 112 and, more preferably, evenly from across outlet 112. Further, housing outlets 124a and 124b are preferably positioned on opposite sides of housing 116. Accordingly, housing outlets 124a and 124b may direct cellulosic material to two different, e.g., autohydrolysis reactors, positioned on opposite sides of holding tank 100. As exemplified in FIGS. 1 and 6, housing 116 may have upper wall 166 that extends over the portion of housing 116 positioned laterally of holding tank 100. Top wall 166 may cover the portion of screw conveyor 126 positioned laterally of holding tank 100. Optionally, a grate 168, or other member that provides a window, may be position in top wall 166 above outlet 124. Grate 168 permits a worker to observe the travel of feedstock into conduits 125.

As exemplified the screw conveyors 126 are mounted above base 118, and each screw conveyor extends transversely to axis 105 across all of outlet 112 (i.e. the length L of each screw conveyor extends at least from a first side of outlet 112 to a second side of outlet 112). Each screw conveyor 126 comprises a shaft 128 and at least one helical flight 130 extending about the shaft, and is configured to rotate to engage material exiting outlet 112, and to convey it towards one of the housing outlets 124. Shaft 128 may be rotatably mounted by any means known in the art. As exemplified, shaft 128 has one end journalled in a bearing housing 164 and a second end journalled in a transmission housing 162.

In the embodiment shown, housing 116 comprises four screw conveyors 126, which are arranged in pairs. Each pair comprises two adjacent screw conveyors 126 which convey the cellulosic feedstock in the same direction towards a common housing outlet 124. In the embodiment shown, first pair 132a comprises screw conveyors 126a and 126b, which rotate about respective first 134a and second 134b generally parallel axes, and second pair 132b comprises screw conveyors 126c, and 126d, which rotate about respective first 134c and second 134d generally parallel axes. Each of axes 134 are preferably horizontal, but may be at an angle of up to 45° or greater from the horizontal. Accordingly, screw conveyors 126a and 126b transport treated feedstock to outlet 124a and screw conveyors 126c and 126d transport treated feedstock to outlet 124b, which is on an opposed side to outlet 124a. It will be appreciated that screw conveyors 126a, 126b, 126c and 126d extend under essentially all of outlet 112. Therefore, the screw conveyors 126 preferably withdraw treated feedstock for all portions of outlet 112. Alternately, or in addition, each outlet 124 may have one or more screw conveyors 126 or other transport member associated therewith.

Referring still to FIG. 7, as exemplified, screw conveyors 126a and 126b of first pair 132a may each be rotated in a direction indicated by arrow A1, to feed material from above in a direction indicated by arrow A2 towards housing outlet 124a. Further, screw conveyors 126c and 126d of second pair 132b may each be rotated in a direction indicated by arrow A3, to feed material from above in a direction indicated by arrow A4 towards housing outlet 124b.

In order to permit each screw conveyors 126 to be rotated in a particular direction of rotation, each screw conveyor may be driven by its own drive motor 160. As shown in FIGS. 6 and 7, each shaft 128 extends outwardly past sidewall 120 into a transmission housing 162 wherein motor 160 is drivingly connected to shaft 128. Any driving linkage known in the art may be used. It will be appreciated that in an alternate embodiment, two or more shafts may be driven by a single motor 160.

Accordingly, as exemplified, housing outlets 124a and 124b are positioned on laterally opposite sides of housing 116, and each helical flight 130 is right-handed. Accordingly, direction A1 and direction A3 are opposite to each other, and directions A2 and A4 are opposite to each other. However, in alternate embodiments, housing outlets 124a and 124b may be positioned on the same lateral side as each other. In such an embodiment, directions A1 and A3 may be substantially the same, and directions A2 and A4 may be substantially the same. In yet further alternate embodiments, the helical flight 130 of the first pair 132a of screw conveyors 126a, 126b, may be right handed, and the helical flight 130 of the second pair 132b of screw conveyors 126c, 126d may be left handed. Accordingly, in such an embodiment, directions A1 and A3 may be the same, and direction A2 and A4 may be opposite. It will be appreciated that each pair of screw conveyors 126 may be configured such that they rotate in opposite directions. For example, screw conveyor 126a may be configured to rotate clockwise and screw conveyor 126b may be configured to rotate counterclockwise.

It will be appreciated that in alternate embodiments, one or more screw conveyors 126 may be otherwise configured. For example, housing 116 may comprise only one screw conveyor 126 and one outlet 124, or housing 116 may comprise a plurality of screw conveyors which are not arranged in pairs (e.g the screw conveyors may be arranged in sets of three, or as single screw conveyors), or housing 116 may comprise more than two pairs of screw conveyors. For example, in an alternate embodiment shown in FIG. 9, holding tank 100 comprises four housing outlets 124, each being upstream from a conduit 125, and four pairs 132 of screw conveyors 126.

Referring still to FIGS. 5-7, at least one of the screw conveyors 126, and preferably all of the screw conveyors 126, has a variable pitch along its length. That is, the pitch of helical flight 130 is not constant along the length L of at least one of the screw conveyors 126.

For example, in the embodiments shown, each screw conveyor has a first end 158 proximal to its respective housing outlet 124 (i.e. the housing outlet towards which it conveys cellulosic feedstock), and a second end 156 distal to its respective housing outlet 124 (shown in FIG. 7). The pitch of helical flight 130 at first end 158 is greater or wider than the pitch of helical flight 130 at second end 156. For example, the pitch at the first end may be between about 14 inches and about 18 inches, and the pitch at the second end may be between about 4 inches and about 8 inches.

In the embodiments shown, the pitch of each helical flight 130 generally varies continuously, and preferably at a constant rate, between the first end 158 and the second end 156. That is, the pitch gradually becomes wider towards each discharge member outlet 124. In alternate embodiments, an abrupt transition between wider and narrower regions of flight may occur. For example, each screw conveyor may have a first region extending from first end 158 towards a mid-point of screw conveyor 126, and a second region extending from second end 156 towards the midpoint. The first region may have a first range of pitch and the second region may have a second range of pitch. For example, the first range of pitch may be between about 14 inches and about 18 inches, and the second range of pitch may be between about 4 inches and about 8 inches. In yet another embodiment, each screw conveyor may comprise an intermediate region between the first region and the second region, and the intermediate region may have a third range of pitch that is less than the first range of pitch and more than the second range of pitch. For example, the third range of pitch may be between about 6 inches and about 10 inches.

Preferably, the screw conveyors 126 of each pair 132 have the same pitch at any location along their lengths. That is, the helical flight of screw conveyors 126a and 126b is essentially identical, and the helical flight of screw conveyors 126c and 126d is essentially identical.

Furthermore, the pitch of a first pair of screw conveyors is preferably a mirror image of the pitch of a second pair of screw conveyors, which convey the cellulosic feedstock in a direction opposite to the first pair of screw conveyors. That is, the pitch of screw conveyors 126a and 126b, which convey cellulosic material in direction A2, is a mirror image of the pitch of screw conveyors 126c and 126d, which convey cellulosic material in a direction A4.

Providing each screw conveyor with a variable pitch, and more specifically with a narrower pitch distal to the housing outlet, permits more equal amounts, and may allow for substantially equal amounts of cellulosic feedstock to be withdrawn from each portion of outlet 112. That is, material deposited in screw conveyor 126 at the distal end 156 will be conveyed towards the respective outlet 124 for that screw conveyor. As that material is transported laterally, the pitch of the screw increases permitting additional material to be deposited directly in the screw conveyor from outlet 112. Further increases in the pitch will permit additional portions of the material to fall into screw conveyor. The portion or portions of the screw conveyor closer to outlet 124 (in the direction of transport) has a wider pitch such that it may accommodate material conveyed from the distal region, as well as material deposited directly thereon from passage 104. Accordingly, feedstock is withdrawn from across all of outlet 112.

Referring to FIGS. 5 and 10, holding tank apparatus 100 preferably further comprises a heating jacket 136 provided on at least a portion of the holding tank apparatus 100. Preferably, the at least one sidewall 102 is provided with a heating jacket. For example, in the embodiment shown, heating jacket 136 surrounds all of each sidewall 102. Heating jacket 136 may comprise a plurality of outer walls that are generally parallel to and spaced from sidewalls 102 so as to define an enclosure 142 therebetween. A fluid may be passed through enclosure 142 from an inlet (not shown) to an outlet (not shown) so that a heated fluid is passed through enclosure 142. Heating jacket 136 may be of any construction known in the art. Accordingly, the cellulosic material may be heated to a predetermined temperature, or maintained at a predetermined temperature as it passes through holding tank apparatus 100.

Referring to FIG. 5, in a further preferred embodiment, housing 116 also comprises a second heating jacket 146 provided by housing 116. In the embodiment shown, heating jacket 146 is configured similarly to heating jacket 136, and may comprise an outer wall 154 spaced outwardly from sidewalls 120 and/or base 118 and is configured for passing a heated fluid through an enclosure 150 defined between outer walls 154 and sidewalls 120 and/or base 118. Heating jacket 146 may be of any construction known in the art.

In some embodiments, one or more temperature sensors may be provided in passage 104. For example, a first thermocouple (not shown) may be provided in the upper portion 106 of passage 104, to measure the temperature of the cellulosic feedstock entering inlet 110, and a second thermocouple (not shown) may be provided in the lower portion 108 of passage 104, to measure the temperature of the cellulosic feedstock exiting outlet 112. In some embodiments, one or more displays (not shown) may be coupled to the one or more temperature sensors, such that a user may view the measured temperatures, and optionally, adjust the amount of heat provided to holding tank 100 based on the measured temperatures. In further embodiments, the one or more sensors may be coupled to a processor, which may automatically adjust the amount of heat provided to holding tank 100 based on the measured temperatures.

A method of treating a cellulosic feedstock that may be used for ethanol production will now be described. Although the method will be described with reference to holding tank apparatus 100, it will be appreciated that the method may be carried out using an alternate apparatus, and holding tank apparatus 100 may be operated according to an alternate method.

A suitable cellulosic feedstock is preferably first subjected to moisture impregnation to raise the moisture content of the feedstock to a predetermined level prior to entry to the holding tank. Preferably, the moisture content of the feedstock upon entry to the holding tank is from about 30 wt % to about 60 wt %, preferably from about 45 wt % to about 55 wt %. The cellulosic feedstock may be obtained from, for example, a pre-treatment device such as impregnator 10, in which moisture is added to the cellulosic feedstock to raise the moisture content from, e.g., less than about 15% to between about 30% and about 60 wt % upon entry to the holding tank. Preferably, the moisture content is between about 45 wt % and about 55 wt % upon entry to the holding tank.

In a water impregnator, water is added to the feedstock. Preferably, the amount that is added is sufficient to raise the moisture level to a predetermined level for the downstream process, preferably hydrolysis, more preferably autohydrolysis followed by enzymatic hydrolysis. In order to prevent excess water being added to the feedstock, a limited amount of water is preferably provided such that excess water need not be removed. As the feedstock is fibrous and comprises discrete blocks of material, the mass transfer characteristics of the material govern the rate at which moisture applied to the outside of the feedstock penetrates into the core of the feedstock such that the moisture level taken across each block of material is generally uniform. Autohydrolysis in a steam explosion reactor is a relatively quick process (the residence time may be from about 2 to about 10 minutes). Due to the short residence time, it has been determined that some (e.g., the inner core of the blocks of material) may not be fully reacted during autohydrolysis if those portions do not have a sufficient moisture content. This incomplete reaction may require either separation of the unreacted material prior to downstream processing (e.g., hydrolysis) or permitting unreacted material to pass through the downstream process units, which may result in material not converted to fermentable sugars.

It has also been determined that heating the feedstock above about 70° C. results in degradation of the sugars in the feedstock. If the feedstock is over heated, then portions of the hemicellulose will degrade resulting in loss of yield and potential negative effect on subsequent enzymatic hydrolysis or fermentation process. Further, if the material that enters an autohydrolysis reactor is too cold, then the first portion of the reactor will tend to act as a preheater rather than as a autohydrolysis reaction resulting in a reduced yield.

Accordingly, the cellulosic feedstock, preferably after being subjected to impregnation, is then conveyed to a holding tank wherein the feedstock is passed through a heated passage. The heated holding tank may be, for example, holding tank 100, which comprises an inlet 110 disposed at an elevation above outlet 112. Accordingly, the cellulosic feedstock may be passed downwardly through the holding tank from the inlet towards the outlet under the force of gravity.

The feedstock is preferably provided with a residence time in the holding tank such that a desired moisture and temperature profile through the material is obtained. For example, it is preferred that the core of the blocks of material have a moisture content that is within 80%, preferably 90% of the moisture content of the exterior surface of the material. Accordingly, for example, if the moisture content of the exterior surface of the material is from 45 wt % to 55 wt %, then the moisture content of the core of the material is preferably from 40.5 to 49.5 wt %.

The holding tank may be heated in a variety of ways, for example by passing a heated fluid through a heating jacket provided on at least a portion of the holding tank. The heating jacket may be, for example, heating jacket 136 and optionally heating jacket 146. Optionally, electrical resistance heating may be used. Heat may also be supplied internally in passage 104.

The heated holding tank preferably serves to maintain the cellulosic feedstock at a desired temperature. For example, in some embodiments, the cellulosic feedstock enters the holding tank at a temperature of between about 50° C. and about 70° C., preferably between about 50° C. and about 65° C., and the holding tank is configured to maintain the cellulosic feedstock at the temperature between about 50° C. and about 70° C., and preferably between about 50° C. and about 65° C. In alternate embodiments, rather than maintaining the cellulosic feedstock at a desired temperature, the heated holding tank may serve to heat the cellulosic feedstock to a desired temperature. For example the cellulosic feedstock may enter the heated holding tank at a first temperature, and may exit the holding tank at a second temperature higher than the first temperature. The second temperature may be, for example, between about 50° C. and about 70° C., and more preferably, between about 55° C. and about 65° C. In various embodiments, the cellulosic feedstock enters the heated holding tank at a first temperature, and exits the heated holding tank at second temperature lower than the first temperature. In accordance with such embodiments, typically the first temperature is above 50° C. and the second temperature is between about 50° C. and about 70° C., and more typically between about 55° C. and about 65° C.

Preferably, a heated fluid is used to heat the feedstock. The fluid preferably has a temperature from 70 to 90° C. In order to avoid overheating the feedstock and degrading the sugars in the feedstock, the upper temperature of the heat source is limited requiring a consequential increase in the residence time (e.g., up to one hour) prior to subjecting the feedstock to downstream processing, preferably autohydrolysis, so that the core of the blocks may be raised to a predetermined temperature. For example, it is preferred that the core of the blocks of material have a temperature that is within 80%, preferably 90% of the temperature of the exterior surface of the material. Accordingly, for example, if the temperature of the exterior surface of the material is from 50 to 70° C., then the temperature of the core of the material is preferably from 45 to 63° C.

In some embodiments, the method may further comprise monitoring the temperature of the cellulosic feedstock in the heated holding tank. For example, as described previously, one or more temperature sensors may be provided within the holding tank. Preferably, a first temperature sensor is provided adjacent to the inlet of the holding tank, and a second temperature sensor is provided at the outlet of the holding tank. In further embodiments, the method may further comprise adjusting the amount of heat applied to the holding tank based on the temperature of the cellulosic material in the holding tank. For example, in some embodiments, it may be desired that the temperature of the cellulosic feedstock exiting the heated holding tank is about 65° C. Accordingly, in such an embodiment, if the first temperature sensor reads a temperature of about 55° C., for example, and the second temperature sensor reads a temperature of about 60° C., for example, the amount of heat applied to the holding tank may be increased until the second temperature sensor reads a temperature of 65° C. The amount of heat may be increased by, for example, increasing a flow rate of the fluid circulating in the heating jacket, or by increasing a temperature of the fluid circulating in the heating jacket. Preferably, the amount of heat applied is adjusted automatically, for example by a processor coupled to the temperature sensors and to the heating jacket. Alternatively, the amount of heat applied may be adjusted manually.

The cellulosic feedstock is preferably withdrawn in a lateral direction from the holding tank and, more preferably, with generally even amounts withdrawn from all portions of the outlet of the holding tank. By withdrawing from all portions of the outlet of the holding tank, each layer of feedstock entering the holding tank may have a generally uniform residence time in the holding tank.

The cellulosic feedstock is preferably subsequently subjected to hydrolysis. More preferably, the cellulosic feedstock is subjected to autohydrolysis followed enzymatic hydrolysis, converting the cellulose of the cellulosic feedstock to one or more sugars. The hydrolysis may take place in one or more hydrolysis reactors, which may include autohydrolysis (not shown), which are provided downstream from the holding tank, and are in fluid communication with the holding tank. For example, as described hereinabove, one or more conduits 125 may extend from housing outlets 124 towards one or more autohydrolysis reactors.

The method is preferably carried out such that the cellulosic feedstock has a residence time in the holding tank of up to 60 minutes. The feedstock may have a residence time in the holding tank of between about 5 minutes and about 45 minutes and preferably between 10 minutes and 30 minutes.

Furthermore, the method is preferably operated continuously and at steady state, such that the rate at which cellulosic feedstock is deposited into an inlet of the holding tank is equal to the rate at which cellulosic feedstock is removed from the outlet of the holding tank. Accordingly, in use, the method is preferably preceded by an initial start up phase, wherein material is not removed from the holding tank, and the tank is filled with cellulosic feedstock from impregnation chamber 12. When the tank is filled to a desired level, the method may commence, such that the holding tank is operated at steady state, and a generally constant residence time is maintained. II.

In further embodiments, the cellulosic feedstock is passed from the outlet of the impregnation chamber to the inlet of a holding tank. For example the cellulosic feedstock may be passed from outlet 18 of impregnation chamber 10, into inlet 110 of holding tank 100.

The cellulosic feedstock, with or without being subjected to impregnation, is then preferably passed downwardly through the holding tank. For example, referring to holding tank 100, inlet 110 is disposed at an elevation above outlet 112. Accordingly, the material may migrate downwardly from the inlet towards the outlet under the force of gravity. Furthermore, in embodiments wherein lower portion 108 has a greater cross sectional area than upper portion 106, the material will further migrate laterally as it migrates downwardly.

Preferably a generally constant residence time is maintained in the holding tank. That is, the holding tank is preferably operated continuously at steady state conditions, such that all parts of each portion or layer of feedstock added at inlet 110 pass downwardly to outlet 112 at about the same rate. This result may be achieved by withdrawing feedstock from all portions of the outlet 112. For example, the material may be removed from the outlet by operating one or more screw conveyors, such as screw conveyors 126 described hereinabove, such that feedstock from all parts of the outlet 112 (e.g., all of the same horizontal layer of feedstock in the outlet 112) are collected concurrently in the screw conveyor and transported to an outlet or downstream passage. It will be appreciated that the amount of material that is withdrawn from each part of the holding tank outlet may be varied by adjusting the pitch of the flight of the screw conveyor. By enlarging the pitch at certain locations, the amount of feedstock withdrawn at those locations may be increased.

It will be appreciated that, in use, there may be an initial start up phase, wherein material is not removed from the holding tank, and the tank is filled with cellulosic feedstock from impregnation chamber 12.

The residence time may be, for example, between about 10 and about 30 minutes. An advantage of this method is that a generally uniform residence time of the feedstock in the vessel may be achieved. For example, the variance of the residence time may be up to 5 minutes, preferably, less than 3 minutes and more preferably less than 2 minutes.

In various preferred embodiments including batch operation of a downstream hydrolysis reactor (i.e., digester), the method comprises maintaining a generally constant average residence time in the holding tank. For example, preferably at least about 90% (by weight) of the cellulosic feedstock exiting the holding tank and passed to the hydrolysis reactor has a residence time within about 10 minutes of the average residence time or at least about 80% (by weight) of the cellulosic feedstock exiting the holding tank and passed to the hydrolysis reactor has a residence time within about 5 minutes of the average residence time.

In one embodiment, the method comprises laterally conveying the cellulosic feedstock from the passage of the holding tank. Accordingly, once the feedstock reaches the exit (outlet) of the holding tank, the feedstock is conveyed laterally to, e.g., one or more conduits in flow communication with a downstream process unit. For example, the holding tank may comprise a discharge member, such as discharge member 116, adjacent lower end 108. One or more screw conveyors 126 of the discharge member may convey the cellulosic feedstock laterally across outlet 112, as described hereinabove.

Alternately, or in addition, in other embodiments, the cellulosic material is actively withdrawn from essentially the entirety of outlet 112. The feedstock is therefore moved at least with the assistance of machinery out of the holding tank. For example, discharge member 116 may comprise a plurality of screw conveyors extending across outlet 112, which, when rotated, engage the cellulosic material adjacent the entirety of the outlet 112, and convey it towards a discharge member outlet, as described hereinabove.

Alternately, or in addition, in other embodiments, generally equally amounts of the cellulosic material are preferably withdrawn from each portion of the outlet 112. In such an embodiment, a screw conveyor having different pitches (progressively wider pitches) may be used to convey the cellulosic feedstock laterally across the outlet of the holding tank. For example, a screw conveyor 126 may have a helical flighting having a first pitch adjacent a discharge member outlet, and a second pitch narrower than the first pitch distal to the discharge member outlet. Accordingly a generally equal amount of feedstock may be withdrawn from the region adjacent a discharge member outlet, and from a region distal to a discharge member outlet.

In some embodiments, a first portion of the cellulosic feedstock is preferably withdrawn in a first lateral direction and a second portion of the cellulosic feedstock withdrawing a second portion of the cellulosic feedstock is preferably in a second lateral direction, which is preferably opposite to the first direction. For example, the holding tank may comprise a first pair of screw conveyors and a second pair of screw conveyors. Each screw conveyor may comprise a right-handed helical flighting, and the first pair of screw conveyors may be rotated in a first direction to convey the cellulosic feedstock in a first lateral direction, and the second pair of screw conveyors may be rotated in a second direction to convey the cellulosic feedstock in a second lateral direction.

In some embodiments, the method further comprises maintaining a temperature in the holding tank between about 50° C. and about 75° C. For example, the holding tank may be optionally provided with a heating jacket, such as heating jacket 136 and/or discharge member 116 may be optionally provided with a heating jacket 146. The heating jacket may serve to heat the walls of the holding tank and/or the discharge member, such that the material within the holding tank is maintained at or raised to a temperature between 50° C. and about 75° C.

III.

Referring to FIGS. 5 and 10, vessel 100 (e.g., the holding tank) preferably further comprises a heating jacket 136 provided on at least a portion of vessel 100. Preferably, the at least one sidewall 102 is provided with a heating jacket. For example, in the embodiment shown, heating jacket 136 surrounds all of each sidewall 102. Heating jacket 136 may comprise a plurality of outer walls that are generally parallel to and spaced from sidewalls 102 so as to define an enclosure 142 therebetween. A fluid may be passed through enclosure 142 from an inlet (not shown) to an outlet (not shown) so that a heated fluid is passed through enclosure 142. Heating jacket 136 may be of any construction known in the art. Accordingly, the cellulosic material may be heated to a predetermined temperature, or maintained at a predetermined temperature as it passes through vessel 100.

Referring to FIG. 5, in a further preferred embodiment, housing 116 also or alternately may comprise a second heating jacket 146 provided by housing 116. In the embodiment shown, heating jacket 146 is configured similarly to heating jacket 136, and may comprise an outer wall 154 spaced outwardly from sidewalls 120 and/or base 118 and is configured for passing a heated fluid through an enclosure 150 defined between outer walls 154 and sidewalls 120 and/or base 118. Heating jacket 146 may be of any construction known in the art.

In some embodiments, one or more temperature sensors may be provided in passage 104. For example, a first thermocouple (not shown) may be provided in the upper portion 106 of passage 104, to measure the temperature of the cellulosic feedstock entering inlet 110, and a second thermocouple (not shown) may be provided in the lower portion 108 of passage 104, to measure the temperature of the cellulosic feedstock exiting outlet 112. In some embodiments, one or more displays (not shown) may be coupled to the one or more temperature sensors, such that a user may view the measured temperatures, and optionally, adjust the amount of heat provided to holding tank 100 based on the measured temperatures. In further embodiments, the one or more sensors may be coupled to a processor, which may automatically adjust the amount of heat provided to holding tank 100 based on the measured temperatures.

A method of treating a cellulosic feedstock that may be used for ethanol production will now be described. Although the method will be described with reference to holding tank 100, it will be appreciated that the method may be carried out using an alternate apparatus, and discharge housing 116 may be operated utilizing alternate conveyors.

A suitable cellulosic feedstock is preferably first subjected to moisture impregnation to raise the moisture content of the feedstock to a predetermined level prior to entry to the discharge housing 116, and preferably prior to entry to holding tank 100. Preferably, the moisture content of the feedstock upon entry to the holding tank or discharge housing 116 is from about 30 wt % to about 60 wt %, preferably from about 45 wt % to about 55 wt %. The cellulosic feedstock may be obtained from, for example, a pre-treatment device such as impregnator 10, in which moisture is added to the cellulosic feedstock to raise the moisture content from, e.g., less than about 15% to between about 30% and about 60 wt % upon entry to the holding tank. Preferably, the moisture content is between about 45 wt % and about 55 wt % upon entry to the holding tank.

The cellulosic feedstock is passed from the outlet of the impregnator 10 to the inlet of a passage upstream of discharge housing 116, e.g., holding tank 100. For example the cellulosic feedstock may be passed from outlet 18 of impregnator 10, into inlet 110 of holding tank 100.

The cellulosic feedstock, with or without being subjected to impregnation, is then preferably passed downwardly through the vessel. For example, referring to holding tank 100, inlet 110 is disposed at an elevation above outlet 112. Accordingly, the material may migrate downwardly from the inlet towards the outlet under the force of gravity. Furthermore, in embodiments wherein lower portion 108 has a greater cross sectional area than upper portion 106, the material will further migrate laterally as it migrates downwardly.

The feedstock is withdrawn from the vessel and directed towards two downstream process units. Accordingly, the feedstock obtained from the vessel is divided into two or more process streams, some, or each or which, may be travel in a different direction. At least two streams are obtained and provided to at least two different downstream process units, preferably hydrolysis reactors. The downstream process units may be operated on a batch or semi batch basis and may be operated out of phase. Accordingly, one batch hydrolysis reactor may be operated while a second batch hydrolysis reactor is filled with the cellulosic feedstock. Preferably, the cellulosic feedstock is conveyed laterally across the outlet of the vessel, and preferably in different directions.

Preferably a generally constant residence time is maintained in the holding tank. That is, the holding tank is preferably operated continuously at steady state conditions, such that all parts of each portion or layer of feedstock added at inlet 110 pass downwardly to outlet 112 at about the same rate. This result may be achieved by withdrawing feedstock from all portions of the outlet 112. For example, the material may be removed from the outlet by operating one or more screw conveyors, such as screw conveyors 126 described hereinabove, such that feedstock from all parts of the outlet 112 (e.g., all of the same horizontal layer of feedstock in the outlet 112) are collected concurrently in the screw conveyor and transported to an outlet or downstream passage. It will be appreciated that the amount of material that is withdrawn from each part of the holding tank outlet may be varied by adjusting the pitch of the flight of the screw conveyor. By enlarging the pitch at certain locations, the amount of feedstock withdrawn at those locations may be increased.

It will be appreciated that, in use, there may be an initial start up phase, wherein material is not removed from the vessel, and the vessel is filled with cellulosic feedstock from impregnation chamber 12.

The residence time may be up to 60 minutes. Preferably, the residence time is between 10 minutes and 30 minutes. An advantage of this method is that a generally uniform residence time of the feedstock in the vessel may be achieved. For example, the variance of the residence time may be up to 5 minutes, preferably, less than 3 minutes and more preferably less than 2 minutes.

In some embodiments, the cellulosic feedstock is conveyed laterally across the outlet of the holding tank, preferably in different directions, to obtain the at least two streams. For example, at least two conveying devices may be utilized to convey a first portion of the cellulosic feedstock laterally in a first direction to obtain a first steam, and at least two conveying devices may be utilized to convey a first portion of the cellulosic feedstock laterally in a second direction to obtain a second stream. For example, the holding tank may comprise a first conveyor 132a, comprising first 126a and second 126b conveying devices and a second conveyor 132b comprising third 126c and fourth 126d conveying devices, as described hereinabove. The first and second conveying devices may be configured to convey a first portion of the cellulosic feedstock laterally across the at least one outlet in a first lateral direction to obtain the first stream, and the third and fourth conveying devices may be configured to convey a second portion of the cellulosic feedstock laterally across the at least one outlet in a second lateral direction to obtain the second stream. Accordingly, the cellulosic feedstock for the first stream is drawn from a first portion of the outlet, and the cellulosic feedstock for the second stream is drawn from a second portion of the outlet.

In some embodiments, the first stream may be conveyed towards a first conduit, for example towards conduit 125 via discharge outlet 124a, and conveying the second stream towards a second conduit, for example towards conduit 125 via discharge outlet 125b.

The at least two streams are then fed into different process units, e.g., hydrolysis reactors 127. For example one conduit 125 may lead towards a first hydrolysis reactor, and a second conduit 125 may lead to a second hydrolysis reactor. The hydrolysis reactors may be, for example, autohydrolysis reactors, or acid hydrolysis reactors. Preferably, the first and second hydrolysis reactors are operated on a batch basis, and are operated out of phase with each other. For example, the first conveyor of the holding tank may be engaged to fill the first hydrolysis reactor, while the second conveyor is at rest. When the first hydrolysis reactor has been filled to a desired level, operation of the first conveyor may be stopped, and first the hydrolysis reactor may be engaged, for example by adding enzymes. While the first hydrolysis reactor is operated, the second conveyor may be engaged in order to fill the second hydrolysis reactor.

In some embodiments, the method further comprises maintaining a temperature in the holding tank between about 50° C. and about 75° C. For example, the holding tank may be optionally provided with a heating jacket, such as heating jacket 136 and/or discharge member 116 may be optionally provided with a heating jacket 146. The heating jacket may serve to heat the walls of the holding tank and/or the discharge member, such that the material within the holding tank is maintained at or raised to a temperature between 50° C. and about 75° C.

IV.

Various embodiments of the present invention provide methods and apparatus for transporting a cellulosic feedstock. The methods and apparatus relate to a holding tank that can be positioned downstream from a cellulosic feedstock pre-treatment process, and that can be utilized to further prepare the cellulosic feedstock for, e.g., auto hydrolysis or hydrolysis.

The feedstock is preferably treated with water as to have a moisture content upon entry to holding tank 100 of from about 30 to about 60 wt % or from about 45 to about 55 wt %. For example, referring to FIGS. 1 and 2, an embodiment of a holding tank 100 of the present invention is shown wherein the holding tank 100 is positioned downstream from an impregnation chamber 10, which is preferably used to pre-treat the feedstock prior to the feedstock entering holding tank 100. Impregnation chamber 10 is preferably configured to pre-treat the cellulosic feedstock, for example by moistening and/or heating the cellulosic feedstock.

A preferred impregnation chamber 10 is exemplified in FIGS. 2-4, impregnation. As shown therein, impregnation chamber 10 may comprise an inlet 11, one or more conveyance members 12 for urging the cellulosic feedstock along the length of the chamber, one or more moisture injection ports 14, which may be provided on paddles 20 of conveyance member 12 and/or inner wall 22 of impregnation chamber 10, for injecting moisture into the cellulosic feedstock, one or more heating jackets 16 provided outward of inner wall 22 for heating the cellulosic feedstock, and an outlet 18. In order to prevent material stagnating in impregnation chamber 10, impregnation chamber 10 may have a bottom wall 24 that has two or more portions each of which has a conveyance member 12 associated therewith. Bottom wall 24 and conveyance member 12 are preferably configured such that bottom wall 24 is swept as conveyance member 12 rotates. For example, as exemplified in FIG. 4, bottom wall 24 may be scallop shaped, e.g., have two inverted arches or troughs. Further details regarding various embodiments of optional impregnation chamber 10 may be found in U.S. patent application Ser. Nos. 12/181,565; 12/181,596; 12/181,640; 12/181,666; 12/181,724 filed on Jul. 29, 2008 and Ser. Nos. 12/361,103 and 12/361,149 filed on Jan. 28, 2009, the entire contents of which are incorporated herein by reference.

After the cellulosic feedstock is optionally pre-treated in impregnation chamber 10, it is directed to holding tank 100, where it is held or contained for a residence time, such that, for example, moisture added in impregnation chamber 10 has sufficient time to penetrate into the feedstock so that the feedstock is ready for downstream processing. Alternately, or in addition, the feedstock may require additional time for all portions of the feedstock to be raised to a predetermined temperature that is suitable for downstream processing. Alternately, the feedstock entering holding tank 100 may be at the predetermined conditions for downstream processing and holding tank is used as a reservoir to hold prepared feedstock such that downstream processes may operate on a continuous basis. From holding tank 100, the cellulosic feedstock may be directed to one or more downstream process units, preferably auto hydrolysis and/or hydrolysis reactors (not shown), such that the cellulose may be hydrolyzed to produce sugars that are suitable for fermentation to ethanol.

As exemplified in FIGS. 1 and 5, holding tank 100 is oriented such that the passage through holding tank 100 extends generally downwardly and the passage therethrough is configured so as to reduce, and preferably essentially prevent, bridging of feedstock in holding tank 100. Accordingly, it is preferred that the passage through holding tank 100 extends generally downwardly and that the passage has a greater cross sectional area at the lower end then the upper end. More preferably, the cross sectional area continually increases in the downward direction. This may be achieved by constructing the passage of the holding tank with one or more walls that diverge in the downward direction.

If the feedstock passing downwardly through holding tank interlocks, it may form a blockage by a process known as bridging. The blockage may extend all the way across the passage in holding tank 100 thereby preventing downward movement of feedstock and causing a gap in the supply of feedstock to the downstream process unit. Alternately, it may block only part of the passage. In any event, intervention would then be required to remove the blockage. The interruption of feedstock delivery to the downstream process unit could require part of a plant to be shut down while the blockage is removed thereby reducing throughput and also requiring the plant to be brought back to steady state operating conditions once the blockage is cleared. Accordingly, the holding tank may require monitoring to permit intervention at an early stage should bridging occur. By increasing the cross sectional area in the downstream direction, the tendency of the feedstock to form a blockage of the passage is reduced and may be eliminated. As exemplified in FIGS. 5 and 10, holding tank 100 comprises at least one sidewall 102, which defines a volume or passage 104. In the embodiment shown, holding tank 100 comprises four sidewalls, namely front wall 102a and a spaced apart opposed rear wall 102b, and a side wall 102c and a spaced apart opposed side wall 102d, and further comprises a top wall 103. Accordingly, passage 104, which is defined by sidewalls 102a, 102b, 102c and 102d is rectangular in transverse section. In other embodiments, holding tank 100 may comprise, for example, a single rounded sidewall so as to have a transverse section that is circular, elliptical or the like. It will be appreciated that any other transverse section may be utilized.

Passage 104 is preferably longitudinally extending, for example along axis 105, and comprises an upper portion 106, and a lower portion 108. Passage 104 preferably extends vertically. However passage may extend generally vertically (i.e., at an angle to the vertical such that feedstock will flow downwardly therethrough under the force of gravity). In some embodiments, passage 104 may have a length along axis 105 of between about 5 ft and about 10 ft.

An inlet 110 is provided adjacent upper portion 106, and an outlet 112 is provided adjacent lower portion 108, at an elevation below the inlet 110. In the embodiment shown, inlet 110 is defined by an opening in top wall 104, and outlet 112 is defined by the lower ends 114 of sidewalls 102. It will be appreciated that inlet 110 may comprise the entirety of the top end of holding tank 100 and accordingly, a top surface 103 may not be required. It will be appreciated that in a preferred embodiment, no lower surface is provided for passage 104 and that the lower end of passage 104 is open. Accordingly, feedstock may flow downwardly through passage 104 unimpeded until it encounters feedstock stored in holding tank 100 or until it encounters discharge member 116. As exemplified, inlet 110 is in fluid communication with and receives cellulosic feedstock from outlet 18 of impregnation chamber 10, and outlet 112 is in fluid communication with and directs cellulosic feedstock to one or more auto hydrolysis reactors (not shown).

Referring still to FIG. 5, the lower end of passage 104 has a greater cross sectional area than upper end of passage 104. That is, a transverse cross section taken through passage 104 adjacent outlet 112 has a greater cross sectional area than a transverse section taken through passage 104 adjacent inlet 110. For example, the cross sectional area taken adjacent outlet 112 may have an area of between about 40 ft$^2$ and about 60 ft$^2$ and the cross sectional area taken adjacent inlet 110 may have an area of between about 20 ft$^2$ and about 40 ft$^2$.

Sidewalls 102 may be configured in a variety of ways in order to provide lower portion 108 with a greater cross sectional area than upper portion 106. In the embodiment shown, sidewall 102a and sidewall 102c are opposed to each other, and diverge from each other going from inlet 110 to outlet 112. Further sidewall 102b and sidewall 102d are opposed to each other, and diverge from each other going from inlet 110 to outlet 112. Accordingly, passage 104 is substantially frusto-pyramidal, and lower portion 108 has a greater cross sectional area than upper portion 104. In an alternate embodiment, sidewalls 102a and 102c may extend substantially parallel to each other, and sidewalls 102b and 102d may diverge from each other. In yet another alternate embodiment, holding tank 100 may comprise a single rounded sidewall defining a frustoconical passage 104. In yet another embodiment, sidewalls 102 may be stepped. It is preferred that sidewalls 102 continually diverge and that they continually diverge for the entire length of passage 104 as exemplified. Preferably, they diverge at an angle A from the vertical from about 1° to about 20°, preferably from about 2° to about 5°. It will also be appreciated that inner surface 138 of sidewalls 102 are preferably smooth and clear of projections that could be a source causing bridging to occur.

Providing lower portion 108 with a greater cross sectional area than upper portion 106 may aid in preventing cellulosic material from adhering or sticking to sidewalls 102 as the cellulosic material passes through holding tank 100. Accordingly, each portion of cellulosic feedstock that passes through holding tank 100 may have essentially the same residence time in passage 104.

In some embodiments, the feedstock may travel directly downwardly to the next process unit. In such a case, it is preferred the flow passage continually increase in cross sectional area (as opposed to using a hopper). However, it is preferred that the feedstock, after traveling downwardly through passage 104, is conveyed laterally (transverse to axis 105). Further, it is preferred that the feedstock is actively withdrawn from holding tank 104 instead of permitting the feedstock to passively flow out therefrom. Accordingly, in the exemplified embodiment, holding tank 100 is seated on a discharge member 116 adjacent outlet 112. Discharge member 116 is configured to convey the cellulosic material laterally across outlet 112 to actively withdraw the cellulosic feedstock from holding tank 100.

Referring to FIGS. 5 to 8, in the embodiment shown, discharge member 116 comprises a base 118, sidewalls 120, and an open top 122. Open top 122 is preferably at least as large as outlet 112, and is in vertical registration with outlet 112, such that material passing through outlet 112 may pass directly downwardly through open top 122. It will be appreciated that in alternate embodiments, sidewalls 102 of passage 104 may provide the sidewalls of discharge member 116. That is, sidewalls 102 may extend beyond outlet 112. Accordingly, in such an embodiment, outlet 112 of passage 104 may not be defined by ends 114 of sidewalls 102, and rather, may be defined by a portion of sidewalls 102 above ends 114.

Discharge member 116 may use any transport mechanism known in the art to actively transport feedstock laterally from outlet 112. For example, a discharge member 116 may comprise an auger, a screw conveyor, drag line conveyor, paddle conveyor or the like that extends transversely to axis 105. Discharge member 116 comprises at least a first discharge member outlet 124, through which cellulosic feedstock exits discharge member 116. Cellulosic feedstock exiting discharge member outlet(s) 124 may pass into one or more conduits 125, which may, for example, lead to one or more, e.g., auto hydrolysis reactors (not shown). Preferably more then one outlet 124 is provided. An advantage of having more then one outlet is that two treated feedstock stream may be provided from holding tank 100.

As exemplified, discharge member 116 comprises two discharge member outlets 124a, 124b (see FIG. 7). Preferably, each outlet 124 is positioned such that it is not underneath passage 104 (laterally spaced from passage 104) and preferably more then one outlet 124 is provided. An advantage of positioning outlets 124 laterally from passage 104 is that feedstock may be withdrawn from all of outlet 112 and, more preferably, evenly from across outlet 112. Further, discharge member outlets 124a and 124b are preferably positioned on opposite sides of discharge member 116. Accordingly, discharge member outlets 124a and 124b may direct cellulosic material to two different, e.g., auto hydrolysis reactors, positioned on opposite sides of holding tank 100. As exemplified in FIGS. 1, 6 and 7, discharge member 116 may have upper wall 166 that extends over the top surface of discharge member 116 positioned laterally of holding tank 100. Top wall 166 may cover the portion of screw conveyor 126 positioned laterally of holding tank 100. Optionally, a grate 168, or other member that provides a window, may be positioned in top wall 166 above outlet 124. Grate 168 permits a worker to observe the travel of feedstock into conduits 125.

Discharge member 116 preferably comprises at least one screw conveyor 126 mounted above base 118. As exemplified, each screw conveyor 126 comprises a shaft 128 and at least one helical flighting 130 extending about the shaft, and is configured to rotate to engage material exiting outlet 112, and to convey it towards one of the discharge member outlets 124. Shaft 128 may be rotatably mounted by any means known in the art. As exemplified, shaft 128 has one end journalled in a bearing housing 164 and a second end journalled in a transmission housing 162. In the embodiment shown, discharge member 116 comprises a plurality of screw conveyors 126, which are arranged in pairs. First pair 132a comprises screw conveyors 126a and 126b, which rotate about respective first 134a and second 134b generally parallel axes, and second pair 132b comprises screw conveyors 126c, and 126d, which rotate about respective first 134c and second 134d generally parallel axes. Each of axes 134 are preferably horizontal, but may be at an angle of up to 45° or greater from the horizontal. Accordingly, screw conveyors 126a and 126b transport treated feedstock to outlet 124a and screw conveyors 126c and 126d transport treated feedstock to outlet 124b, which is on an opposed side to outlet 124a. It will be appreciated that screw conveyors 126a, 126b, 126c and 126d extend under essentially all of outlet 112. Therefore, the screw conveyors 126 preferably withdraw treated feedstock for all portions of outlet 112. Alternately, or in addition, each outlet 124 may have one or more screw conveyors 126 or other transport member associated therewith.

Referring still to FIG. 7, as exemplified, screw conveyors 126a and 126b of first pair 132a may each be rotated in a direction indicated by arrow A1, to feed material from above towards discharge member outlet 124a. Further, screw conveyors 126c and 126d of second pair 132b may each be rotated in a direction indicated by arrow A2, to feed material from above towards discharge member outlet 124b.

In order to permit each screw conveyors 126 to be rotated, in a particular direction of rotation, each screw conveyor may be driven by its own drive motor 160. As shown in FIGS. 6 and 7, each shaft 128 extends outwardly past sidewall 120 into a transmission housing 162 wherein motor 160 is drivingly connected to shaft 128. Any driving linkage known in the art may be used. It will be appreciated that in an alternate embodiment, a single motor 160 may drive two or more shafts.

Accordingly, as exemplified, discharge member outlets 124a and 124b are positioned on laterally opposite sides of discharge member 116, and each helical fighting 130 is right-handed. Accordingly, direction A1 and direction A2 are opposite to each other. However, in alternate embodiments, discharge member outlets 124a and 124b may be positioned on the same lateral side as each other. In such an embodiment, directions A1 and A2 may be substantially the same. In yet further alternate embodiments, the helical flighting 130 of the first pair 132a of screw conveyors 126a, 126b, may be right handed, and the helical flighting 130 of the second pair 132b of screw conveyors 126c, 126d may be left handed. Accordingly, in such an embodiment, the first pair may rotate in the same direction as the second pair, and convey material in an opposite direction. It will be appreciated that each pair of screw conveyors 126 may be configured such that they rotate in opposite directions. For example, screw conveyor 126a may be configured to rotate clockwise and screw conveyor 126b may be configured to rotate counterclockwise.

Preferably, the helical flighting 130 of each screw conveyor has a first pitch adjacent its respective discharge member outlet 124 (i.e. the discharge member outlet towards which it conveys cellulosic feedstock), and a second pitch distal to its respective discharge member outlet 134 narrower than the first pitch. That is, screw conveyors 126a and 126b have a first pitch at end 158 adjacent discharge member outlet 124a, and a second narrower pitch at the end 156 that is distal to discharge member outlet 124a; and screw conveyors 126c and 126d have a first pitch adjacent discharge member outlet 124b, and a second narrower pitch distal to discharge member outlet 124b.

In the embodiments shown, the pitch of each helical flighting 130 gradually becomes wider towards each discharge member outlet 124. For example, the pitch may vary gradually from between about 4 inches and about 8 inches at the distal end 156 of screw conveyor 126 to between about 14 inches and about 16 inches the end 158 of screw conveyor 126 adjacent discharge member outlet 124. In alternate embodiments, an abrupt transition between wider and narrower regions of flighting may occur. For example, each screw conveyor may comprise a first flight adjacent a discharge member outlet 124 and a second flight upstream from the first flight. The first flight may have a first constant pitch, for example of between about 14 inches and about 18 inches, and the second fight may have a second constant pitch narrower than the first constant pitch, for example of between about 4 inches and about 8 inches. In a further embodiment, a third intermediate flight having a third constant pitch wider than the second flight and narrower than the first flight may be positioned between the first flight and the second flight. The third flight may have a pitch of between about 6 inches and about 10 inches, for example.

Providing each screw conveyor with a narrower pitch distal to the discharge member outlet may allow for substantially equally amounts of material to be withdrawn from each portion of outlet 112. That is, material deposited in screw conveyor 126 at the distal end 156 will be conveyed towards the respective outlet 124 for that screw conveyor. As that material is transported laterally, the pitch of the screw increases permitting additional material to be deposited directly in the screw conveyor from outlet 112. Further increases in the pitch will permit additional portions of the material to fall into screw conveyor. The portion or portions of the screw conveyor closer to outlet 124 (in the direction of transport) have a wider pitch such that it may accommodate material conveyed from the distal region, as well as material deposited directly thereon from passage 104. Accordingly, feedstock is withdrawn from across all of outlet 112.

It will be appreciated that in alternate embodiments, one or more screw conveyors 126 may be otherwise configured. For example, discharge member 116 may comprise only one screw conveyor 126 and one outlet 124, or discharge member 116 may comprise a plurality of screw conveyors which are not arranged in pairs, or discharge member 116 may comprise more than two pairs of screw conveyors. For example, in an alternate embodiment shown in FIG. 9, discharge member 116 comprises four discharge member outlets 124, and four pairs 132 of screw conveyors 126.

Referring to FIGS. 5 and 10, holding tank 100 preferably further comprises a heating jacket 136 provided on at least a portion of the sidewalls 102. For example, in the embodiment shown, heating jacket 136 surrounds all of each sidewall 102. Heating jacket 136 comprises a plurality of outer walls 140 that are generally parallel to and spaced from sidewalls 102 so as to define an enclosure 142 therebetween. A fluid may be passed through enclosure 142 from an inlet (not shown) to an outlet (not shown) so that a heated fluid is through enclosure 142. Heating jacket 136 may be of any construction known in the art. Accordingly, the cellulosic material may be heated to a desired temperature, or maintained at a desired temperature as it passes through holding tank 100.

Referring to FIG. 5, in a further preferred embodiment, discharge member 116 also comprises a heating jacket 146 provided on sidewalls 120 and/or base 118 of discharge member 116. Heating jacket 146 may be configured similarly to heating jacket 136, and may comprise an outer wall 154 spaced outwardly from sidewalls 120 and/or base 118 and is configured for passing a heated fluid through an enclosure 150 defined between outer walls 154 and sidewalls 120 and/or base 118.

A method of treating a cellulosic feedstock for ethanol production will now be described. Although the method will be described with reference to holding tank 100, it will be appreciated that the method may be carried out using an alternate apparatus, and holding tank 100 may be operated according to an alternate method.

A suitable cellulosic feedstock is preferably first treated to moisture impregnation to raise the moisture content of the feedstock to a predetermined level. Preferably, the moisture content of the feedstock upon entry to the holding tank is from about 30 wt % to about 60 wt %, preferably from about 45 wt % to about 55 wt %. This may be achieved by passing the feedstock through an impregnation chamber to an outlet of the impregnation chamber. The impregnation chamber may be, for example, impregnation chamber 10, and may comprise one or more conveyance members for urging the cellulosic feedstock along the impregnation chamber towards outlet 18 of impregnation chamber. As the cellulosic feedstock is passed through the impregnation chamber, it may be pretreated by one or more of moistening the cellulosic feedstock and heating the cellulosic feedstock, as described in U.S. patent application Ser. Nos. 12/181,565; 12/181,596; 12/181,640; 12/181,666; 12/181,724 filed on Jul. 29, 2008 and Ser. Nos. 12/361,103 and 12/361,149 filed on Jan. 28, 2009, the entire contents of which are incorporated herein by reference.

The cellulosic feedstock with or without being subjected to impregnation, is then conveyed to a holding tank wherein the feedstock is conveyed downwardly and laterally as it travels through the holding tank. For example, referring to holding tank 100, inlet 110 is disposed at an elevation above outlet 112. Accordingly, the material may migrate downwardly from the inlet towards the outlet under the force of gravity. Furthermore, as lower portion 108 has a greater cross sectional area than upper portion 106, the material will migrate laterally as it migrates downwardly.

Preferably, the method further comprises laterally conveying the cellulosic feedstock from the passage through the holding tank. Accordingly, once the feedstock reaches the exit of the holding tank, the feedstock is conveyed laterally to, e.g., one or more conduits in flow communication with a downstream process unit. For example, the holding tank may comprise a discharge member, such as discharge member 116, adjacent lower end 108. One or more screw conveyors 126 of the discharge member may convey the cellulosic feedstock laterally across outlet 112, as described hereinabove.

Alternately, or in addition, the cellulosic material is preferably actively withdrawn from essentially the entirety of outlet 112. The feedstock is therefore moved at least with an assistance of machinery out of the holding tank. For example, discharge member 116 may comprise a plurality of screw conveyors extending across outlet 112, which, when rotated, engage the cellulosic material adjacent the entirety of the outlet 112, and convey it towards a discharge member outlet, as described hereinabove.

In any embodiment, generally equally amounts of the cellulosic material is preferably withdrawn from each portion of the outlet 112. For example, a screw conveyor 126 of a discharge member 116 may have a helical flighting having a first pitch adjacent a discharge member outlet, and second pitch narrower than the first pitch distal to the discharge member outlet. Accordingly a generally equal amount of feedstock is withdrawn from the region adjacent a discharge member outlet, and from a region distal to a discharge member outlet.

In various embodiments, the exiting feedstock flux within any 25 cm$^2$ to 100 cm$^2$ component of the cross section of the outlet normal to the direction of flow does not differ by more than 10% to 20% from any other 25 cm$^2$ to 100 cm$^2$ component of the cross section. In various particular embodiments, the exiting feedstock flux within any 25 cm$^2$ component of the cross section of the outlet normal to the direction of flow does not differ by more than 10% from any other 25 cm$^2$ component of the cross section. In these and still further embodiments, the exiting feedstock flux within any component of the cross section of the outlet normal to the direction of flow, the area of which represents more than 5% of the total area of said cross section, does not differ by more than 10% from the exiting feedstock flux within any other such component of that cross section.

In some embodiments, a first portion of the cellulosic feedstock is preferably withdrawn in a first lateral direction and a second portion of the cellulosic feedstock withdrawing a second portion of the cellulosic feedstock is preferably in a second lateral direction, which is preferably opposite to the first direction. For example, the holding tank may comprise a discharge member having a first pair of screw conveyors and a second pair of screw conveyors. Each screw conveyor may comprise a right-handed helical flighting, and the first pair of screw conveyors may be rotated in a first direction to convey the cellulosic feedstock in a first lateral direction, and the second pair of screw conveyors may be rotated in a second direction to convey the cellulosic feedstock in a second lateral direction.

In some embodiments, the method preferably further comprises maintaining a temperature in the passage of the holding tank between about 50° C. and about 75° C. For example, the holding tank may be provided with a heating jacket, such as heating jacket 136. The heating jacket may serve to heat the walls of the holding tank, such that the material within the holding tank is maintained at or raised to a temperature between 50° C. and about 75° C.

The method preferably comprises operating the holding tank such that the cellulosic feedstock moves from the inlet to the outlet in about 10 to 30 minutes. Accordingly, in use, the method may be preceded by an initial start up phase, wherein a discharge member of the holding tank is not operated, and the tank is filled with cellulosic feedstock from impregnation chamber 12. When the tank is filled, the method may commence, such that the holding tank is operated at steady state with a predetermined residence time.

Generally, various methods and apparatus detailed elsewhere herein are suitable for treating and/or obtaining moisture-impregnated feedstocks. In particular, the methods detailed elsewhere herein regarding impregnators as depicted in, for example, FIGS. 2-4 are suitable for preparing moisture-impregnated feedstocks. Similarly, the apparatus (e.g., holding tanks) as depicted in, for example, FIGS. 5-10 are suitable for processes involving moisture-impregnated feedstocks.

Introduction of moisture to the cellulosic feedstock in accordance with the methods detailed herein generally increases the moisture content of the cellulosic feedstock and, more particularly, provides a moisture-impregnated feedstock. It has been observed that where the cellulosic feedstock has a relatively low moisture content the pores of the feedstock may have closed or collapsed onto themselves, thereby rendering a portion of the feedstock surface unavailable for receiving moisture. Thus, typically feedstocks subjected to moisture impregnation have a moisture content of at least about 5 wt % or at least about 10 wt %. However, as the moisture content of the feedstock increases, energy costs associated with initial processing (e.g., milling) increase and relatively high moisture contents may also impede heat transfer during subsequent hydrolysis (e.g., auto- or acid-catalyzed hydrolysis) and thus may negatively impact fermentable sugar yield. In addition, feedstocks to be moisture-impregnated generally have a moisture content near or below the moisture saturation level of the feedstock. Reference to a saturated feedstock refers to a feedstock in which all cell walls are saturated with water, but no free water resides within the pores of the feedstock. The fiber saturation level varies depending on, for example, the source of the feedstock, but generally is from about 25 wt. % to about 30 wt. %. Thus, generally the cellulosic feedstock to be moisture-impregnated has a moisture content of from about 10 wt % to about 40 wt %, or from about 20 wt % to about 30 wt %. Preferably, the moisture content of feedstocks to be subjected to moisture impregnation is from about 10 wt % to about 20 wt % or from about 10 wt % to about 15 wt %.

In accordance with various embodiments of the present invention, impregnation provides a moisture-impregnated feedstocks typically having a moisture content of from about 30 wt % to about 60 wt %, more typically from about 30 wt % to about 50 wt %, or even more typically from about 30 wt % to about 40 wt %.

Various methods and apparatus detailed elsewhere herein are suitable for treating and/or obtaining acid-impregnated feedstocks. In particular, the methods detailed elsewhere herein regarding impregnators as depicted in FIGS. 2-4 are suitable for preparing acid-impregnated feedstocks. Similarly, the apparatus (e.g., holding tanks) as depicted in FIGS. 5-10 are suitable for processes involving acid-impregnated feedstocks.

Generally, as with moisture-impregnation, feedstocks utilized for acid impregnation have a minimum moisture content such that a significant fraction of the feedstock surface has not become unavailable for acid-impregnation due to closing of feedstock particle pores by collapsing onto themselves. However, excessive starting moisture contents may impede acid impregnation. The issues attendant moisture impregnation are also considerations in acid impregnation. Thus, generally the moisture content of the feedstock to be subjected to acid impregnation is from about 5 to about 30 wt %, and preferably from about 10 wt % to about 20 wt % or from about 10 wt % to about 15 wt %.

Generally, the methods and apparatus detailed herein for acid-impregnation provide acid-impregnated cellulosic feedstocks having a moisture content of at least about 20 wt %, or at least about 30 wt %. Typically, the acid-impregnated cellulosic feedstock has a moisture content of from about 20 wt % to about 70 wt % and, more typically, of from about 30 wt % to about 70 wt %.

The temperature of the acidic liquid medium utilized for acid impregnation is typically from about 20° C. about 95° C., or from about 30° C. to about 75° C. Typically, the temperature of the acid-impregnated cellulosic feedstock is from about 20° C. to about 90° C., or from about 40° C. to about 80° C.

Generally, the acidic liquid medium has an acid concentration of less than about 4 wt %, less than about 3 wt % or less than about 2 wt %. Typically, the acidic liquid medium has an acid concentration of from about 0.7 wt % to about 3.5 wt % or from about 1.0 wt % to about 3.0 wt %.

Acid uptake by the feedstock (dry weight basis) is preferably from about 0.01 kg to about 0.05 kg acid per kg of feedstock, more preferably from about 0.02 kg to about 0.04 kg acid per kg of feedstock and, still more preferably, from about 0.02 kg to about 0.03 kg acid per kg of feedstock.

Generally, the holding tank apparatus detailed elsewhere herein, in particular those embodiments depicted in FIGS. 5-10 detailed above and elsewhere herein, are suitable for use in connection with moisture-impregnated feedstocks and acid-impregnated feedstocks.

For those embodiments where the apparatus is used in connection with moisture-impregnated feedstocks, the materials of construction of the apparatus are not narrowly critical. Generally, however, the apparatus may be constructed of low-grade stainless steel, carbon steel, or a polymeric material. For example, in those embodiments where the apparatus is constructed of a polymeric material it may be constructed of reinforced fiberglass, polyethylene, polypropylene, polytetrafluoroethylene, polyurethane, polyester, polyimide or a combination thereof.

In those embodiments wherein the apparatus is utilized in connection with acid-impregnated feedstocks, the apparatus is typically constructed of an acid-resistant steel or alloy. For example, in various embodiments the holding tank apparatus is constructed of stainless steel. Suitable stainless steels include those selected from the group consisting of 304 stainless steel, 304L stainless steel, 316 stainless steel, 316L stainless steel, 317 stainless steel, duplex stainless steel 2205, alloy 20 stainless steel, and combinations thereof. Alternatively, the apparatus may be constructed of plastic, carbon steel, or metal having an acid-resistant coating thereon. Suitable acid-resistant coatings include teflon, polypropylene, and combinations thereof.

Various embodiments of holding tanks of the present invention detailed elsewhere herein (e.g., as described in connection with FIGS. 5-10), generally include at least one sidewall having an upper portion and a lower portion, at least one inlet adjacent the upper portion, and at least one outlet adjacent the lower portion. In various embodiments, the lower portion defined by the sidewall has a greater cross sectional area than the upper portion defined by the sidewall. In this manner the at least one sidewall is arranged in a diverging manner relative to an axis perpendicular to the at least one inlet of the holding tank. That is, the at least one sidewall diverges along its length from the upper portion adjacent the at least one inlet toward the lower portion adjacent the at least one outlet. This arrangement of the sidewall(s) contributes to flow of the cellulosic feedstock downward (and optionally laterally) through the holding tank under the force of gravity, thereby avoiding bridging of the inlet and outlet of the holding tank with cellulosic feedstock. Arranging at least one sidewall in this manner has proven effective for this purpose. In various embodiments, at least one sidewall is arranged such that it neither converges nor diverges along its length from the inlet of the holding tank to the outlet of the holding tank. Having a plurality of sidewalls arranged in this manner defines a lower portion having a cross sectional area equal to the cross sectional area of the upper portion. Arrangement of the sidewall(s) in this manner is currently believed to be effective at avoiding interlocking and bridging of the feedstock at the inlet and outlet of the holding tank. In still further embodiments, the holding tank includes at least one sidewall that does not diverge or converge along its length from the inlet of the holding tank to the outlet of the holding tank and at least one sidewall that does diverge along its length from the inlet of the holding tank to the outlet of the holding tank (as shown in FIG. 5). In such embodiments, the lower portion defined by the sidewalls has a greater cross sectional area than the upper portion defined by the sidewalls.

In accordance with various embodiments of the present invention detailed above and elsewhere herein, from a vessel that preferably has a downwardly extending passage for the feedstock (e.g., the holding tank depicted in FIGS. 1-5), the cellulosic feedstock is directed to one or more downstream process units (e.g., auto- or acid-catalyzed hydrolysis reactors) followed preferably by one or more enzymatic hydrolysis reactors, positioned downstream from the holding tank apparatus such that the cellulose may be hydrolyzed to produce sugars that are suitable for fermentation to ethanol.

In various such embodiments, the holding tank apparatus operates as a discharge member in the form of a live bottom bin. Reference to a live bottom bin herein refers to an apparatus having an enclosed bottom or forming the bottom of the holding tank and including discharge members for removal of feedstock through one or more outlets or an apparatus including discharge members forming the bottom of the tank for conveying feedstock from the apparatus. One embodiment of such an apparatus is depicted in FIGS. 5-10. In addition to one or more screw conveyors as the discharge member as depicted in FIGS. 5-10, the apparatus may include one or more paddle conveyors as the discharge member including, for example, those described in connection with the impregnators detailed elsewhere herein and described in connection with FIGS. 2-4. Additionally or alternatively, the discharge member may include one or more sweeping conveyors, one or more sweeping arms, or one or more rotational disk apparatus and a suitable outlet or opening in the base of the tank for removal of feedstock from the tank. In those embodiments wherein the discharge members form the bottom of the holding tank, or live bottom bin, preferably the discharge members comprise one or more metering screws for passage of feedstock through the bottom of the tank. In alternate embodiments, the discharge members comprise one or more paddle conveyors (e.g., as described in connection with the impregnators detailed elsewhere herein and described in connection with FIGS. 2-4).

Further in accordance with those embodiments in which the discharge member passes treated feedstock through an outlet of a live bottom bin, the apparatus typically comprises comprising one or more collection and conveyance members in communication with the discharge member. Generally, the collection and conveyance members include one or more screw conveyors (e.g., one or more rotatably mounted helical screws), one or more paddle conveyors, one or more belt conveyors, one or more drag chain conveyors, or one or more tubular conveyors. In various preferred embodiments, each outlet of the live bottom bin feeds material to a single collection and conveyance member. Generally, the collection and conveyance member conveys the feedstock toward a hydrolysis reactor (e.g., an auto- or acid-catalyzed hydrolysis reactor). In various preferred embodiments, the collection and conveyance member is enclosed to prevent moisture loss from the feedstock, to prevent loss of volatile components of the feedstock (e.g., loss of acid from an acid-impregnated feedstock), and/or prevent contamination of the feedstock.

Various embodiments of the present invention are directed to an apparatus for conveying an acid-impregnated cellulosic feedstock generally comprising a holding tank, an impregnation chamber or vessel, and a hydrolysis reactor. The holding tank, impregnation chamber or vessel, and hydrolysis are generally constructed as detailed elsewhere herein including, for example, the impregnators detailed in connection with FIGS. 2-4 and the holding tank detailed in connection with FIGS. 5-10. In various embodiments, the holding tank generally comprises (i) a plurality of sidewalls defining a passage having an upper portion having a cross sectional area and a lower portion having a cross sectional area, (ii) at least one inlet adjacent the upper portion, (iii) at least one outlet adjacent the lower portion, at an elevation below the inlet, and (iv) at least one discharge member comprising a base and an open top that is at least as large as, and is in vertical registration with, the at least one outlet, and the holding tank is constructed of acid-resistant materials. Further in accordance with such embodiments, the holding tank is in fluid communication with the impregnation chamber or vessel and/or hydrolysis reactor, and preferably is in fluid communication with both the impregnation chamber or vessel and the hydrolysis reactor. In accordance with various embodiments, the cross sectional area of the lower portion is at least equal to the cross sectional area of the upper portion. More particularly in accordance with such embodiments, the holding tank, impregnation chamber or vessel, and hydrolysis reactor are arranged in a closed system particularly suitable for use with acid-impregnation to avoid escape of volatile components from the system (e.g., acid of the acidic liquid medium and of the impregnated feedstock).

V.

Embodiments of the present invention provide a method and apparatus for treating a cellulosic feedstock that may be used for subsequent ethanol production. The method and apparatus of a preferred embodiment serve to mix the feedstock, and optionally to heat and/or moisten the cellulosic feedstock, to obtain a relatively uniform temperature and moisture level or profile of the feedstock, while reducing, and preferably essentially preventing, the charring or other degradation of the cellulose and hemicellulose during this heating stage. Accordingly, the method and apparatus provide a cellulosic feedstock, which is suitable for the production of a fermentation precursor stream. The cellulosic feedstock may be subsequently treated to liberate sugars in the cellulose and hemicellulose and produce a sugar stream that may then be subjected to fermentation to obtain a high yield alcohol stream.

Figure 11:
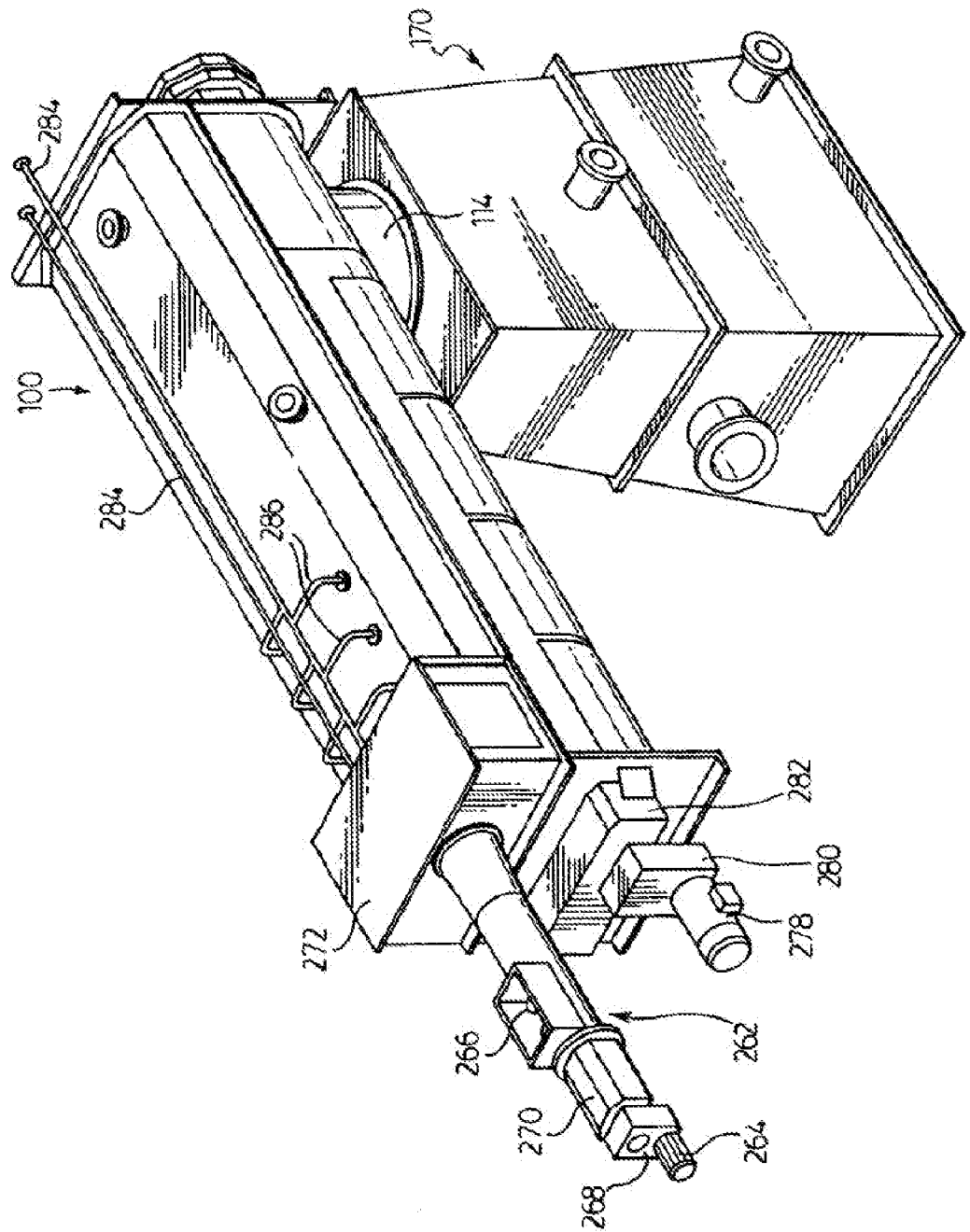
FIG. 11 is a perspective illustration of an embodiment of an apparatus of the present invention.

An embodiment of an apparatus 100 of the present invention is shown in FIGS. 11-17D. In this embodiment, apparatus 100 is configured to convey a cellulosic feedstock, for example from a holding tank or a moisture addition determination stage wherein the amount of moisture in the feedstock is determined and the amount of moisture required to obtain a predetermined moisture content is determined, to an autohydrolysis reactor. An alternate embodiment of apparatus 100 of the present invention is shown in FIG. 11. In this embodiment, apparatus 100 is further configured to convey the cellulosic feedstock while providing heat and/or moisture to the cellulosic feedstock, for example to maintain a desired temperature and moisture content of the cellulosic feedstock, by providing moisture, preferably heated moisture, to the central portion of the apparatus.

It will be appreciated that although the method is described with reference to apparatus 100 and vice versa, the method may be carried out with an alternate apparatus, and apparatus 100 may be used according to an alternate method. Furthermore, although the method is described as a continuous process, it will be appreciated that the method may be carried out as a semi-continuous or batch process.

Generally, when the cellulosic feedstock is provided, it will have an initial or starting moisture content. The initial moisture content may depend on numerous factors, such as the nature of the cellulosic feedstock, and any upstream storage conditions. In some embodiments, the initial moisture content is less than about 15 wt % and, preferably, from 5-15 wt %. In some embodiments, at least some moisture may be provided in advance of the apparatus. If no moisture is added in apparatus 100, then the initial moisture content may be from 40-50 wt %.

Referring to FIGS. 11-14, apparatus 100 comprises an enclosed volume or chamber 102, which has a length L, along which the cellulosic feedstock is conveyed. Length L may vary depending on the particular embodiment, and in some embodiments may be between about 10 ft and about 30 ft.

In some embodiments, an impregnator feeder 262, namely a feeder that conveys feedstock into chamber 102, is preferably positioned upstream of mixing or impregnation chamber 102. Feeder 262 may be of any design. Preferably, feeder 262 is of a design that inhibits, and preferably prevents, the flow of moisture upstream of feeder 262. For example, a rotating valve or the like may be provided to segment such upstream flow. Preferably impregnation feeder is a screw feeder comprising a motor 264 drivingly connected to a screw or auger 266 positioned below an inlet, such as via a transmission or gear reduction assembly provided in housing 268. The shaft on which screw 266 is provided may be rotatably mounted in housing 270 such that auger 266 is a cantilevered plug screw conveyor. Accordingly, feeder 262 produces a plug of material that prevents upstream migration of moisture. The plug may be conveyed into inlet housing 272 that is mounted, e.g., to outer wall 105 and positioned above inlet 101 to chamber 102. The feedstock may then pass downwardly into chamber 102.

In the embodiment shown, chamber 102 is defined by a shell, which is preferably provided with a heating jacket 160. Accordingly, the shell preferably comprises an inner wall 104 having an inner surface 109 and a spaced apart outer wall 105 defining a volume 162 therebetween. Accordingly, chamber 102 may be a double walled chamber having a volume 162 through which a heated fluid may be passed from an inlet to an outlet. Accordingly, the heated fluid circulates within enclosure 162, and provides heat to the cellulosic feedstock. The heated fluid may be water, for example, or steam. For example, if steam is not used to provide heat to the fibers in the treatment chamber, but water at, e.g., 50-60° C. is used, the feedstock will be heated but will not be raised to a temperature at which degradation may occur. Preferably, the temperature of water in the heating jacket is from 70 to 90° C., preferably from 75 to 85° C. Any heating jacket or the like known in the art may be used. Alternately, a heating jacket need not be used or may only surround a portion of the inner wall 104. In such a case, inner wall may be the only wall surrounding volume 102.

In the embodiment shown, the cellulosic material is preferably conveyed towards a holding tank 170 after exiting chamber 102. Apparatus 100 comprises at least one inlet 101, and at least one outlet 103, positioned at opposed ends of volume 102. Preferably inlet 101 is defined in upper surface 108, and outlet 103 is defined in the lower surface, such that cellulosic material may be deposited into enclosed volume 102 via inlet 101, be conveyed along length L of enclosed volume 102, and drop out of enclosed volume 102 via outlet 103 and travel downwardly to holding tank 170, such as via passage 114.

Chamber 102 has a lower surface that is configured such that conveyance members 130 may sweep adjacent all of, or much of, the lower wall to reduce the likelihood of material having an increased residence time by not being conveyed through chamber 102. Accordingly, the lower surface and the conveyance member are configured so as to sweep the lower surface. In the exemplified embodiment, the lower surface is scallop shaped and the conveyance member has paddles that are positioned and configured to sweep the trough of each scallop shaped surface. Other shapes may be used provided that one or more conveyance members has a configuration that is compatible with the shape of the lower surface.

Figure 15A:
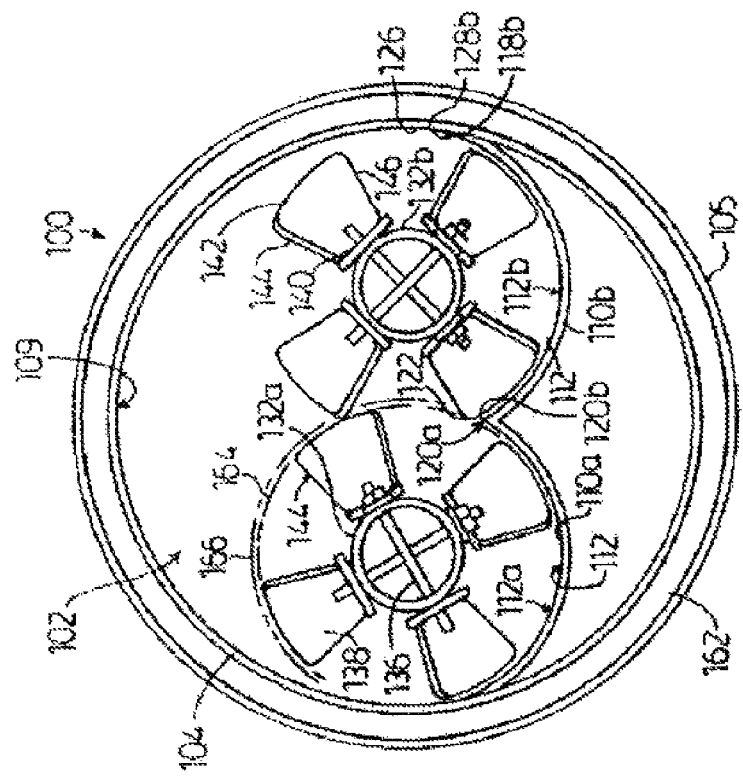
FIGS. 15A and 15B are transverse cross-sections taken along line 5-5 in FIG. 12, showing various rotational positions of an embodiment of a conveyance member of the present invention.
Figure 15B:
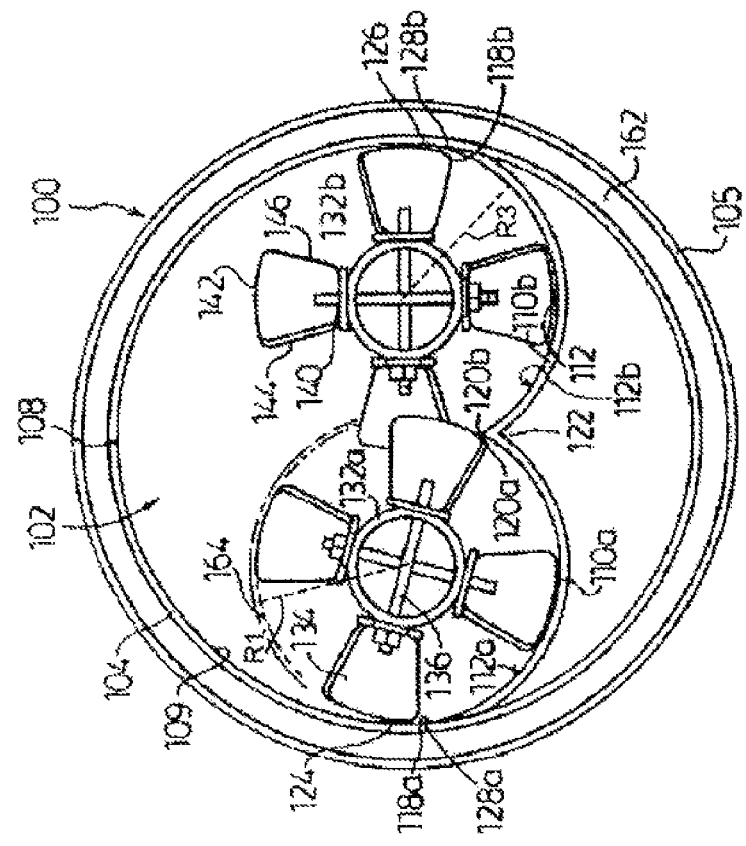

Referring still to FIGS. 15A and 15B, enclosed volume 102 is exemplified as a lower surface comprising a plurality of longitudinally extending portions 110 and an upper surface 108. Each portion may be a wall section that is added to the inside of inner wall 104. As exemplified, lower surface comprises two portions, 110a, and 110b. In other embodiments, lower surface may comprise greater than two portions. For example, lower surface may comprise three portions. Portions 110a, 110b each have an inner surface 112a, 112b that is preferably arcuate in transverse section. That is, when viewed in transverse section in FIGS. 15A and 15B, the inner surface of each portion 110a, 110b defines an arc. In the embodiments shown, each arc is a circular arc (i.e., defines a sector of a circle), and the radius R1 of each arc is preferably essentially identical. However, in alternate embodiments, one or more of the arcs may be an elliptical arc, and the arcs may have non-identical radii.

Each of the inner surfaces 112a, 112b has an upper outer side 118a, 118b, and an upper inner side 120a, 120b. In the embodiments shown, the upper inner sides 120a, 120b meet at an apex 122. That is, portions 110a and 110b are side-by-side. In alternate embodiments, the upper inner sides 120a, 120b may be spaced apart and the lower surface of chamber 102 may further comprise a third portion extending between upper inner sides 120a, 120b. An advantage of providing an apex 122 is that feedstock will tend not to be retained on the lower surface between adjacent the arcs.

As exemplified in FIGS. 15A and 15B, upper surface 108 comprises a longitudinally extending wall having an inner surface 109 that is arcuate (e.g., semi cylindrical). In alternate embodiments, upper surface 108 may have an inner surface that, for example, comprises a plurality of longitudinally extending portions (e.g., be scallop shaped similar to portions 110) or may have an inner surface that is flat in transverse section.

As exemplified in FIGS. 15A and 15B, inner surface 109 has first transversely opposed lower side 124 and second transversely opposed lower side 126, which are longitudinally extending. The first side 124 of upper surface 108 meets or merges with upper outer side 118a at point 128a, and the second side 126 of upper surface 108 meets or merges with upper outer side 118b at point 128b. In the embodiments shown, the sides meet at the portions denoted by reference numerals 128a and 128b in a substantially smooth fashion. However in alternate embodiments, the sides may meet in a substantially abrupt fashion.

Apparatus 100 further comprises one or more conveyance members 130 which are provided within enclosed volume 102. Preferably, a conveyance member is associated with each portion 110 of the lower surface. As exemplified, a conveyance member 130 is centered above each inner surface 112 of a portion 110 (e.g., the longitudinal axis of each conveyance member is coaxial with the longitudinal axis of the centre of a circle described by its associated portion 110). Accordingly, in the embodiments shown, apparatus 100 comprises a first conveyance member 130a associated with inner surface 112a, and a second conveyance member 130b associated with inner surface 112b. In alternate embodiments apparatus 100 may comprise greater than two conveyance members, depending on the configuration of lower surface 112. Each conveyance member 130 is configured to convey cellulosic material longitudinally through volume 102 by sweeping its respective inner surface 112. That is, each conveyance member 130 is configured such that at least a portion thereof passes over an inner surface 112 in a continuous motion to push the cellulosic material forwardly (i.e., in a direction away from inlet 101 and towards outlet 103).

Figure 14:
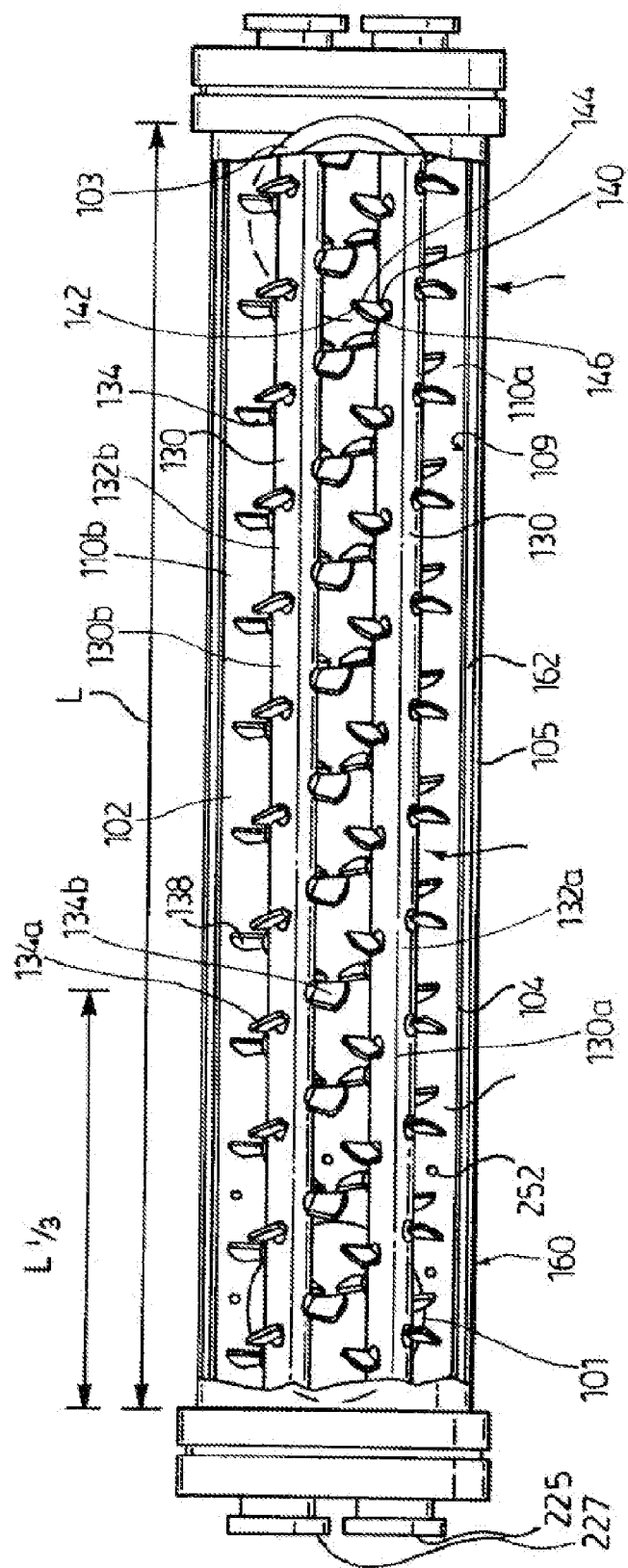
FIG. 14 is a top view of the apparatus of FIG. 11, with the upper portion of the apparatus removed, showing the interior of the apparatus.
Figure 16:
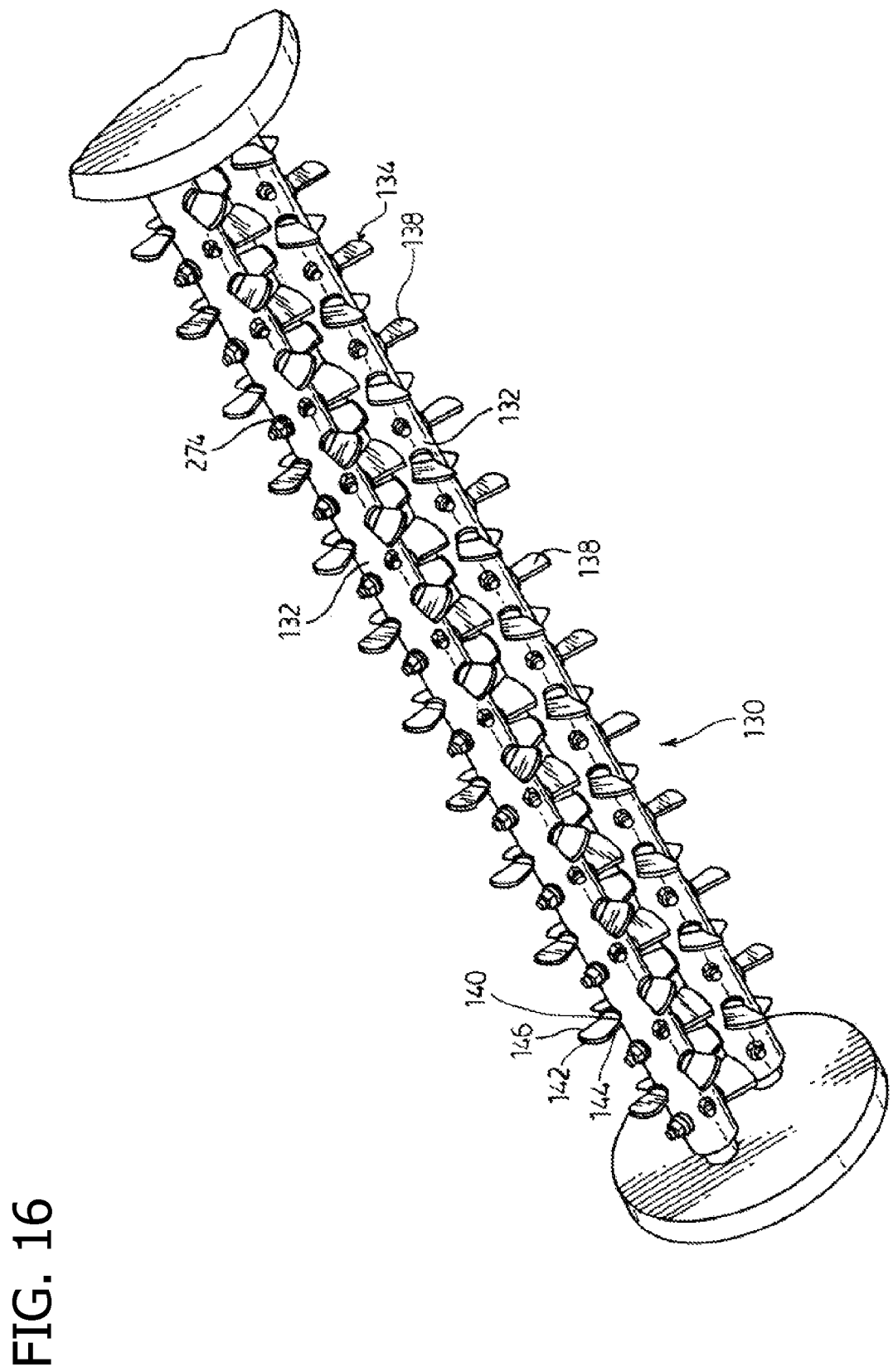
FIG. 16 is a perspective illustration of an embodiment of a conveyance member of the present invention.

Referring to FIGS. 14-16, in the embodiments shown, in order to sweep its respective inner surface, each conveyance member 130 comprises a longitudinally extending rotary shaft 132a, 132b. The rotary shafts 132a, 132b are adjacent and spaced transversely apart from each other, and are generally parallel. One or more conveying members, such as a plurality of paddles 134, extend outwardly from each shaft 132. As exemplified in FIGS. 17A-17D, the paddles each comprise a stem 136, which is coupled to the rotary shaft, and a generally planar blade 138, which extends from and is attached to each stem 136. Each blade 138 comprises a radial inner edge 140 which is attached to a stem 136, a radial outer edge 142 opposite the radial inner edge, and opposing first side edge 144 and second side edge 146 extending between the inner and outer edges 140, 142.

Preferably, as exemplified in FIG. 14, the paddles 134 are staggered axially and circumferentially along each shaft 132, such that they are generally arranged helically around each shaft 132. In other words, a helix would be defined if the radial outer edge 142 of paddles were connected by a line extending from the inlet end of a rotary shaft to the outlet end thereof. Accordingly, helically adjacent paddles 134, for example paddles 134a and 134b, extend from the shaft at different angular positions around the shaft axis, as can be seen in FIG. 14.

Preferable, each blade 138 is canted, such that a first side edge 144 is axially nearer outlet 103 and rotationally trailing relative to a second side edge 146.

Additionally, when viewed axially along the length of a rotary shaft, the first side edge 144 of one paddle 134a axially overlaps the second side 146 edge of an adjacent paddle 134b.

Accordingly when the rotary shafts 132 rotate, paddles 134 pass over inner surfaces 112 in a continuous motion to push the cellulosic material forwardly. An advantage of the exemplified design is that the outer radial edges of the blades are configured to travel a generally consistent distance above longitudinally extending portions 110, thereby being able to effectively sweep longitudinally extending portions 110.

In alternate embodiments, the paddles may be otherwise configured. For example, they may not be canted, and may be wedge shaped. Additionally, they may, for example, be arranged in a grid around shaft 132, rather than in a helix. It will be appreciated that in a particularly preferred embodiment, the paddles are arranged to define a helix, the blades are canted and the first side edge of one paddle axially overlaps the second side edge of a next adjacent paddle. However, these features may be used in any particular sub-combination.

Figure 12:
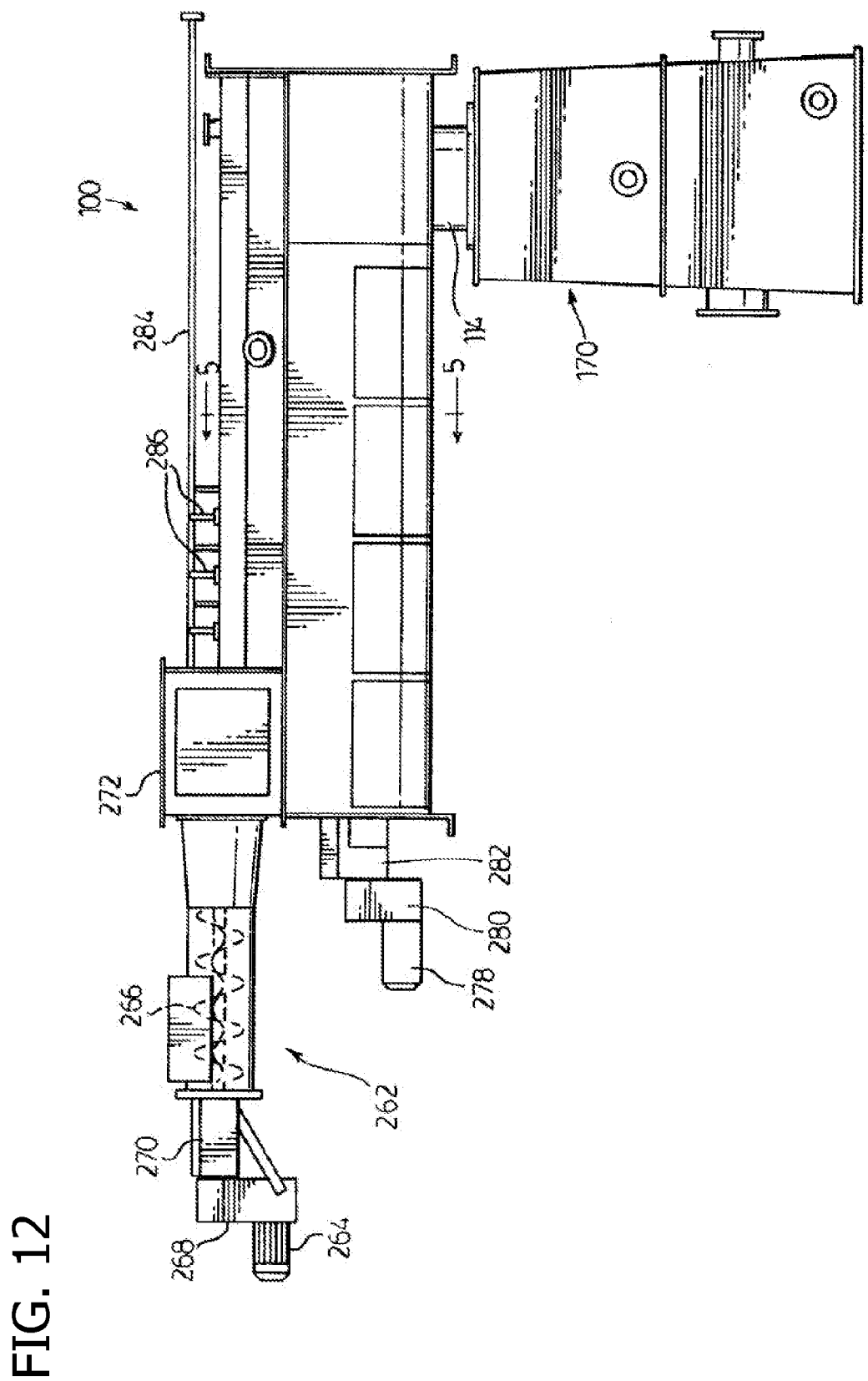
FIG. 12 is a front plan view of the apparatus of FIG. 11.
Figure 13:
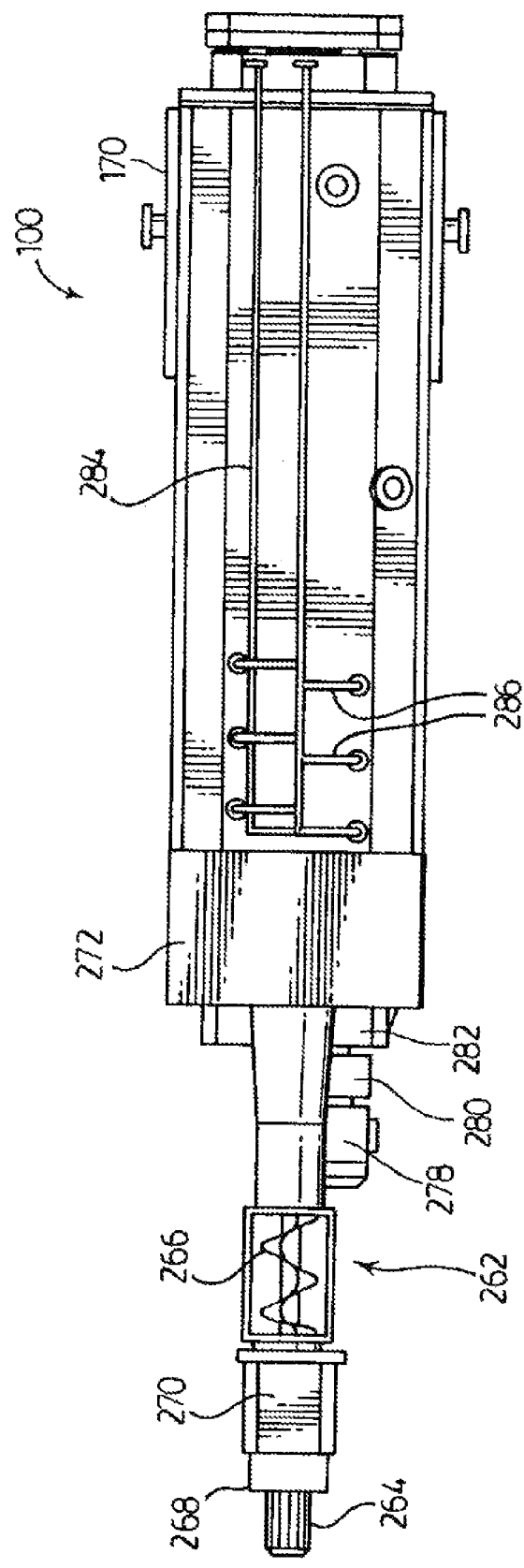
FIG. 13 is a top plan view of the apparatus of FIG. 11.

As exemplified in FIGS. 11-13, conveyance members 130 are rotatably mounted in chamber 102 and are drivenly connected to a motor 278. As exemplified, motor 278 is drivingly connected to conveyance members 130 via a transmission or gear reduction assembly provided in housing 280. The gear reduction assembly may be drivingly connected to ends 225, 227 of conveyance members 130 that are positioned inside housing 282. However, conveyance members 130 may be rotatably mounted by any means known in the art.

Rotary shafts 132a, 132b are preferably configured to rotate in opposite direction, but may rotate in the same direction.

It will be appreciated that, in alternate embodiments, conveyance members 130 may be otherwise configured. For example, conveyance members 130 may comprise an auger such that the conveying member is a continuous or discontinuous screw mounted on a shaft, which extends along enclosed volume 102, and which is rotated to urge the cellulosic feedstock through volume 102 and sweep inner surfaces 112.

In accordance with this particularly preferred aspect, paddles 134 and portion 110 are configured such that when a given paddle is adjacent and passing over surface 112, a substantially constant distance is maintained between the outer edge 142 of the paddle 134, and surface 112. Such embodiments may aid in ensuring that the cellulosic material is urged forwardly at a substantially constant rate, and that the cellulosic material is not retained in the chamber.

For example, in the embodiments shown, the outer edge 142 of each blade 138 is curved or arcuate in shape (see for example FIG. 17B), and the curve matches an arc 148 swept or defined by the outer edge 142 as the shafts 132 rotate. That is, outer edge 142 of each blade 138 is curved to define a sector of a circle having a radius R2. When shafts 132 rotate, the outer edge 142 of each blade 138 will describe a sector of a circle 164 having a radius R3. In embodiments wherein blades 138 are not canted, for example wherein blades 138 are wedge shaped, R3 will equal R2. In embodiments wherein blades 138 are canted, R3 will be less than R2.

Further, longitudinally extending portion 110 is configured such that the inner surface 112 defines an arc of a circle 166 of radius R1 in transverse section. The blades are configured such that R3 is less than, e.g., about 6.5 mm smaller than R1. Accordingly, when shafts 132 rotate, and a given paddle 134 is adjacent and passing over a lower inner surface 112, a substantially constant distance is maintained between the outer edge 142 of the blade 138 of the paddle 134, and the inner surface 112. Preferably, R1 and R3 are essentially the same (i.e. R3 is less than R1 by a small tolerance factor), such that when a given paddle 134 is adjacent and passing over a lower inner surface 112, outer edge 142 and inner surface 112 remain in close proximity. Such embodiments may aid in ensuring that the cellulosic material is urged forwardly at a substantially constant rate, and that the cellulosic material does not get stuck in the chamber. The spacing between radial outer edge 142 and the arc defined by surface 112 may be from 5 mm to 10 mm. The spacing may vary depending upon the size of the particulate matter in the feedstock. The larger the size of the particulate matter, the larger the spacing may be. Preferably, the spacing is less than the maximum particle size and, more preferably, less than the median particle size. Accordingly, as the shafts rotate, particulate matter will be continually moved through the chamber. Further, if longitudinally extending portions 110 are heated, then the particulate matter will be inhibited from staying in the same location and being possibly overheated such that cellulose or hemicellulose is degraded by heat.

Preferably, as exemplified in the embodiments shown in FIGS. 11 to 17, apparatus 100 is further configured to mix the cellulosic material as it is conveyed. That is, if rotary shafts 132 are operated at a high enough speed, for example about 55 rpm, blades 138 of paddles 134 will not only push cellulosic material along surfaces 112, but will also project cellulosic material upwardly, such that it intermingles with cellulosic material located forwardly or rearwardly of it within enclosed volume 102.

It will be appreciated that the conveyance member 130 preferably rotates at from 40 to 150 and, more preferably, about 45 to 75 rpm. Alternately, or in addition, the chamber may operate at a low fill factor, for example from 10 to 50 and preferably about 15 to 30%. Accordingly, a majority of the volume in chamber 102 may be filled with air. For example, if the fill factor is 30%, then only 30% of the volume of chamber 102 is filled with feedstock, the rest being filled with preferably air. As the conveyance member rotates, preferably at a relatively high speed, the feedstock will be thrown up into the empty upper portion of chamber 102 thereby mixing the feedstock to provide a more uniform distribution of heat and/or moisture throughout the feedstock. It will be appreciated that the use of a high rotational speed, combined with a low fill factor permits the use of a higher temperature in the heating jacket and/or in the temperature of the moisture provided to the feedstock in the chamber with reduced risk of heat degradation of the feedstock.

Preferably the air in chamber 102 is at a temperature of about 60 to 70° C. and about saturated.

In some embodiments, apparatus 100 is further configured to treat the cellulosic material as it is conveyed through enclosed volume 102. For example, apparatus 100 may be configured to heat, and/or moisten the cellulosic material as it is conveyed through enclosed volume 102.

For example, referring to FIGS. 18A-18D, an alternate embodiment of conveyance members 130 is shown. In this embodiment, conveyance members 130 comprise fluid injection ports, for adding moisture to the cellulosic material. In the embodiments shown, injection ports 252 are defined in blades 138 of paddles 134; however, in alternate embodiments, injection ports 252 may alternately or in addition be provided in stems 136 and/or in shafts 132. As shown, injection ports 150 extend inwardly from an outer surface of blades 138, and are in fluid communication with one or more paddle ducts 252 provided within paddles 134. The one or more paddle ducts 152 are in fluid communication with a fluid conduit 256, extending through shafts 132, for example via ports 258 provided in stem 136. Fluid conduit 256 is in fluid communication with a moisture source (not shown), for example at ends 225, 227 of shafts 132. Accordingly, as the conveyance member rotates moisture, may be introduced into volume 102 by passing from a moisture source into fluid conduit 256, through ports 258 in stem 136, through passage 254 and out of ports 252 in blades 138.

In alternate embodiments (not shown), the injection ports 252 may additionally or alternately be provided in lower surface 106 and/or upper surface 108 and/or in the outer wall of shafts 132. For example, in some embodiments, injection ports 252 are provided along the entire length L of chamber 102. In other embodiments, moisture injection ports 252 are preferably provided only in an upstream portion of chamber 102, preferably in the upstream half of the length L of chamber 102 and, more preferably in the first or upstream third $L_{1/3}$ of the length L of chamber 102 (see FIG. 14). For example, as exemplified in FIG. 11, a plurality of injection ports may be provided in the upper portion of chamber 102. As shown therein, one or more conduits 284 may convey water to a plurality of branch conduits 286 extending to different locations on the upper portion of chamber 102. The end of these conduits are in fluid flow communication with the interior of chamber 102, via a moisture addition member such as a nozzle or an open ended pipe or the like. As exemplified, six ports are provided. However, additional or fewer ports may be used. Accordingly, moisture injection ports may additionally or alternately be provided in the wall of chamber 102. That is, injection ports 252 may extend through inner wall 104.

The moisture may be added to the cellulosic material as liquid water, or may alternately be added as steam. Additionally, the water may not be pure water, and may comprise additional components. For example, one or more catalysts, including but not limited to mineral and organic acids, bases such as sodium hydroxide, organic solvents, and oxidizing agents such as hydrogen peroxide, may be added with the water.

Alternately, or in addition, in further embodiments as discussed, a heating jacket 160 may be provided. The heating jacket may be configured to heat upper surface 108 and/or lower surface (portions 110). It is preferred not to use steam since steam may result in the overheating of the cellulose and hemicellulose, causing degradation thereof. However, if the particularly preferred design exemplified herein is used, then higher temperatures may be used with reduced risk of degradation of the feedstock.

Alternately, or in addition, in other embodiments, the cellulosic feedstock may be heated by circulating steam in the conveyance member 132, for example, in paddles 138. In such embodiments the ports 252 are not provided.

Alternately, or in addition, in other embodiments, the cellulosic feedstock may be heated directly. For example, if moisture is being added to the cellulosic material, heated water or steam may be added as part of the moisture. For example, water may be at a temperature of 50 to 75° C. and preferably 65 to 70° C.

Blade 138 may be secured to one end of stem 136 by any means known in the art, such as welding, or mechanical affixation members such as rivets, or screws. The other end of stem 136 may be provided with a screw thread 276 on which bolt 274 may be received. Stem 136 may be secured to shaft 132 such as by extending transversely through shaft 132 from one side to the other and bolt 274 secured thereon. Suitable packing, gaskets or the like may be provided to limit or prevent moisture leaking out of shaft 132 past stem 136. Stem 136 may be provided with one or more openings 258 in fluid communication with volume 256 inside shaft 132. Accordingly, moisture may flow through shaft 132, through passage 254 in stem 136 to paddle 138 and out through ports 252 into chamber 102. However, paddles 138 may be directly secured to shafts 132 or may be secured by any other means known in the art.

An embodiment of a method of the present invention will presently be described. Although the method will be described with reference to apparatus 100, it will be appreciated that the method may utilize an alternate apparatus, and the method is not limited to use with a particular apparatus.

The method serves to at least mix, and preferably to also heat and mix or moisten and mix, and more preferably to mix, heat and moisten the cellulosic feedstock while it is conveyed. The method may serve to maintain the temperature and/or moisture content of the cellulosic feedstock, or to pretreat the cellulosic feedstock to render the cellulose of the feedstock ready for a downstream process such as one or more of autohydrolysis, enzymatic hydrolysis, and subsequent ethanol production. Such further pre-treatment processes may include incubation at an elevated temperature, for example in holding tank 170, shown hereinabove.

A cellulosic feedstock being less than 100% saturated with moisture, preferably less than 50% moisture on a weight basis is introduced into a longitudinally extending volume, and is conveyed through the longitudinally extending volume while heating the cellulosic feedstock.

For example, in order to introduce the cellulosic feedstock into a longitudinally extending volume, the cellulosic feedstock may be deposited into inlet 101 of apparatus 100. Preferably, the cellulosic feedstock is introduced into enclosed volume 102 of apparatus 100 such that the enclosed volume 102 is operated at less than 100% fill volume. Preferably at least half of the volume 102 is left empty. That is, the rate at which the cellulosic feedstock is introduced into enclosed volume 102 is preferably selected such that an upper portion of enclosed volume 102 is open during the operation of apparatus 100.

After being introduced into the longitudinally extending volume, the cellulosic feedstock is conveyed through the longitudinally extending volume. For example, in embodiments wherein apparatus 100 is utilized, the cellulosic feedstock is conveyed along the length of volume 102. In such embodiments, wherein apparatus 100 comprises longitudinally extending portions 110 having arcuate inner surfaces 112, arcuate inner surfaces 112 are preferably swept as feedstock is conveyed upwardly into the empty portion of the volume to enhance mixing and heat transfer. In other embodiments, the cellulosic feedstock may be mixed in another manner, for example by agitating a portion of the enclosed volume.

Accordingly, in some embodiments, the cellulosic feedstock is conveyed by sweeping a lower surface of the enclosed volume. For example, in embodiments wherein apparatus 100 is utilized, conveyance members 130a and 130b may be rotated to pass paddles 134 proximate inner surfaces 112a and 112b in a continuous motion to contact the cellulosic feedstock and urge the cellulosic feedstock along the length of each inner surface 112.

While the cellulosic feedstock is conveyed through the enclosed volume, it is preferably heated. In some embodiments, the cellulosic feedstock is heated to between about 50° C. to about 70° C. as it travels through the volume. That is the temperature of the feedstock is between about 50° C. to about 70° C. when it exits the enclosed volume. Preferably, the cellulosic feedstock is provided to the enclosed volume at less than about 30° C., and is heated to at least about 65° C. as it travels through the volume.

The cellulosic feedstock may be heated in a variety of ways. In some embodiments, wherein apparatus 100 is utilized, the feedstock may be heated by heating a surface of enclosed volume 102, a portion of conveyance members 130, and/or by providing heated water to the cellulosic feedstock.

The residence time of the cellulosic feedstock in the enclosed volume may vary. In some embodiments, the residence time may be less than about 10 minutes.

When the cellulosic feedstock exits the enclosed volume, it may be directed either directly or indirectly to a downstream hydrolysis, preferably, autohydrolysis process. For example, the cellulosic feedstock may be directed to a holding tank, for example holding tank 170 shown in FIGS. 11 and 12, such that it may be held at an elevated temperature to further pre-treat the cellulosic feedstock, and from the holding tank to an autohydrolysis reactor.

VI.

Embodiments of the present invention provide a method and apparatus for treating a cellulosic feedstock for subsequent ethanol production. The method and apparatus of a preferred embodiment serve to heat and moisten the cellulosic feedstock to obtain a relatively uniform temperature and moisture level of the feedstock, while reducing, and preferably essentially preventing, the charring or other degradation of the cellulose and hemicellulose during this heating stage. Accordingly, the method and apparatus provide a cellulosic feedstock, which is suitable for the production of a fermentation precursor stream. The cellulosic feedstock may be subsequently treated to liberate sugars in the cellulose and hemicellulose and produce a sugar stream that may then be subjected to fermentation to obtain a high yield alcohol stream. An embodiment of an apparatus of the present invention is shown in FIGS. 19-26D. It will be appreciated that although the method is described with reference to apparatus 200 and vice versa, the method may be carried out with an alternate apparatus, and apparatus 200 may be used according to an alternate method. Furthermore, although the method is described as a continuous process, it will be appreciated that the method may be carried out as a semi-continuous or batch process.

Generally, when the cellulosic feedstock is provided, it will have an initial or starting moisture content. The initial moisture content may depend on numerous factors, such as the nature of the cellulosic feedstock, and any upstream storage conditions. In some embodiments, the initial moisture content is less than about 15 wt % and, preferably, from 5-15 wt %. In some embodiments, at least some moisture may be provided in advance of the apparatus.

The method comprises conveying the cellulosic feedstock through an enclosed volume. The enclosed volume may be of a variety of configurations. Referring to FIGS. 19-23B, in the embodiment shown, chamber 204 of apparatus 200 comprises an enclosed volume 202. Chamber 204 may be referred to as an impregnation chamber, or a treatment chamber.

In the embodiment shown, chamber 204 is defined by a shell 206, which preferably is provided with a heating jacket 260. Accordingly, shell 206 preferably comprises an inner wall 208 and a spaced apart outer wall 209 defining a volume 207 therebetween. Accordingly, chamber 204 may be a double walled chamber having a volume 207 through which a heated fluid may be passed from, e.g., inlet to the volume 207 to the outlet from the volume. Wall 208 has an inner surface 210 that encloses chamber 204. It will be appreciated that a single walled vessel may be used. It will be appreciated that heating jacket 260 may surround only part of chamber 204 and may be of any design.

In some embodiments, an impregnator feeder 262, namely a feeder that conveys feedstock into chamber 204, is preferably positioned upstream of mixing or impregnation chamber 204. Feeder 262 may be of any design. Preferably, feeder 262 is of a design that inhibits, and preferably prevents, the flow of moisture upstream of feeder 262. For example, a rotating valve or the like may be provided to segment such upstream flow. Preferably impregnation feeder is a screw feeder comprising a motor 264 drivingly connected to a screw or auger 266 positioned below an inlet, such as via a transmission or gear reduction assembly provided in housing 268. The shaft on which screw 266 is provided may be rotatably mounted in housing 270 such that auger 266 is a cantilevered plug screw conveyor. Accordingly, feeder 262 produces a plug of material that prevents upstream migration of moisture. The plug may be conveyed into inlet housing 272 that is mounted, e.g., to outer wall 209 and positioned above inlet 211 to volume 202. The feedstock may then pass downwardly into chamber 204.

Chamber 204 comprises at least one feedstock inlet 211, and at least one treated feedstock outlet 213, which may be positioned above outlet passage 218. Inlet 211 and outlet 213 are spaced axially apart to define a length L. Length L may vary depending on the particular embodiment, however, in some embodiments, length L may be between about 8 ft and about 12 ft. In the embodiment shown, inlet 211 is defined in upper portion of shell 206, and outlet 213 is defined in lower portion of shell 206. Accordingly, the cellulosic feedstock is deposited into inlet 211, is conveyed along the length of chamber 204 and drops out of outlet 213 into optional outlet passage 1218, which is upstream of optional heated holding tank 221. In alternate embodiments, inlet 211 and outlet 213 may be positioned elsewhere, for example at opposed ends of chamber 204.

In one aspect of the invention, chamber 204 may be of any configuration that provides a residence time for the feedstock to be treated (heated and/or provided with moisture) so as to obtain a treated feedstock having a moisture level and a temperature within a predetermined range, and which is preferably uniform for the feedstock exiting the chamber.

In one particularly preferred aspect, and preferably in combination with the forgoing aspect, the chamber and a conveyance member 222 are configured such that the feedstock is moved through the chamber with a relatively constant residence time. Preferably, the chamber and a conveyance member 222 are configured such that the lower surface on which the feedstock may rest under the influence of gravity is swept such that feedstock will be continually urged through the chamber.

Figure 19:
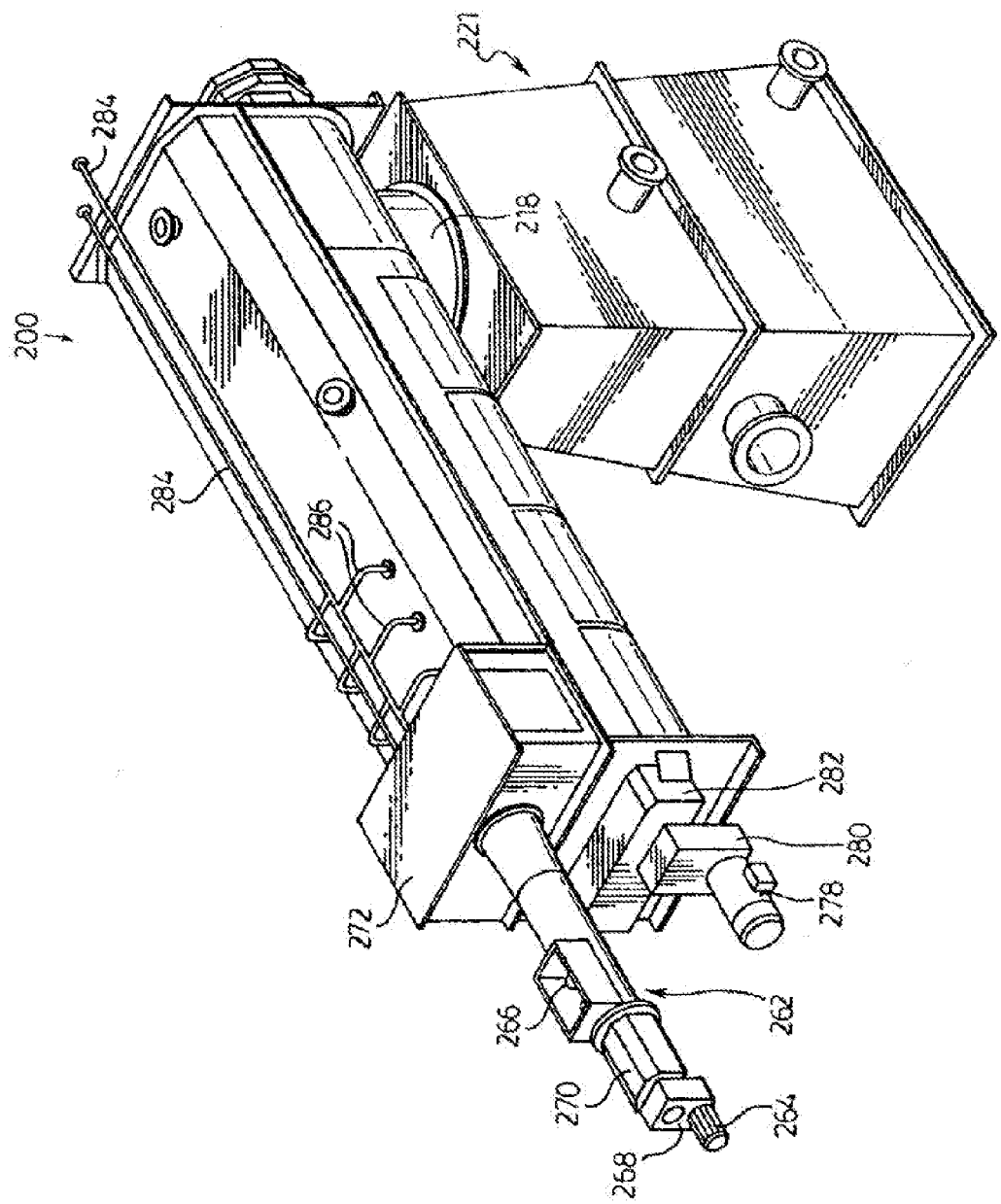
FIG. 19 is a perspective illustration of an embodiment of an apparatus of the present invention.
Figure 20:
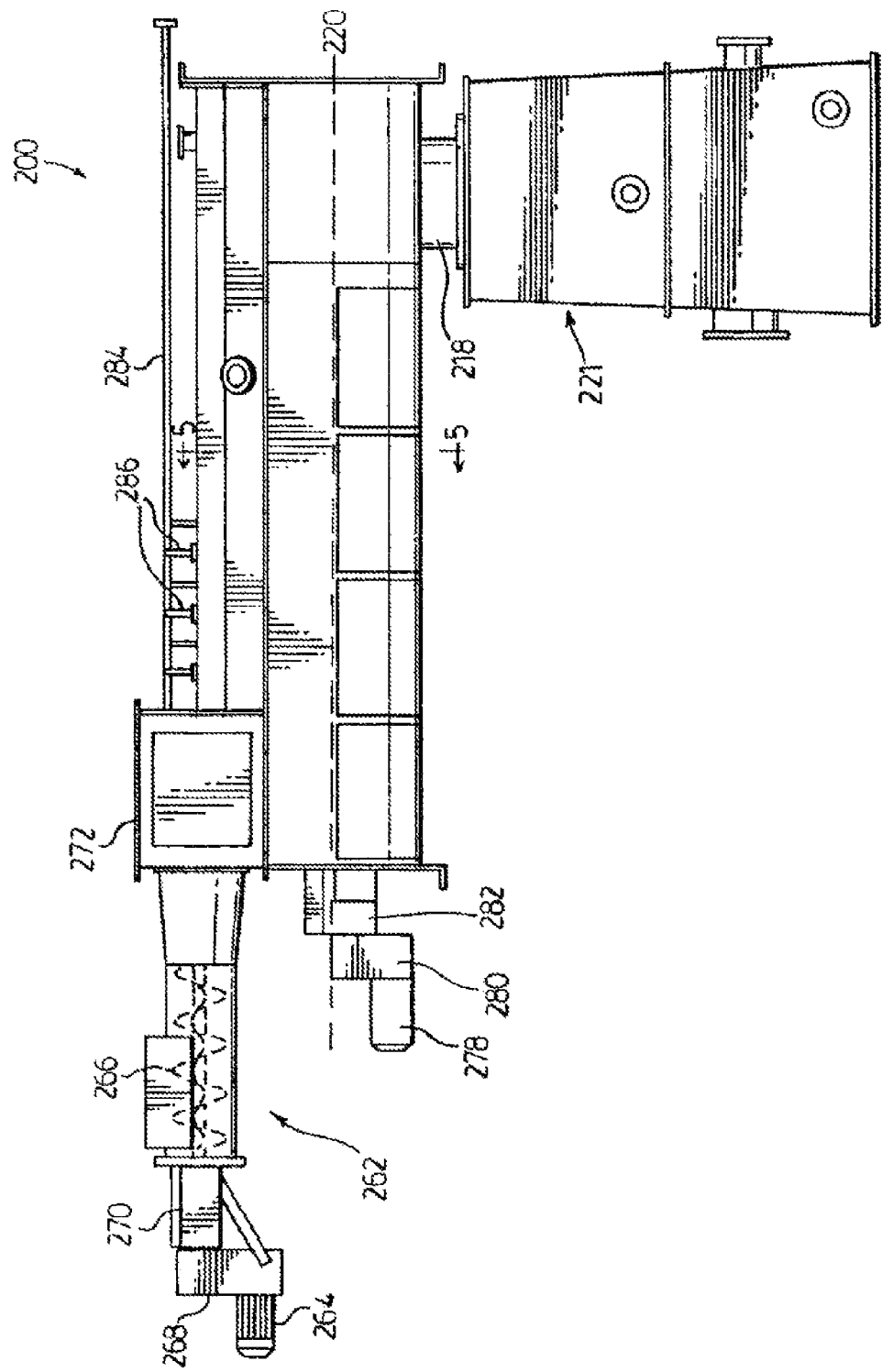
FIG. 20 is a front plan view of the apparatus of FIG. 19.
Figure 21:
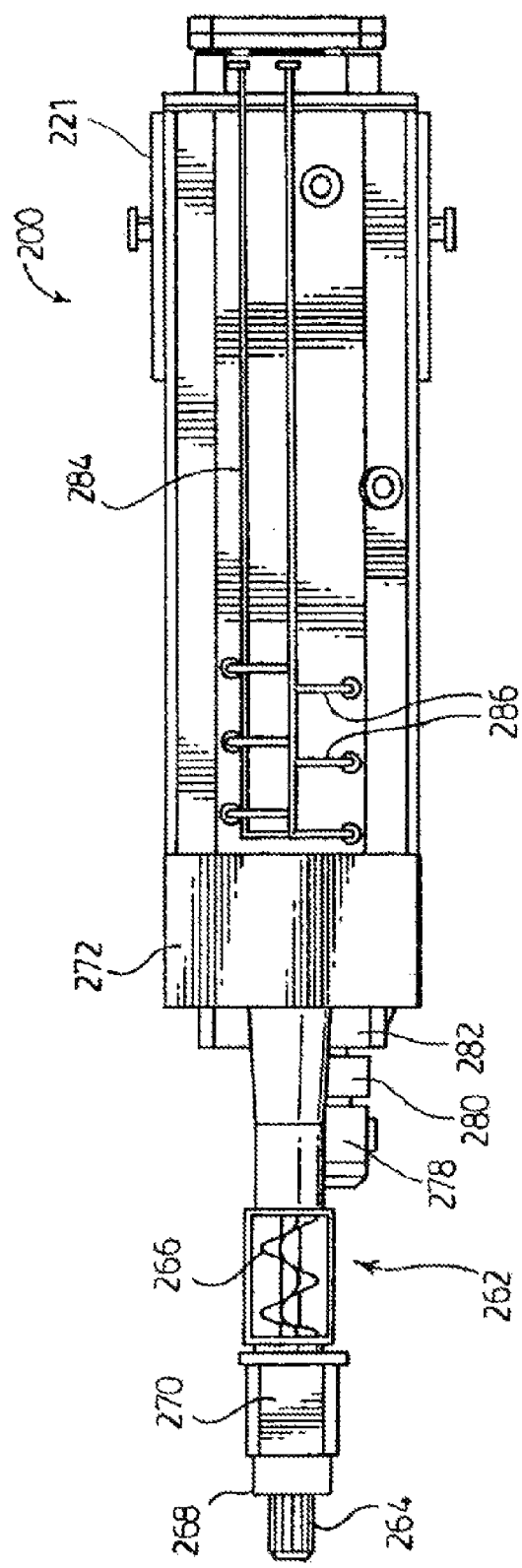
FIG. 21 is a top plan view of the apparatus of FIG. 19.

As exemplified in FIGS. 19-21, conveyance members 222 are rotatably mounted in chamber 204 and are drivenly connected to a motor 278. As exemplified, motor 278 is drivingly connected to conveyance members 222 via a transmission or gear reduction assembly provided in housing 280. The gear reduction assembly may be drivingly connected to ends 225, 227 of conveyance members 222 that are positioned inside housing 282.

Figure 23A:
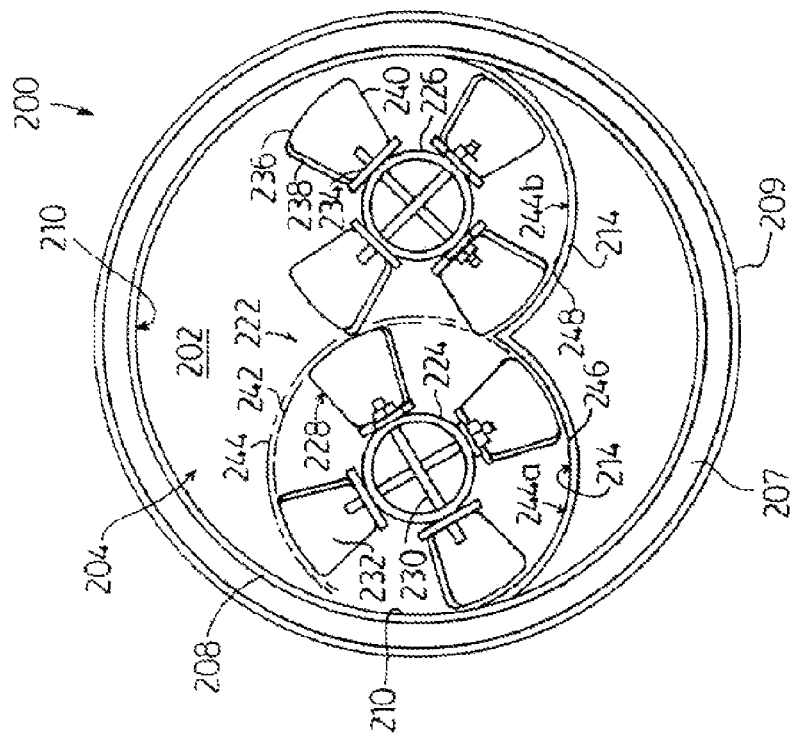
FIGS. 23A and 23B are transverse cross-sections taken along line 5-5 in FIG. 20, showing various rotational positions of an embodiment of a conveyance member of the present invention.
Figure 23B:
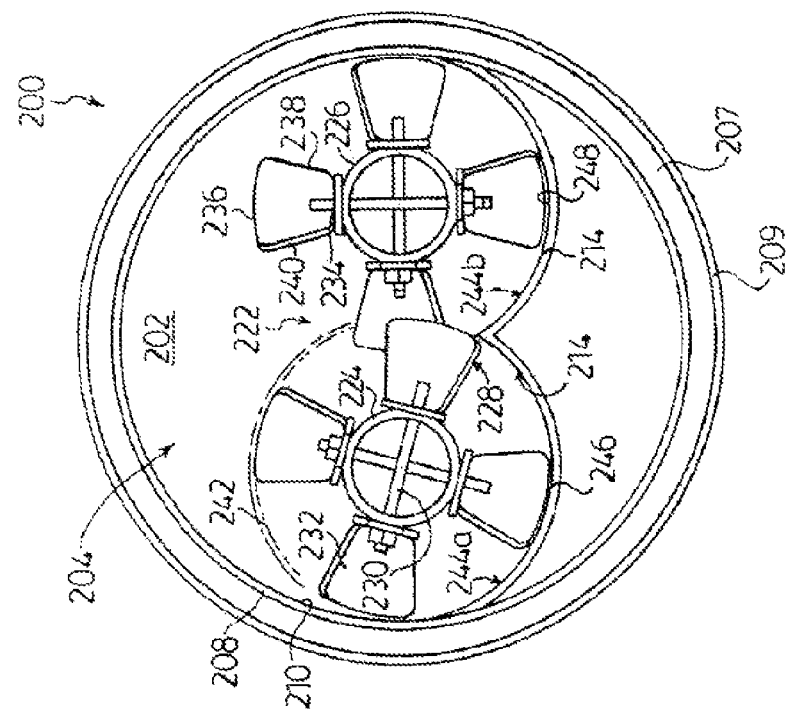
Figure 24:
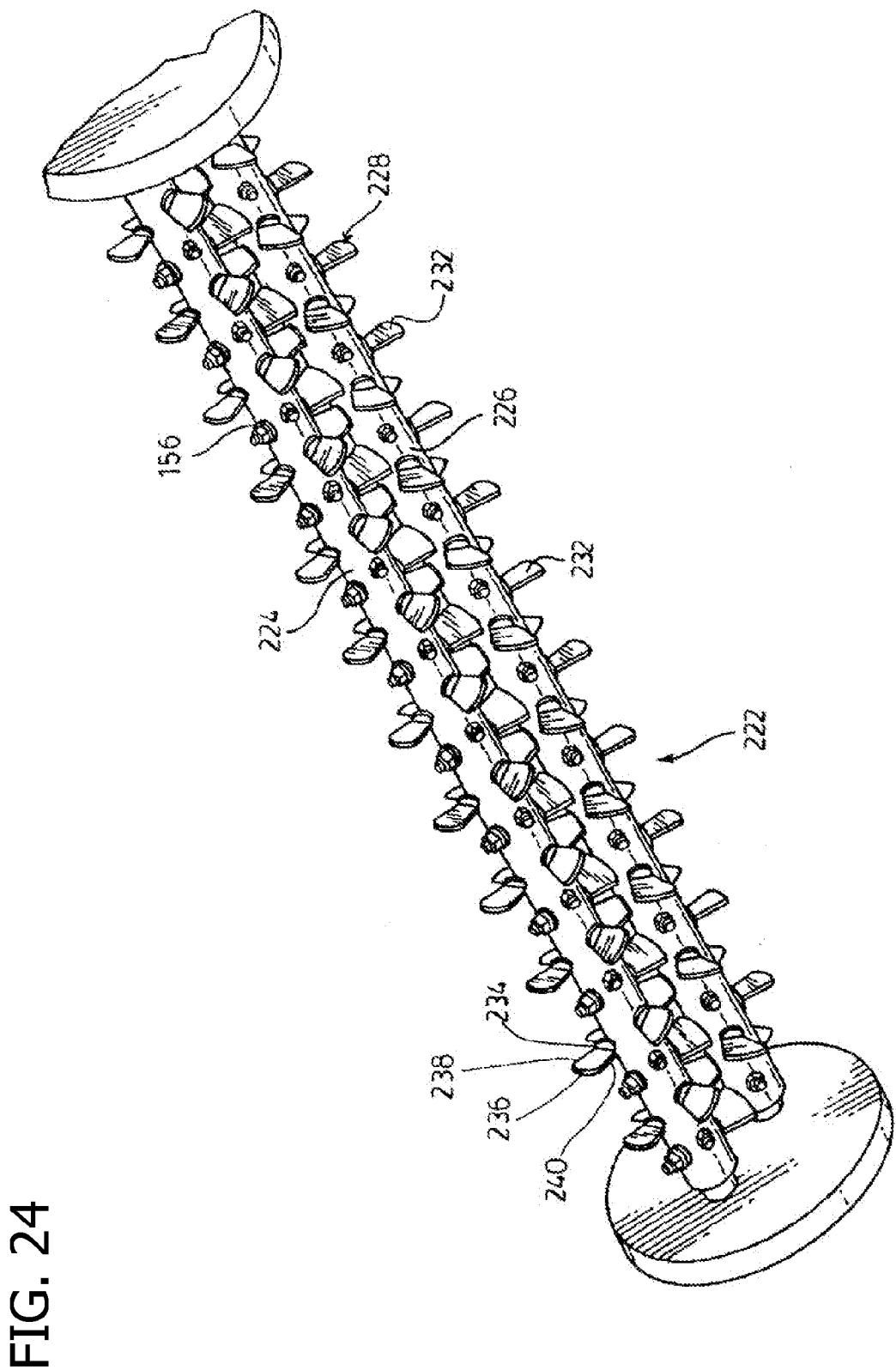
FIG. 24 is a perspective illustration of the conveyance member of FIG. 22.

In accordance with this particularly preferred aspect, chamber 204 extends longitudinally along axis 220 and has an upper portion that may be substantially cylindrical and a lower portion formed by wall section 214 that is preferably scallop shaped in transverse section (see FIGS. 23A and 23B). An advantage of having a scallop shaped lower section is that a rotary mounted conveyance member 222 may sweep adjacent all of, or at least much of, lower wall section 214 to reduce the likelihood of material having an increased residence time by not being conveyed along wall section 214. In alternate embodiments that are less preferred, chamber 204 may be otherwise shaped. For example, the upper portion may also be scallop shaped. Alternately, in combination with other aspect of this invention, the lower portion may be substantially cylindrical.

In accordance with this particularly preferred aspect conveyance member 222 is configured, in conjunction with the configuration of lower wall section 214, to urge the cellulosic feedstock through chamber 204 by sweeping lower wall section 214. That is, conveyance member 222 is preferably configured such that at least a portion thereof passes over lower inner surface in a continuous motion to push the cellulosic material forwardly. Furthermore, conveyance member 222 is preferably configured to sweep lower wall section 214 along generally the entire axial length of the chamber. It will be appreciated that, in less preferred embodiments, lower wall section 214 and conveyance member 222 need not be configured to sweep lower wall section 214 and may be of a variety of other configurations.

In the exemplified embodiments, in order to sweep lower wall section 214 and urge the cellulosic material through chamber 204, conveyance member 222 comprises first rotary shaft 224 and second rotary shaft 226, which extend longitudinally through chamber 204, and which are preferably spaced transversely apart and are preferably parallel. In alternate embodiments, conveyance member may comprise only one rotary shaft, or more than two rotary shafts.

Shafts 224, 226 may be provided with an auger, a plurality of paddles or the like. As exemplified, a plurality of paddles 228 extend radially outwardly from each rotary shaft. In addition, as exemplified in FIGS. 26A-26D, paddles 228 may each comprise a blade 232 and a stem 230, which couples the blade 232 to one of rotary shafts 226 and 228. Each blade 232 may be generally planar, and comprise a radially inner edge 234, a radially outer edge 236, and opposing first 238 and second 240 side edges, which extend between inner edge 234, and outer edge 236. In other embodiments, the paddles may be otherwise configured. For example, the blade may extend directly from the shaft, and a stem may not be provided. Alternatively, the stem may extend outwardly from the shaft, such that a space is provided between each blade and the shaft.

Blade 232 may be secured to one end of stem 230 by any means known in the art, such as welding, or mechanical affixation members such as rivets, or screws. The other end of stem 230 may be provided with a screw thread 276 on which bolt 274 may be received. Stem 230 may be secured to shaft 224, 226 such as by extending transversely through shaft 224, 226 from one side to the other and bolt 274 secured thereon. Suitable packing, gaskets or the like may be provided to limit or prevent moisture leaking out of shaft 224, 226 past stem 230. Stem 230 may be provided with one or more openings 258 in fluid communication with volume 256 inside shaft 224, 226. Accordingly, moisture may flow through shaft 224, 226, through stem 230 to paddle 228 and out through ports 252 into volume 204. However, paddles 228 may be directly secured to shafts 224, 226 or may be secured by any other means known in the art.

Preferably, as exemplified in FIG. 25A-25D, paddles 228 are arranged such that they generally define a longitudinally extending helix extending around each rotary shaft. In other words, a helix would be defined if the radially outer edge 236 of paddles were connected by a line extending from the inlet end of a rotary shaft to the outlet end thereof. Accordingly, helically adjacent paddles 228, for example paddles 228a and 228b, extend from the shaft at different angular positions around the shaft axis, as can be seen in FIG. 23.

Preferably, blades 232 of each paddle 228 are canted. That is, a first side edge 238 of each blade 232 is axially nearer the outlet 213 and rotationally trailing relative to a second side edge 240 (see FIGS. 23A and 23B).

Preferably, when viewed axially along the length of a rotary shaft, the first side edge of one paddle axially overlaps the second side edge of a next adjacent paddle.

In alternate embodiments, the paddles may be otherwise configured. For example, they may not be canted, and may be wedge shaped. Additionally, they may, for example, be arranged in a grid around shafts 226 and 224, rather than in a helix. It will be appreciated that in a particularly preferred embodiment, the paddles are arranged to define a helix, the blades are canted and the first side edge of one paddle axially overlaps the second side edge of a next adjacent paddle. However, these features may be used in any particular subcombination with any aspect of this invention.

Accordingly, in the embodiment shown, the step of conveying the cellulosic feedstock through the enclosed volume 202 comprises rotating each shaft 224, 226, such that the paddles 228 engage the cellulosic feedstock and urge the cellulosic feedstock axially through the chamber 204. Furthermore, in this embodiment, when the rotary shafts 224, 226 rotate, paddles 228 pass over inner lower wall section 214 in a continuous motion to push the cellulosic material forwardly. An advantage of the exemplified design is that the outer radial edges of the blades are configured to travel a generally consistent distance above lower wall section 214, thereby being able to effectively sweep lower wall section 214.

It will be appreciated that, in alternate embodiments, conveyance member 222 may be otherwise configured. For example, conveyance member 222 may comprise an auger which extends along enclosed volume 202, and which is rotated to urge the cellulosic feedstock through chamber 204 and sweep lower wall section 214.

In accordance with this particularly preferred aspect, paddles 228 and lower wall section 214 are configured such that when a given paddle is adjacent and passing over lower wall section 214, a substantially constant distance is maintained between the outer edge 236 of the paddle 228, and lower wall section 214. Such embodiments may aid in ensuring that the cellulosic material is urged forwardly at a substantially constant rate, and that the cellulosic material is not retained in the chamber.

For example, in the embodiments shown, the outer edge 236 of each paddle is curved or arcuate in shape (see for example FIG. 25B), and the curve preferably matches an arc 242 swept or defined by the outer edge 236 as the shafts rotate (see for example FIG. 23A). Accordingly, when shafts 224 and 226 rotate, the outer edge 236 of each paddle 228 will describe a circle. That is, outer edge 236 of each blade 232 is curved to define a sector of a circle having a radius R1. It will be appreciated that in embodiments wherein the blades 232 are canted, the arc 242 swept by outer edge 236 will be 3-dimensional (i.e. will have a depth). When shafts 224 and 226 rotate, the outer edge 236 of each blade 232 will describe a circle having a radius R2 define R2 on the drawings. In embodiments wherein blades 232 are not canted, R2 will equal R1. In embodiments wherein blades 232 are canted, R2 will be less than R1.

Further, in a preferred aspect, lower wall section 214 is configured such that in transverse section, as shown in FIGS. 23A-23B, lower wall section 214 defines at least one arc 244 and more preferably two or more arcs. In the embodiment shown, wherein conveyance member comprises two rotary shafts, lower wall section 214 defines two arcs 244a, 244b. That is, when viewed in transverse section, lower wall section 214 is scalloped. In alternate embodiments, wherein conveyance member comprises a different number of shafts, lower portion may define a different number of arcs, preferably one per shaft. Preferably, each shaft is centered above an arc 244.

Arcs 244a and 244b have a radius R3. Arc 244a comprises first portion 246 of lower wall section 214, and arc 244b comprises second portion 248 of lower wall section 214. First portion 246 is below first shaft 224, and second portion is below second shaft 226. Blades 232 and portions 246 and 248 are configured such that R3 is of a slightly greater radius than R2, for example less than about 6.5 mm greater than R2. Accordingly, when shafts 224 and 226 rotate, the paddles associated with shaft 224 will sweep along first portion 246, and the paddles associated with shaft 226 will sweep along second portion 248, such that a distance preferably less than about 6.5 mm is maintained between outer edge 236 of paddles 228 and first 246 and second 248 portions of lower wall section 214 as the paddles pass adjacent to lower wall section 214. The spacing between radial outer edge 236 and arc 244 may be from 2 to 15 mm. The spacing may vary depending upon the size of the particulate matter in the feedstock. The larger the size of the particulate matter, the larger the spacing may be. Preferably, the spacing is less than the maximum particle size and, more preferably, less than the median particle size. Accordingly, as the shafts rotate, particulate matter will be continually moved through the chamber. Further, if wall section 214 is heated, then the particulate matter will be inhibited from staying in the same location and being possibly overheated such that cellulose or hemicellulose is degraded by heat.

It will be appreciated that shafts 224, 226 may rotate in the same direction, or in opposite directions. Further, it will be appreciated that the rotation of shafts 224, 226 may be driven by a motor as exemplified, or another suitable means.

In accordance with a preferred embodiment, moisture is added to the cellulosic feedstock as the feedstock travels through the enclosed volume. Preferably, this step comprises adding moisture to increase the moisture content of the cellulosic feedstock from between about 5% and about 15 wt % to between about 30 to 60 wt %, preferably to between 45% and 55 wt %. The moisture may be added as liquid water, and/or may alternately be added as steam. If liquid water is used, it is preferably heated, for example, the liquid water may be heated to between about 50 to 70° C., preferably about 60° C. to about 70° C., and more preferably about 65° C. to about 70° C. It is preferred not to use steam since steam may result in the overheating of the cellulose and hemicellulose, causing degradation thereof. However, if the particularly preferred design exemplified herein is used, then higher temperatures may be used with reduced risk of degradation of the feedstock.

Additionally, the water may comprise additionally components. For example, one or more catalysts, including but not limited to mineral and organic acids, bases such as sodium hydroxide, organic solvents such as ethanol, and oxidizing agents such as hydrogen peroxide, may be added with the water.

The moisture may be added upstream from the chamber and/or in the chamber. The moisture may be added in a variety of ways, and is preferably added simultaneously at multiple spaced apart injection points. For example, referring to FIGS. 26A-26D, the injection points 250 may comprise a plurality of injection ports 252, which are provided in conveyance member 222 and/or in the inner wall 208 of the shell 206. In the embodiment of FIGS. 26A-26D, injection ports 252 are defined in blades 232 of paddles 228.

Alternately, or in addition, injection ports 252 may be provided in stems 230 and/or in shafts 224, 226. For example, in some embodiments, injection ports 252 are provided along the entire length L of chamber 204. In other embodiments, moisture injection ports 252 are preferably provided only in an upstream portion of chamber 204, preferably in the upstream half of the length L of chamber 204 and, more preferably in the first or upstream third $L_{1/3}$ of the length L of chamber 204 (see FIG. 22). For example, as exemplified in FIG. 19, a plurality of injection ports may be provided in the upper portion of chamber 204. As shown therein, one or more conduits 284 may convey water to a plurality of branch conduits 286 extending to different locations on the upper portion of chamber 204. The end of these conduits are in fluid flow communication with the interior of chamber 204, via a moisture addition member such as a nozzle or an open ended pipe or the like. As exemplified, six ports are provided. However additional or fewer ports may be used. Accordingly, moisture injection ports may additionally or alternately be provided in shell 206 of chamber 204. That is, injection points 250 may extend through wall 208, which defines inner surface of chamber 204 and/or wall section 214.

As shown, injection ports 252 of blades 232 are in fluid communication with one or more paddle ducts 254 provided within paddles 228. The one or more paddle ducts 254 are in fluid communication with a fluid conduit 256, which may extend through shafts 224, 226, for example via ports 258 provided in stem 230. Fluid conduits 256 are in fluid communication with a moisture source (not shown), for example at the ends 225, 227, of shafts 224, 226. Accordingly, as the conveyance member rotates, moisture is introduced into volume 202 by passing from a moisture source into fluid conduit 256, through ports 258 in stem 230, through paddle ducts 254, and out of ports 252.

In the above embodiments, the injection points may be positioned in a variety of configurations. In some embodiments, the injection points may be provided such that moisture is introduced into the cellulosic feedstock during its entire travel through chamber 204. For example, injection ports may be provided in shell 206 and/or in conveyance member 222 along the entire length of chamber 204. Preferably, the injection points may be provided such that moisture is introduced into the cellulosic feedstock during its initial travel through chamber 204. For example, the injection points may be provided only in a first portion, for example a first half and, more preferably, the first third, of the axial length of the impregnation chamber.

Furthermore, the number of injection points may vary depending on the particular embodiment. In some embodiments, wherein the injection points are provided in blades 232, each blade preferably comprises at least one injection port. In other embodiments, only some blades may comprise injection ports. Furthermore, in some embodiments, each blade comprises two injection ports; however in alternate embodiments, each blade may comprise one injection port, or greater than two injection ports. In some particular embodiments, chamber 204 is provided with a total of between 1 and 10 injection points.

In a preferred embodiment, the method optionally further comprises monitoring the moisture content of the feedstock as it passes through the volume. Accordingly, the amount of moisture introduced may be controlled in order to produce a feedstock having a predetermined moisture content. For example, one or more moisture sensors (not shown) may be positioned within chamber 204, for example upstream from inlet 211. As the feedstock passes through the chamber, the moisture sensors may measure the moisture content at various positions along the length of the chamber. When the moisture content of the feedstock reaches a predetermined value, for example between about 45% and about 55%, the addition of moisture to the chamber may be halted or reduced. In a further preferred embodiment, a controller (not shown) is operatively coupled to the moisture sensor(s) and controls the amount of moisture introduced based on the moisture content measured by the moisture sensor.

Alternately, and preferably in addition, the method also comprises heating the cellulosic feedstock as it travels through the volume. In some embodiments, the cellulosic feedstock is heated such that, when the feedstock exits the volume, the feedstock is at a temperature of between about 50 to about 65° C., preferably about 50° C. to about 70° C. when it exits outlet 213. Preferably, the cellulosic feedstock is provided to inlet 211 at less than about 30° C., and is heated to at least about 65° C. as it travels through the volume.

The cellulosic feedstock may be heated in a variety of ways. In some embodiments, the cellulosic feedstock may be heated directly. For example, as previously mentioned, in some embodiments, the moisture may be added as heated water. In such embodiments, in addition to providing moisture to the cellulosic feedstock, the heated water may serve to heat the cellulosic feedstock. Accordingly, in such embodiments, the method may comprise heating the moisture prior to contacting the moisture with the feedstock.

Figure 22:
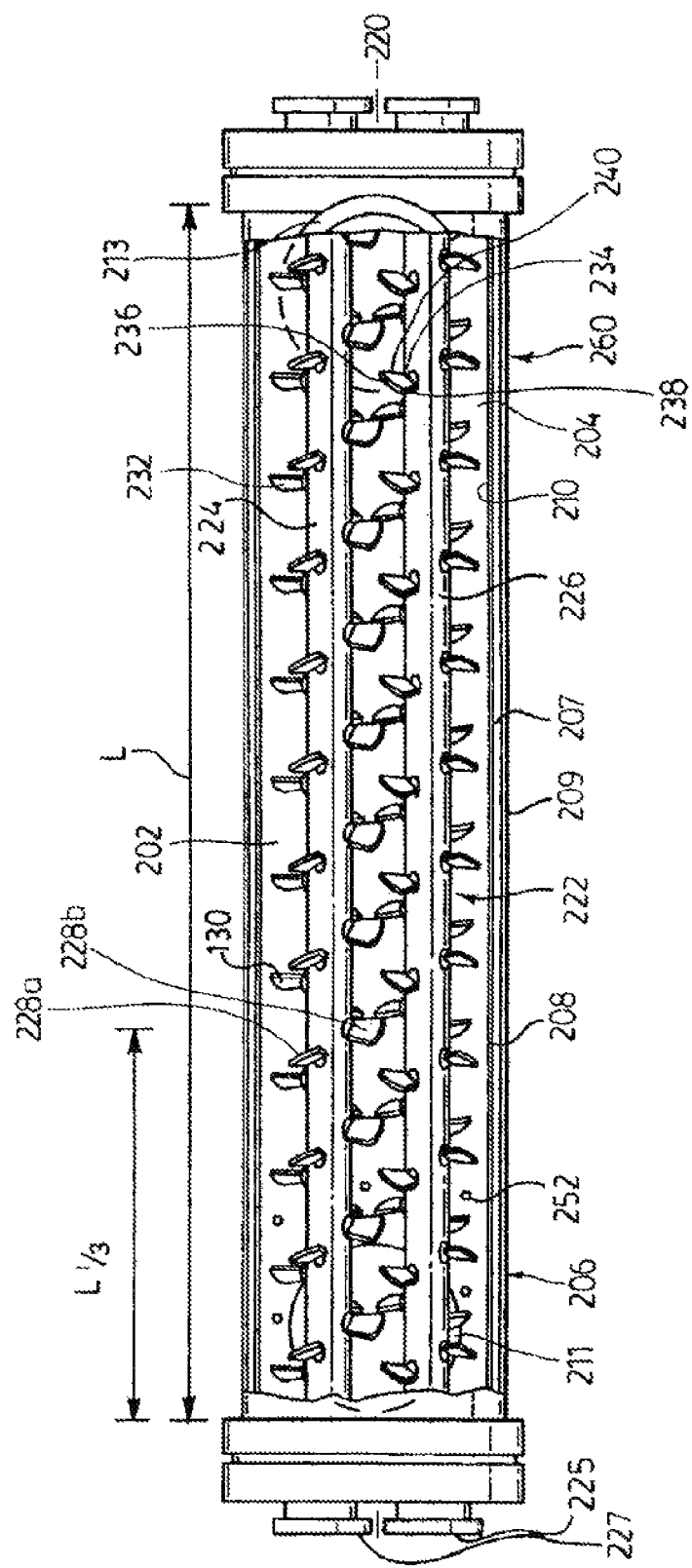
FIG. 22 is a cutaway top plan view of the mixing vessel of FIG. 19, wherein the upper portion of the shell has been removed showing a preferred embodiment of a conveyance member.

In other embodiments, the cellulosic feedstock may be heated indirectly. For example, the chamber walls 208 and/or the conveyance member may be heated. Referring to FIGS. 22 and 23, in the embodiments shown, the chamber walls 208 are heated by providing an outer wall 209, which surrounds at least a portion of shell 206. An enclosure 207 is defined between outer wall 209 and inner wall 208, and a heated fluid supply is associated with the enclosure. Enclosure 207 is in fluid communication at one end with one or more inlets, to which a heated fluid is supplied, and at the other end with one or more outlets, to which spent heated fluid is directed. Accordingly, the heated fluid circulates within enclosure 207, and provides heat to the cellulosic feedstock. The heated fluid may be water, for example, or steam. Any heating jacket or the like known in the art may be used.

The conveyance member preferably rotates at from 40 to 150 rpm and, more preferably, 45 to 75 rpm. Alternately, or in addition, the chamber may operate at a low fill factor, for example from 10 to 50 and preferably about 30%. Accordingly, a majority of the volume in chamber 204 may be filled with air. For example, if the fill factor is about 15-30%, then only 30% of the volume of chamber 204 is filled with feedstock, the rest being filled with, preferably air. As the conveyance member rotates, preferably at a relatively high speed, the feedstock will be thrown up into the empty upper portion of chamber 204 thereby mixing the feedstock to provide a more uniform distribution of heat and/or moisture throughout the feedstock. It will be appreciated that the use of a high rotational speed, combined with a low fill factor permits the use of a higher temperature in the heating jacket and/or in the temperature of the moisture provided to the feedstock in the chamber with reduced risk of heat degradation of the feedstock.

Accordingly, in one aspect, heat and/or moisture may be added in a chamber 204 and/or upstream thereof, wherein the conveyance member and the floor of the chamber are configured to permit the conveyance member to sweep the floor.

In another aspect, a chamber is utilized with a low fill volume and preferably a high rotational rate of the conveyance member to permit a higher heating temperature to be used with reduced risk of degradation of the cellulose and hemicellulose in the feedstock.

The cellulosic feedstock is preferably then subjected to activation and hydrolysis. The activation is preferably conducted by autohydrolysis. Autohydrolysis may be carried out directly after the treated feedstock exits the chamber or after a number of intermediate steps. For example, from outlet, the cellulosic feedstock may be directed to a holding tank 221 where it is stored for a period of time at an elevated temperature to further enhance the uniformity of the moisture and heat distribution, prior to being passed to an autohydrolysis reactor.

Accordingly, embodiments of the present invention provide a method and apparatus for heating and moistening a cellulosic feedstock, such that the cellulose of the feedstock is substantially accessible to hydrolysis enzymes. Furthermore, embodiments of the present invention provide a method and apparatus for heating and moistening a cellulosic feedstock while requiring substantially small amounts of heat and water. Accordingly, the process is substantially cost effective and energy efficient.

As detailed herein, various embodiments of the present invention are directed to methods and apparatus for use in preparing cellulosic feedstock for ethanol production. Further in accordance with the present invention various embodiments are directed to methods for preparing fermentable sugars. Generally in accordance with such embodiments, the method comprises providing a cellulosic feedstock, passing the cellulosic feedstock through an impregnation chamber (e.g., to provide a moisture-impregnated or acid-impregnated feedstock), passing the cellulosic through a holding tank, subjecting the feedstock to conditions of elevated temperature and pressure to promote break down of the cellulose-hemicellulose-lignin complex, and passing the cellulosic feedstock to an enzymatic hydrolysis reactor. Generally prior to introduction into the enzymatic hydrolysis reactor, the feedstock is released from the vessel (i.e., hydrolysis reactor) in which the feedstock is subjected to conditions of elevated temperature and pressure; the abrupt decrease in pressure as the feedstock is released from the vessel promotes break down of the cellulose-hemicellulose-lignin complex.

In accordance with various preferred embodiments for derivation of fermentable sugars, the residence time of the cellulosic feedstock in the holding tank is typically from about 1 to about 60 minutes, more typically from about 5 to about 45 minutes and, even more typically, from about 5 to about 30 minutes. Further in accordance with these and in accordance with various other embodiments, the cellulosic feedstock passes through the holding tank as detailed elsewhere herein (e.g., the embodiments depicted in FIGS. 5-10). For example, generally the feedstock migrates from the inlet towards the outlet of the holding tank under the force of gravity and the feedstock is conveyed laterally across the outlet of the holding tank. Typically, while the cellulosic feedstock is conveyed laterally across the outlet of the holding tank, cellulosic feedstock is actively withdrawn from essentially an entirety of the outlet. More particularly, typically a generally equal amount of cellulosic feedstock is withdrawn from each portion of the outlet as the cellulosic feedstock is conveyed laterally across the outlet. A first portion of the cellulosic feedstock may be withdrawn in a first lateral direction and second portion of the cellulosic feedstock may be laterally withdrawn in a second lateral direction.

Alternatively, methods for deriving fermentable sugars including passing cellulosic feedstock through a holding tank and toward a hydrolysis reactor may also comprise passing cellulosic feedstock through a holding tank having a live bottom and including a discharge member in communication with a collection and conveyance member as detailed above.

VII.

Referring to FIGS. 27 to 34, an embodiment of an apparatus 100 of the present invention is shown. Apparatus 100 comprises a weight sensor 102, a moisture sensor 104, a processor 106, and mixing vessel 108. Apparatus 100 is usable to determine if an amount of moisture needs to be added to a cellulosic feedstock to obtain a predetermined moisture content in the cellulosic feedstock, and preferably to add the amount of moisture to the cellulosic feedstock if such is required.

In order to produce a feedstock having a predetermined moisture content, the starting moisture content of the feedstock must be known and the amount of water addition that is required must be determined. In accordance with one aspect of this invention, the starting moisture content is determined by utilizing a moisture sensor to determine the starting moisture content. The amount of water addition that is required may be determined using the starting moisture content and the amount of feedstock having that moisture content that is provided to the process. The measurements may be made on a continuous basis or by sporadic sampling.

Figure 27:
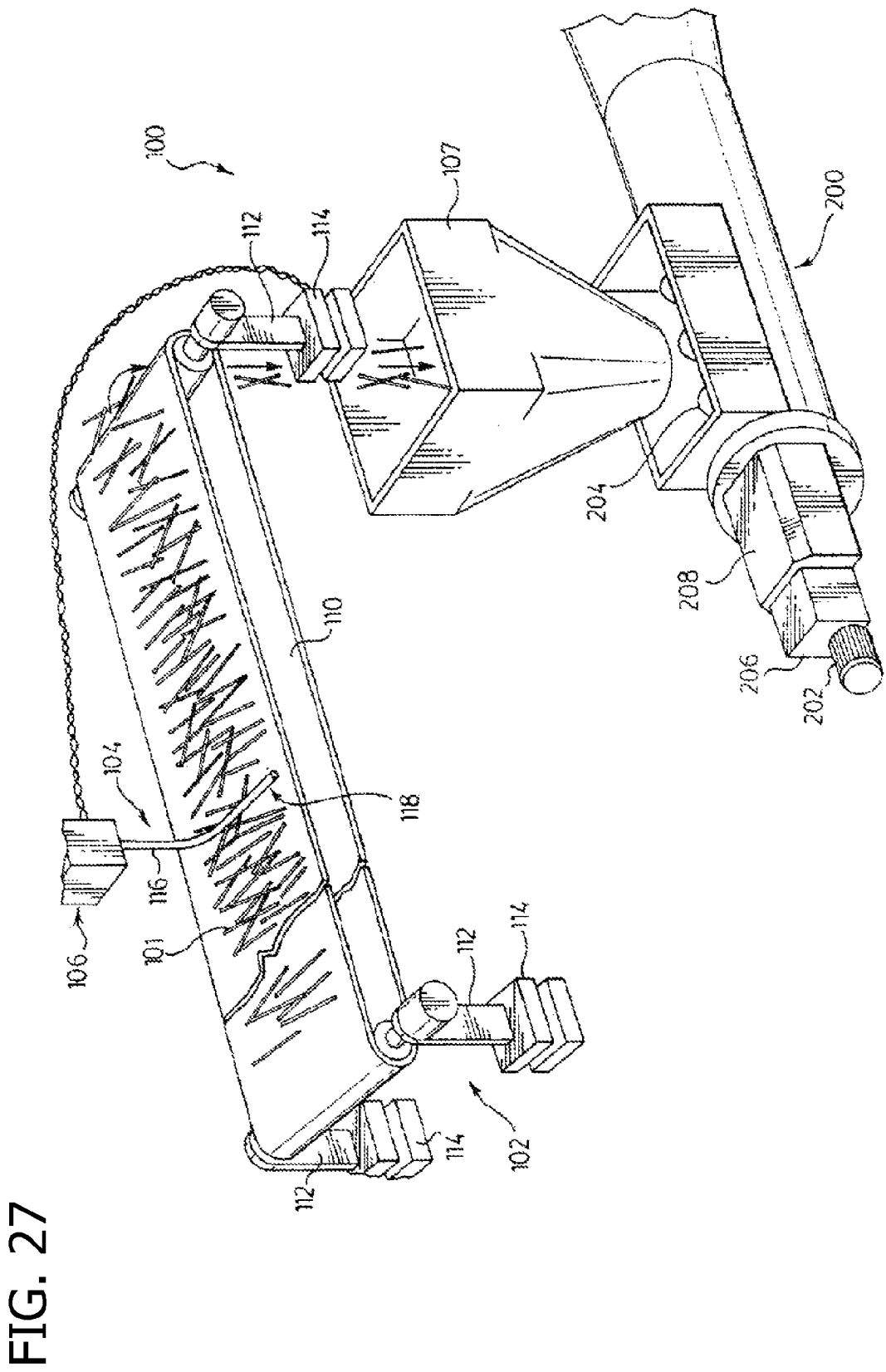
FIG. 27 is a partial perspective illustration of an embodiment of an apparatus of the present invention.
Figure 28:
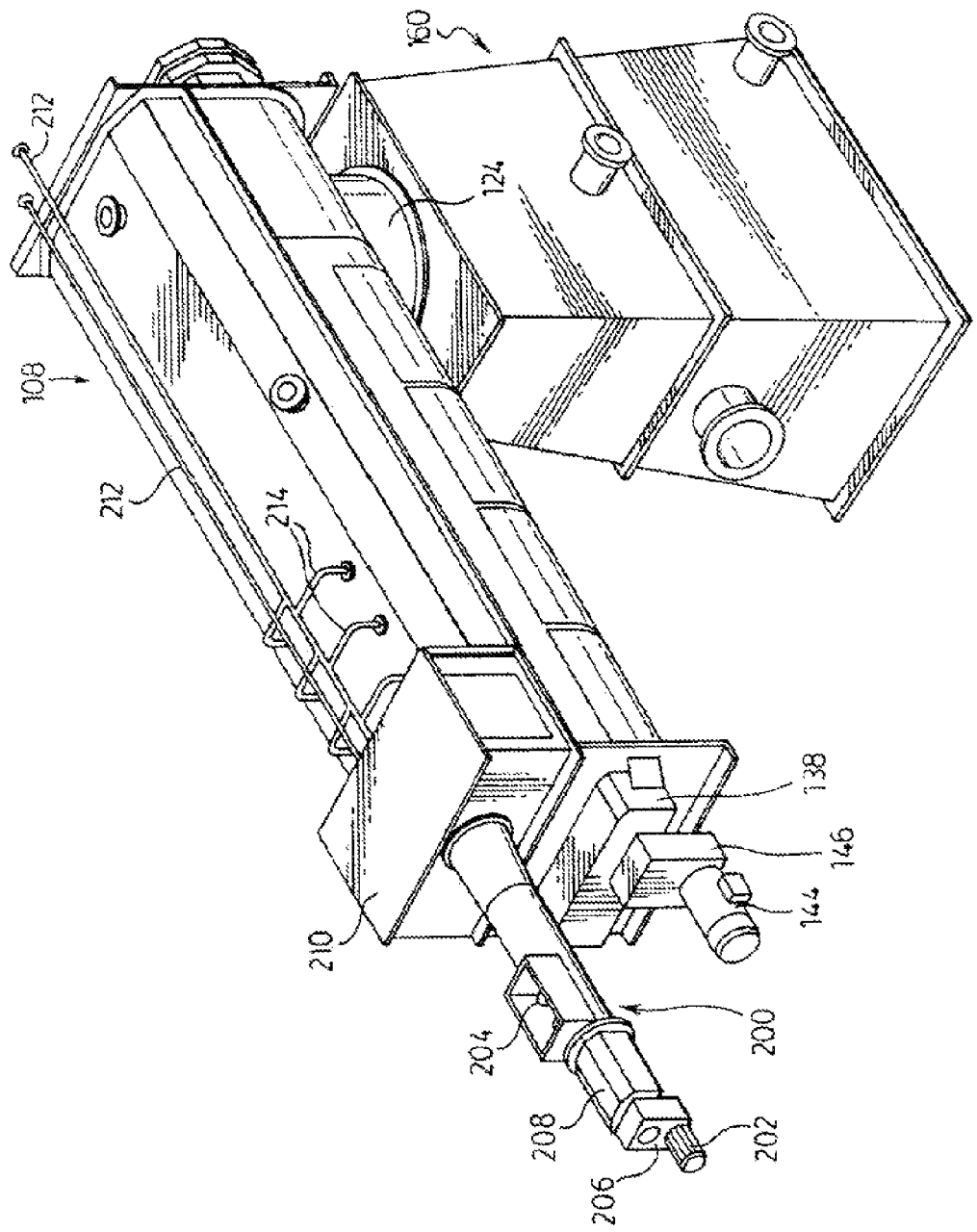
FIG. 28 is a perspective illustration of an embodiment of a mixing vessel of an apparatus of the present invention.
Figure 29:
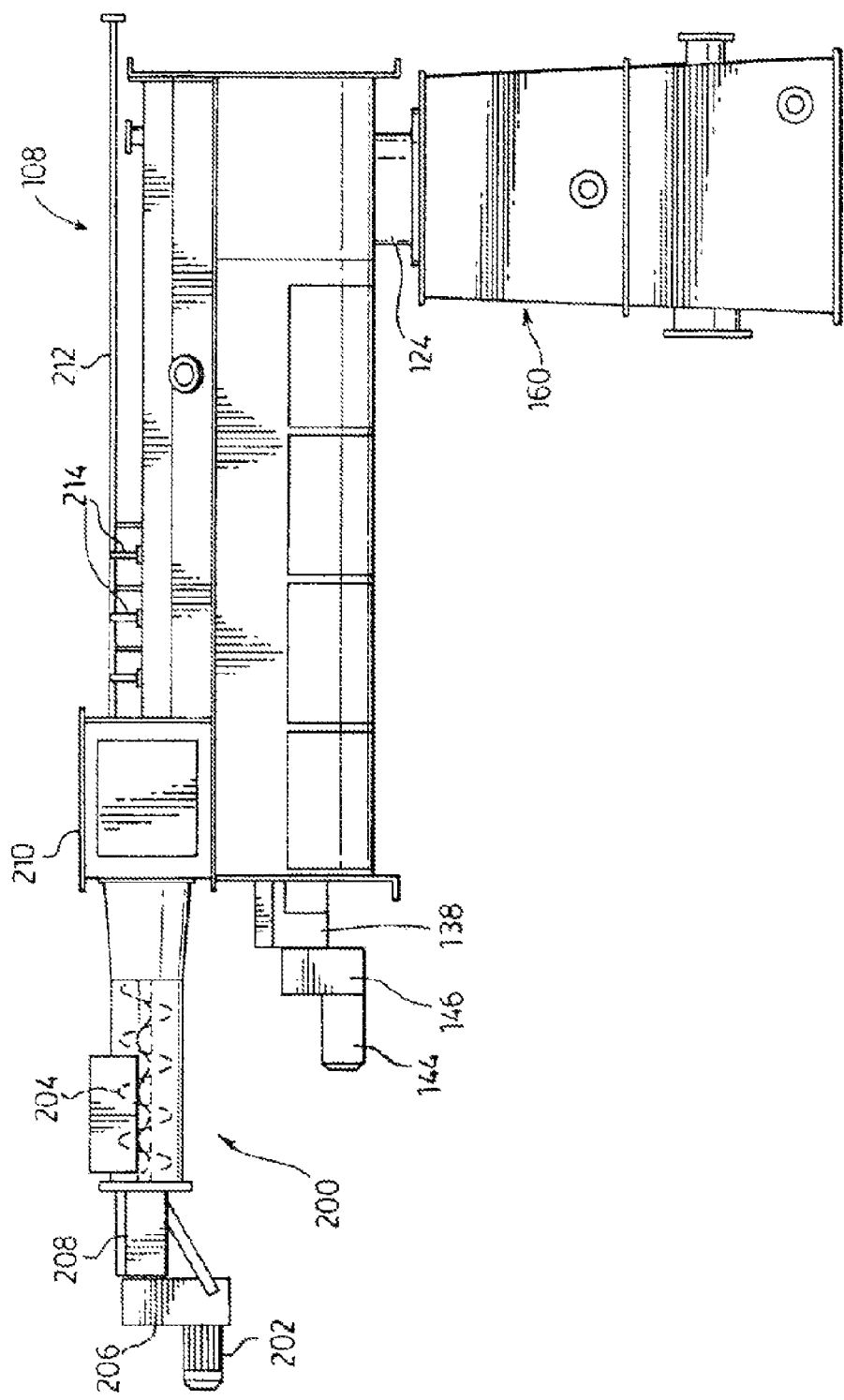
FIG. 29 is a side plan view of the mixing vessel of FIG. 28.
Figure 30:
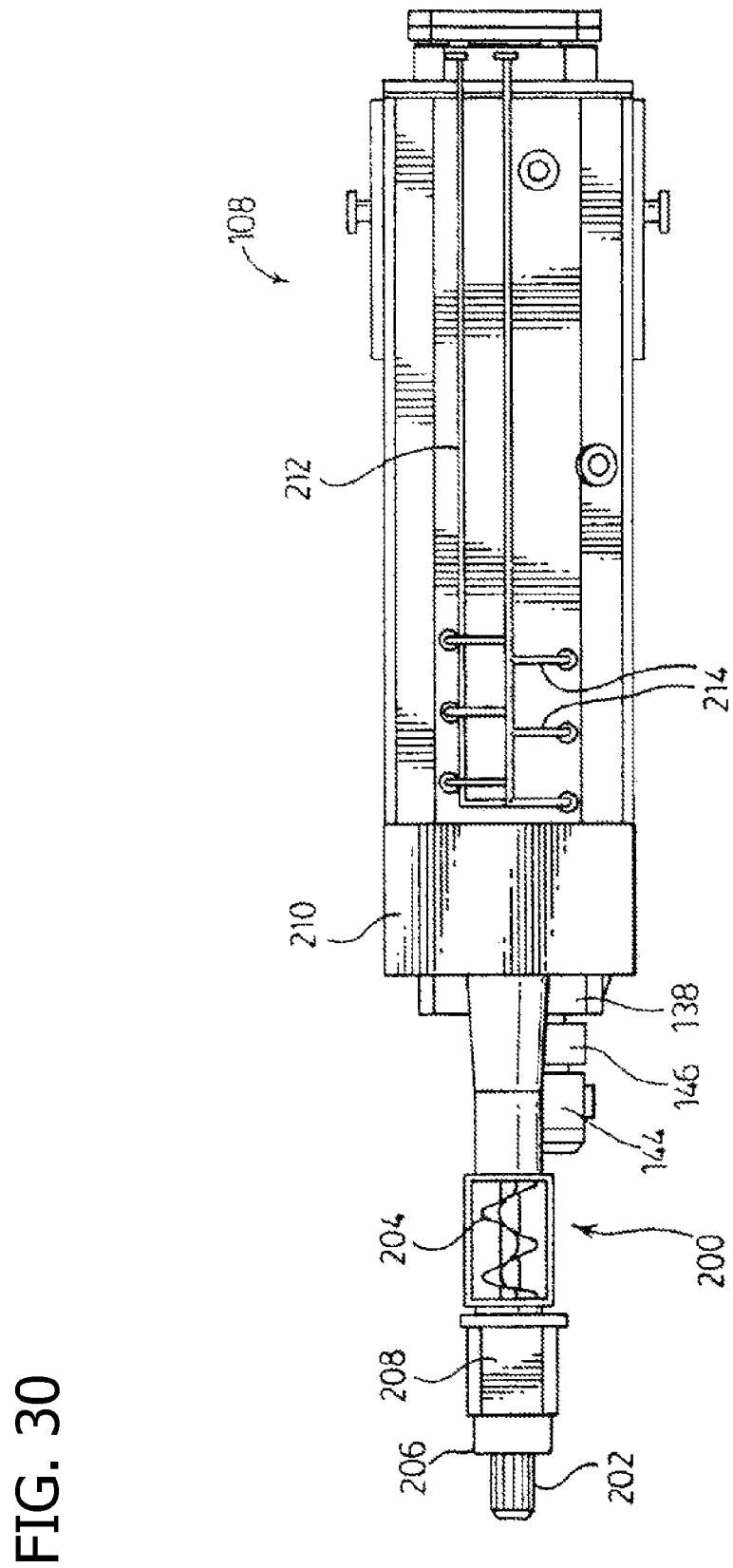
FIG. 30 is a top plan view of the mixing vessel of FIG. 28.

As exemplified in FIG. 27, weight sensor 102 is configured to weigh the cellulosic feedstock 101 that is provided to apparatus 100, and to provide an output value corresponding to a weight of the cellulosic feedstock 101 on the weight sensor 102. In some embodiments, weight sensor 102 is further configured to continuously convey and weigh the cellulosic feedstock 101. For example, in the embodiment shown, weight sensor 102 is a weighing conveyor, which comprises a conveyor belt 110, which rests on supports 112. Supports 112 each comprise a scale 114, for weighing the cellulosic material 101 resting on the conveyor belt at a given moment in time. In this embodiment, cellulosic feedstock 101 is continuously deposited on the conveyor belt, and is conveyed towards mixing vessel 108 as scales 114 continuously weigh the cellulosic feedstock 101.

In embodiments wherein weight sensor 102 is operated in a continuous fashion, the output value provided by weight sensor 102 may correspond to the weight measured at a given moment in time. For example, in some embodiments, weight sensor 102 may measure the weight of the cellulosic feedstock 101 on conveyor belt 110 every 0.5 seconds. By computation processor 106 determines the exact weight of water to be added to reach the desired moisture set point. The output value is sent to processor 106, as will be further described hereinbelow, and may additionally or alternately be displayed, for example on a screen (not shown).

In operation of this preferred embodiment, the measurement of the moisture is taken on a continuous basis as the fiber is conveyed by the weighing conveyor. Simultaneously the weighing conveyor measures the total weight of the fiber on the weighing conveyor, namely the weight of the fiber as well as the water in the fiber structure. This information, as well as information as to the amount of fiber leaving and/or being added to conveyor belt 110 per unit time is provided to processor 106. For example, processor 106 may be programmed with the speed of conveyor belt 110. Accordingly processor 106 can determine the weight of fiber entering hopper 107 per unit time as well as the moisture content of that fiber. Preferably, processor 106 is also provided with information as to the amount of time required for the fiber leaving conveyor belt 110 to enter a zone (e.g., mixing vessel 108) at which moisture is added to the fiber. Processor 106 may accordingly provide a signal adjusting the amount of moisture added to the fiber passing through the moisture addition zone.

Preferably, processor 106 may provide a time delay signal adjusting the amount of moisture added to a particular segment of fiber passing through the moisture addition zone. These signals may be continuously processed such that the amount of moisture added to each segment of fiber is premised upon the actual moisture content of that segment of fiber. Accordingly the required moisture addition in the subsequent impregnation step may be controlled to obtain the desired final total moisture content prior to autohydrolysis.

In alternate embodiments, weight sensor 102 may be another type of weight sensor, for example a stationary balance, which the cellulosic feedstock is deposited onto and removed from in a batch-type process. For example, a hopper or other storage vessel may be provided with a known weight of feedstock, which is then provided to conveyor belt 110. Alternately, the hopper or storage vessel may be weighed and the feedstock may then be provided to conveyor belt 110. It will be appreciated that the feedstock may be weighed after the moisture content is determined (e.g., hopper 107 may be weighed). In embodiments wherein weight sensor 102 is operated in a batch-type fashion, the output value may correspond to the weight of a given batch.

As exemplified in FIG. 27, moisture sensor 104 is configured to measure the moisture content of the cellulosic feedstock provided to apparatus 100 (referred to hereinafter as the initial or starting moisture content). The initial moisture content will depend on numerous factors, such as the nature of the cellulosic feedstock and any storage conditions and upstream processes to which it has been subjected. However, in some embodiments, the initial moisture content is less than about 15 wt %.

In the embodiment shown, moisture sensor 104 is an electronic moisture sensor, such as Doscher & Doscher moisture scan or Acrowood moisture analyzer, which is provided in the distal region 118 of a probe 116. Distal region 118 is positioned adjacent conveyor belt 110, and measures the moisture content of the cellulosic feedstock as it is preferably weighed by weight sensor 102. In alternate embodiments, moisture sensor may be otherwise configured. For example, moisture sensor 104 may be a microwave moisture sensor, and therefore may not directly contact the cellulosic feedstock 101 or conveyor belt 110.

Processor 106 is coupled to moisture sensor 104 and weight sensor 102. Although cables are shown to connect moisture sensor 104 and weight sensor 102 to processor 106, it is contemplated that wireless connections may be provided. Processor 106 is configured to determine an amount of moisture to be added to the cellulosic feedstock based on the weight of the cellulosic feedstock, and the initial moisture content of the cellulosic feedstock to obtain a cellulosic feedstock having a predetermined moisture content. That is, processor is coupled to receive the output of the weight sensor 102 and the moisture sensor 104, and based on these outputs, determine the amount of moisture to be added to the cellulosic feedstock in a downstream pre-treatment process. For example, in some embodiments, the predetermined moisture content of the cellulosic feedstock may be between about 30 wt % and 60 wt %. If the weight of the cellulosic feedstock is about 10 kg, and the moisture content is about 10%, then the amount of moisture to be added to the cellulosic feedstock may be between about 3 kg and 12 kg.

The amount of moisture added is preferably determined and more preferably controlled by processor 106, in order to obtain cellulosic feedstock of a predetermined moisture content. That is, processor 106 may determine the amount of moisture to be added to the cellulosic feedstock, and may display this amount, such that it may be added manually, or the processor may be connected to the mixing vessel, such that the amount may be added automatically. In an optional embodiment, the values obtained from moisture sensor 104 and weight sensor 102 may be provided to an operator who may then determine the amount of water to be added, based on a table, chart, or by using a calculation.

The moisture is preferably added as liquid water, but may be added as steam. Preferably, water is provided as discrete droplets of water, preferably between 600 μm and 6000 μm in diameter, and preferably from multiple locations.

In some embodiments, additional components, such as one or more hydrolysis catalysts, such as organic and/or inorganic acids, caustic soda, and the like, may be added together with the moisture.

Referring to FIGS. 28 to 34, mixing vessel 108 is preferably provided downstream from weight sensor 102. Moisture may be added to the cellulosic feedstock in mixing vessel 108 and/or upstream from mixing vessel 108 (i.e. between weight sensor 102 and mixing vessel 108) as will be described further herein.

Preferably, at least some of the moisture is added in mixing vessel 108. Accordingly, mixing vessel 108 may be above atmospheric pressure. Moisture (as water or steam) may accordingly flow upstream to exit mixing vessel 108 unless the inlet to mixing vessel 108 inhibits such flow. In the embodiment shown, impregnator feeder 200 is preferably positioned upstream of mixing or impregnation vessel 108 and may be any feeder that inhibits, and preferably prevents, the flow of moisture upstream. A rotating valve or the like may be provided to segment such upstream flow. Preferably impregnation feeder is a screw feeder comprising a motor 202 drivingly connected to a screw or auger 204, such as via a transmission or gear reduction assembly provided in housing 206. The shaft on which screw 202 is provided may be rotatably mounted in housing 208 such that augur 204 is a cantilevered plug screw conveyor. Accordingly, feeder 200 produces a plug of material that prevents upstream migration of moisture. The plug may be conveyed into inlet housing 210 that is mounted, e.g., to the upper surface of mixing vessel 108. The feedstock may then pass downwardly into mixing vessel 108. In other embodiments, impregnator feeder 200 may not be used.

In the embodiment shown, mixing vessel 108 comprises a longitudinally extending volume 120 having an inlet at one end (e.g., positioned within or below inlet housing 210), and an opposed outlet, which may be an opening in the bottom of mixing vessel above outlet passage 124. A conveyance member 126 is preferably positioned inside volume 120. In the embodiment shown, conveyance member 126 preferably comprises two rotary shafts 128, having a plurality of paddles 130 extending outwardly therefrom. In use, rotary shafts 128 of conveyance member 126 are rotated, such that paddles 130 engage the cellulosic material within volume 120 and urge the cellulosic material from the inlet towards outlet 124 while mixing the cellulosic material. In other embodiments, conveyance member 126 may be otherwise configured. For example, conveyance member 126 may comprise one or more longitudinally extending augers, single screw conveyor with paddles, ribbon screw conveyor, standard screw conveyor with tabbed flights and bars, and the like. In addition, vessel 108 need not extend horizontally but may be angled downwardly so that gravity assists the travel of the feedstock through vessel 108. As exemplified in FIG. 28, conveyance members 126 may be drivenly connected to a motor 144. As exemplified, motor 144 is drivingly connected to conveyance members 126 via a transmission or gear reduction assembly provided in housing 146. The gear reduction assembly may be drivingly connected to ends 137 of conveyance members 126 that are positioned inside housing 138.

A hopper 107 is preferably provided between weight sensor 102 and feeder 200, in order to funnel the cellulosic material from weight sensor 102 into mixing vessel 108. Any other passage or feeder known in the art may be used. Accordingly, hopper may feed cantilevered plug screw conveyor 200 immediately prior to impregnator vessel 108.

In some embodiments, some or all of the moisture may be added to the cellulosic feedstock while the cellulosic feedstock is conveyed through feeder 200. For example, some of the moisture may be added to lubricate the flow of the feedstock through feeder 200.

Alternately, or in addition, some or all of the moisture may be added to the cellulosic feedstock while the cellulosic feedstock is conveyed through mixing vessel 108. In such embodiments, mixing vessel 108 may comprise multiple moisture injection ports 132. For example, as exemplified in FIG. 28, a plurality of injection ports may be provided in the upper portion of mixing vessel 108. As shown therein, one or more conduits 212 may convey water to a plurality of branch conduits 214 extending to different locations on the upper portion of mixing vessel 108. The end of these conduits are in fluid flow communication with the interior of mixing vessel 108, via a moisture addition member such as a nozzle or an open ended pipe or the like. As exemplified, six ports are provided. However, additional or fewer ports may be used. Accordingly, moisture injection ports may be provided in the inner surface 150 of shell 152 of vessel 108.

Alternately, or in addition, referring to FIGS. 33A-33D, in the embodiment shown, paddles 130 of conveyance member 126 comprise one or more injection ports 132. A fluid conduit, which may be interior volume 134 of each rotary shaft 128, provides fluid communication between moisture injection ports 132 and a fluid source (not shown), which may be coupled to ends 137 of rotary shafts 128 that are mounted in housing 138. The fluid conduit may be external to shaft 128 or a separate passage inside shaft 128. Alternately, or in addition, moisture injection ports 132 may be provided in the outer surface of rotary shafts 128 (see FIG. 31).

Preferably, shaft 128 and paddles 130 are not provided with injection ports 132. However, a heated fluid is preferably conveyed through shaft 128 and/or paddles 130 so as to provide indirect heat to the feedstock in mixing vessel 108.

As exemplified, paddles 130 are secured to shafts 128 by rods 154. Paddles 130 may be secured to one end of rods 154 by any means known in the art, such as welding, or mechanical affixation members such as rivets, or screws. The other end of rod 154 may be provided by a screw thread on which bolt 156 may be received. Rods 154 may be secured to shaft 128 such as by extending transversely through shaft 128 from one side to the other and bolt 156 secured thereon. Suitable packing, gaskets or the like may be provided to limit or prevent moisture leaking out of shaft 128 past rod 154. Rod 154 may be provided with one or more openings 158 in fluid communication with volume 134 inside shaft 128. Accordingly, moisture may flow through shaft 128, through rod 154 to paddle 130 and out through ports 132 into volume 120 of vessel 108. However, paddles 130 may be directly secured to shafts 128 or may be secured by any other means known in the art.

In some embodiments, injection ports 132 are provided along the entire length L of mixing vessel 108. In other embodiments, moisture injection ports 132 are provided only in an upstream portion of mixing vessel 108, preferably in the upstream half of the length L of mixing vessel 108 and, more preferably in the first or upstream third $L_{1/3}$ of the length L of mixing vessel 108 (see FIG. 31).

In some embodiments moisture may additionally or alternately be added to the cellulosic feedstock upstream from mixing vessel 108. For example, referring to FIG. 27, a passage, which may comprise or consist of hopper 107, may be provided between conveyor belt 110 of weight sensor 102 and the inlet of the mixing vessel 108. In the embodiment shown, all of the passage extends downwardly. However, in alternate embodiments, only a portion of the passage may extend downwardly. The passage may comprise at least one, and preferably multiple, moisture injection ports. The moisture injection ports may be configured to inject a mist of moisture into the passage. For example, the interior wall of hopper 107 may be provided with moisture injection ports. Alternately, or in addition, a water outlet, such as one or more spray atomizers, may be provided inside hopper 107, preferably at an upper section thereof.

Figure 31:
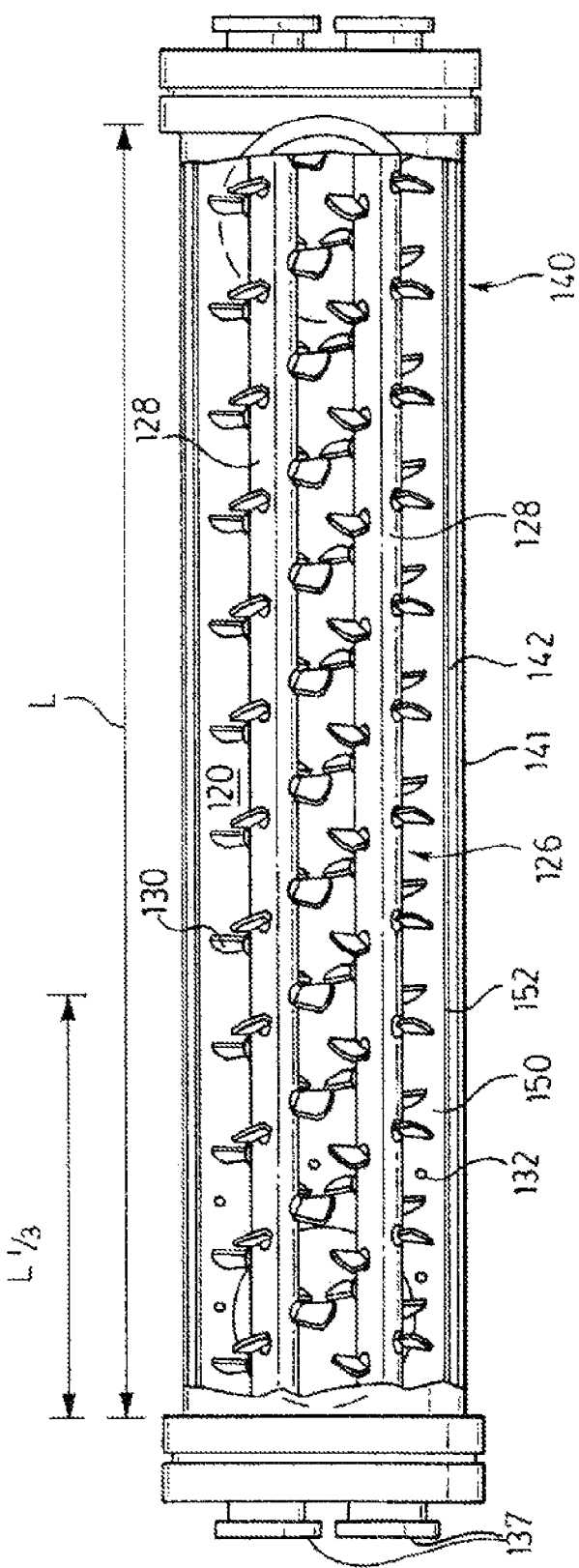
FIG. 31 is a cutaway top plan view of the mixing vessel of FIG. 28, wherein the upper portion of the shell has been removed showing a preferred embodiment of a conveyance member.
Figure 32:
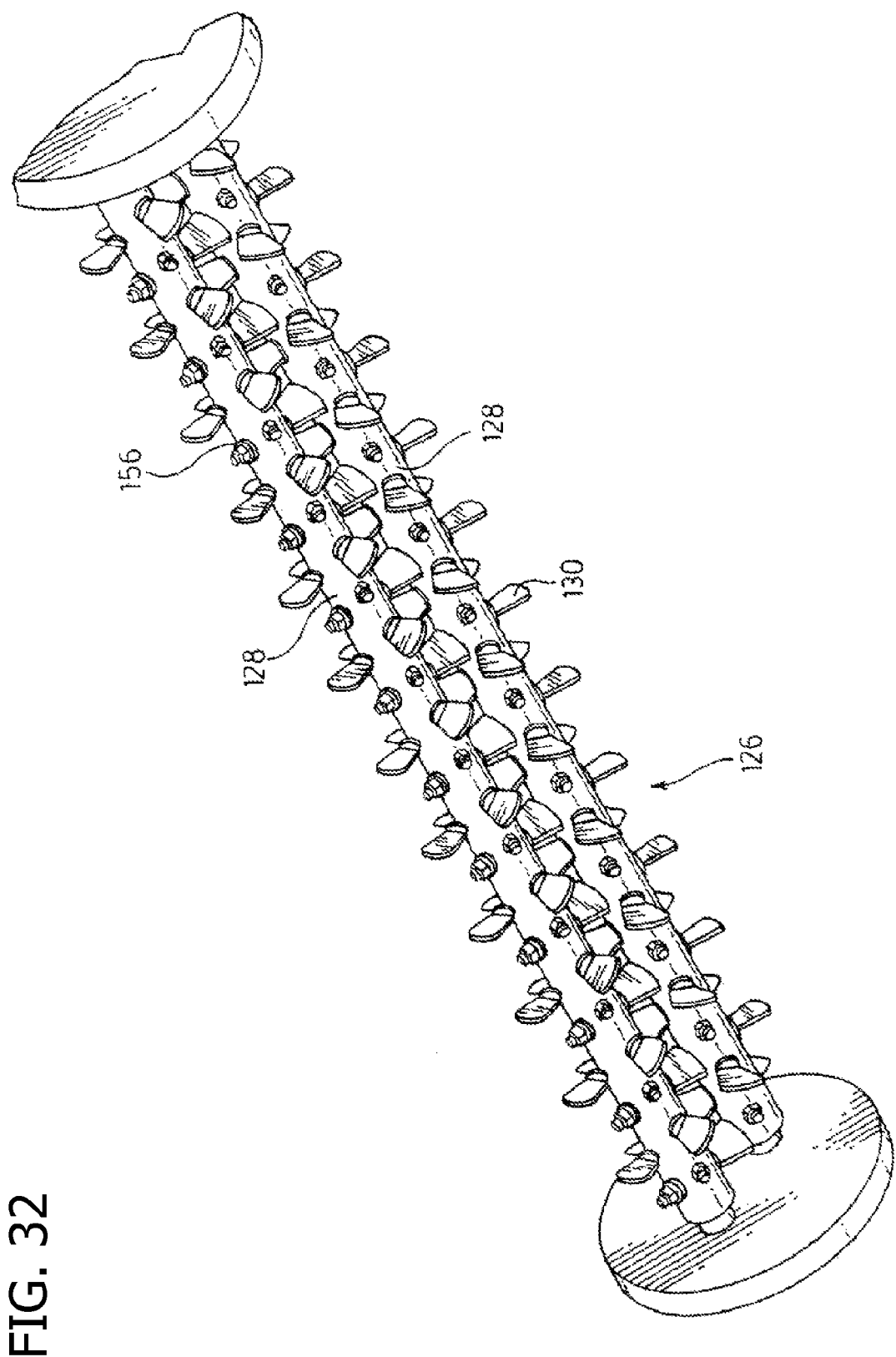
FIG. 32 is a perspective illustration of the conveyance member shown in FIG. 31.

In some embodiments, as exemplified in FIG. 31, mixing vessel 108 may be provided with a heating jacket 140. Heating jacket 140 may be of any construction known in the art. For example, as exemplified, heating jacket 140 comprises an outer shell 141 defining an inner volume 142 extending between outer shell 141 and inner shell 152, through which a heated fluid, for example steam or heated water, is passed from a fluid source (not shown) in fluid communication with heated fluid inlet, through volume 142 to a cooled fluid outlet. In some embodiments, heating jacket 140 is configured to heat the cellulosic feedstock from less than about 50° C. (e.g. about 20° C.) at the inlet to between about 50° C. and about 70° C. at outlet 124.

Figure 34:
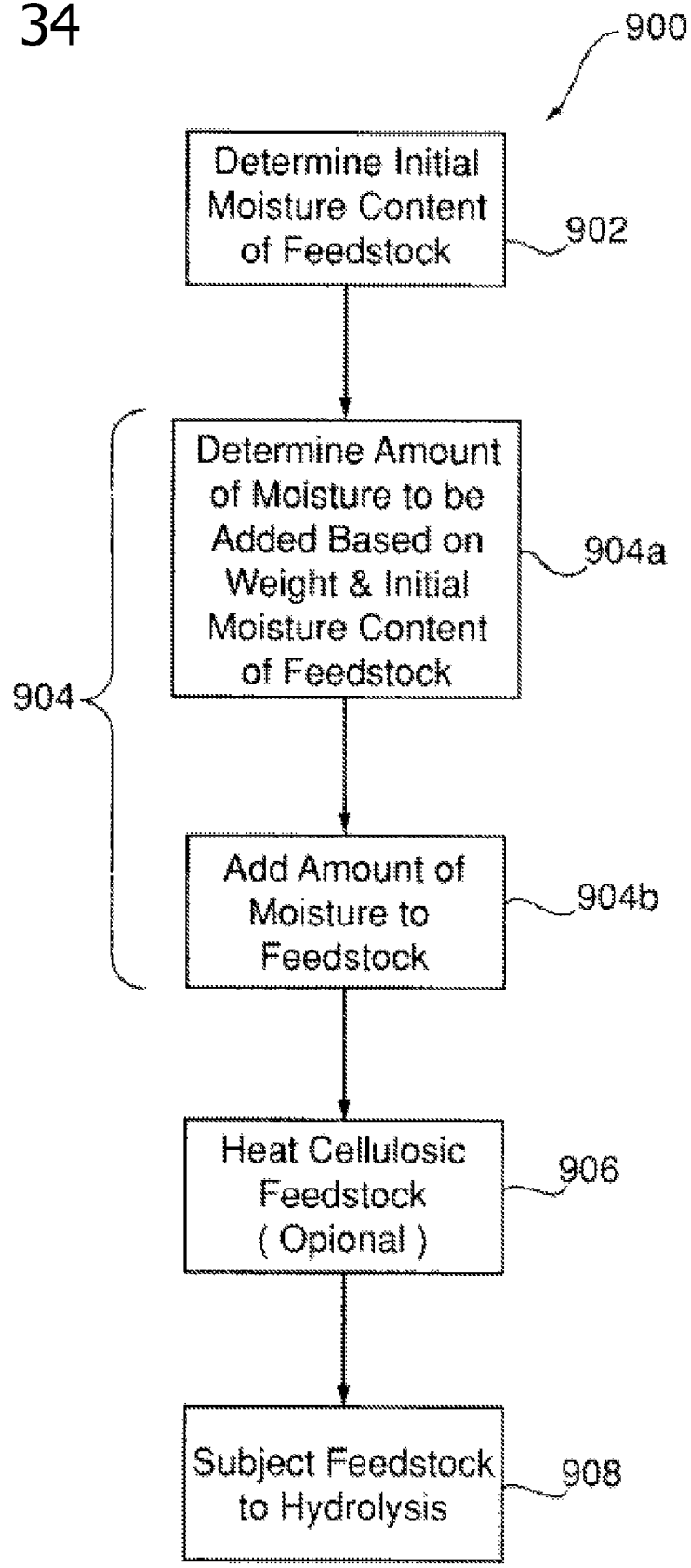
FIG. 34 is a flow chart showing steps of an embodiment of a method of the present invention.

Referring to FIG. 34, an embodiment of a method 900 for treating a cellulosic feedstock, such as for subsequent ethanol production, will presently be described. It will be appreciated that although method 900 is described with reference to apparatus 100, method 900 may be carried out with an alternate apparatus, and apparatus 100 may be used according to an alternate method. Furthermore, although method 900 is described as a continuous process, it will be appreciated that method may be carried out as a semi-continuous or batch process.

As previously mentioned, the cellulosic feedstock provided to method 900 may be varied and the initial moisture content of the cellulosic feedstock may vary depending on numerous factors. An initial moisture content of the cellulosic feedstock is determined (step 902). For example, as described previously, the cellulosic feedstock may be continuously conveyed past a moisture sensor 104. In some embodiments, wherein the cellulosic feedstock comprises straw, the initial moisture content may be less than about 15 wt % based on the total weight of the cellulosic feedstock. However, in alternate embodiments, the initial moisture content may be greater than 15 wt %.

Subsequently, an amount of moisture is added to the cellulosic feedstock to obtain a predetermined moisture content of the cellulosic feedstock (step 904). Step 904 preferably includes steps 904a and 904b. Step 904a comprises determining the amount of moisture to be added based on the weight of the cellulosic feedstock and the initial moisture content of the cellulosic feedstock. For example, once the weight of the material introduced to the process is known, and the moisture content of that material is know, the amount of water to be added may be determined by calculating the amount of water that is required to raise the moisture content of the material from the starting moisture content to the predetermined moisture content. This step may be conducted automatically by a computer, by a human operator using a calculator or a table, or any other means.

Step 904b comprises adding the required amount of moisture to the cellulosic feedstock. The moisture is preferably added at multiple locations so that the water is evenly distributed through the mass of the feedstock. Alternately, or in addition, the feedstock is preferably also mixed to assist in distributing the added moisture throughout the feedstock. For example, a mixing vessel, such as vessel 108, may be used to combine water with the feedstock and/or to mix a feedstock that has already had water added thereto. In accordance with the latter option, step 904b may comprise adding moisture to the cellulosic feedstock prior to conveying the cellulosic feedstock through a mixing vessel 108. For example, moisture may be added to the cellulosic feedstock as it is conveyed from a weighing and starting moisture determination station.

It is preferred that at least a portion of the mixing occurs without the addition of water. For example, the moisture is preferably added prior to conveying the cellulosic material through a downstream portion of mixing vessel 108, e.g., the half of vessel 108 immediately upstream of outlet 124. This permits more complete mixing of the added water and the feedstock and a greater uniformity of the moisture distribution of the feedstock at outlet 124.

Preferably, steps 902 and 904 are carried out automatically and continuously. That is, steps 902 and 904 are under preferably the control of a processor, such as processor 106, and are carried out as a continuous process, for example by conveying the cellulosic material past moisture sensor 104 on weighing conveyor 102.

In various preferred embodiments, the initial moisture content of the cellulosic feedstock (i.e., step 902) is conducted intermittently. Intermittent determination of the initial moisture content is conducted by manually sampling fractions of the incoming feedstock and determining their moisture content. Moisture is added to the cellulosic feedstock to obtain a predetermined moisture content of the cellulosic feedstock, and the feedstock is subsequently subjected to hydrolysis. Preferably in accordance with such embodiments, moisture is added to the cellulosic feedstock and the feedstock is subjected to hydrolysis automatically.

Method 900 may optionally further comprise heating the cellulosic feedstock. For example, the cellulosic feedstock may be heated while the moisture is added, by providing mixing vessel 108 with a heating jacket 140 and/or providing a heating jacket to hopper 107 and/or by heating the required water that is added to the feedstock (step 906).

The cellulosic feedstock is preferably then subjected to activation (step 908). The hydrolysis reaction is preferably conducted by autohydrolysis, which, more preferably, is followed by enzymatic hydrolysis. Autohydrolysis may be carried out directly following steps 902-906, or after any number of intermediate steps. For example, from outlet 124 of mixing vessel 108, the cellulosic feedstock may be directed to a holding tank 160 where it is stored for a period of time at an elevated temperature to further enhance the uniformity of the moisture and heat distribution, prior to being passed to an autohydrolysis reactor.

Further details regarding various embodiments of the present invention may be found in U.S. patent application Ser. Nos. 12/181,565; 12/181,596; 12/181,640; 12/181,666; 12/181,724 filed on Jul. 29, 2008 and Ser. Nos. 12/361,103 and 12/361,149 filed on Jan. 28, 2009, the entire contents of which are incorporated herein by reference.

Various methods for preparing acid-impregnated feedstocks utilizing impregnators to provide acid-impregnated feedstocks described elsewhere herein may be conducted in a manner that includes control of the moisture and/or acid introduced to the feedstock to provide an acid-impregnated feedstock having desired characteristics including those detailed elsewhere herein.

For those methods in which acid-impregnation is conducted as a batch operation, the method generally comprises determining an initial moisture content of the cellulosic feedstock. The manner of determining the initial moisture content is not narrowly critical and may be conducted manually utilizing measuring equipment known in the art (e.g., a moisture meter such as a conductivity probe). Once the initial moisture content of the feedstock is determined, the initial mass of the feedstock is determined. The initial mass of the cellulosic feedstock may be determined utilizing suitable apparatus known in the art including, for example, a weighing conveyor or a holding bin having a load sensor. After the initial moisture content is determined and a target acid loading is identified and a target moisture content is identified, an acidic liquid medium having a predetermined acid concentration is prepared. Based on the initial mass of the feedstock, an amount of the acidic liquid medium is added to the cellulosic feedstock to obtain an acid-impregnated cellulosic feedstock having a predetermined moisture content and acid content.

Preferably, the acidic liquid medium is added to the cellulosic feedstock at a substantially constant mass flow rate. To determine the appropriate time over which the acidic liquid medium is to be added to provide the acid-impregnated feedstock having the predetermined moisture content and acid content, the mass of acidic liquid medium in a holding vessel is monitored and addition of the acidic liquid medium to the cellulosic feedstock is discontinued once the desired mass of acidic liquid medium has been removed from the holding vessel. Monitoring the mass of acidic liquid medium in the holding vessel may comprise determining the mass of acidic liquid medium prior to adding acidic liquid medium to the cellulosic feedstock and determining the mass of acidic liquid medium in the holding vessel intermittently while acidic liquid medium is added to the cellulosic feedstock. Alternatively, the mass of acidic liquid medium in the holding vessel may be determined continuously while acidic liquid medium is added to the cellulosic feedstock. Preferably, contact of the acidic liquid medium and feedstock heats the feedstock. To provide a suitable acidic liquid medium, preferably the water of the acidic liquid medium is heated to a suitable temperature prior to combining with the acid to form the acidic liquid medium.

Generally, acid-impregnation in accordance with the foregoing is conducted in a suitable vessel (e.g., impregnators described elsewhere herein in connection with FIGS. 2-4). To assist in control of the temperature of the cellulosic feedstock within the vessel, preferably the vessel includes a heating jacket. Providing a vessel with a heating jacket provides for control of the temperature in the impregnator without requiring precise control of the temperature of the acidic liquid medium introduced into the vessel. Generally, the vessel or impregnator in which the acidic liquid medium is added to the cellulosic feedstock contains a plurality of introduction points along the length of the vessel and acidic liquid medium is added to the cellulosic feedstock through a plurality of the introduction points, and typically through each of the plurality of introduction points. In accordance with various preferred embodiments, the introduction points are evenly spaced along the length of the vessel.

For those embodiments in which acid-impregnation is conducted continuously, methods for controlling the acid and moisture content of the acid-impregnated feedstocks generally comprise determining an initial moisture content of the cellulosic feedstock and introducing the cellulosic feedstock into a treatment vessel (e.g., an impregnator as described in connection with FIGS. 2-4). The manner of determining the initial moisture content is not narrowly critical and may be conducted manually utilizing measuring equipment known in the art (e.g., a moisture meter such as a conductivity probe). After a target acid loading and desired final moisture content are identified and based on the initial moisture content of the feedstock, the acidic liquid medium of a desired concentration is prepared. The methods further comprise determining the mass feed rate of the cellulosic feedstock into the treatment vessel, the mass feed rate of the cellulosic feedstock preferably being provided by a weighing conveyor operated at a constant speed. The mass feed rate may also be determined by monitoring the weight loss in a weight bin feeder. Once the mass feed rate of the cellulosic feedstock into the treatment vessel is known, an acidic liquid medium is introduced into the treatment vessel at a predetermined rate to provide an acid-impregnated cellulosic feedstock having a predetermined moisture content and acid content. The predetermined mass flow rate is provided by controlling the flow rate of acidic liquid medium into the treatment vessel. The acidic liquid medium may be introduced into the treatment vessel continuously or intermittently to provide the acid-impregnated cellulosic feedstock. As with batch acid-impregnation, in various preferred embodiments the treatment vessel further comprises a heating jacket for control of temperature of the cellulosic feedstock within the treatment vessel.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

What is claimed is:

1. A method for treating a cellulosic feedstock comprising:
   a) conveying the cellulosic feedstock having a moisture content through an enclosed volume;
   b) adding moisture to the cellulosic feedstock simultaneously at multiple spaced-apart moisture injection points as the cellulosic feedstock travels through the volume to produce a moistened feedstock having a moisture content of from about 30% to about 60% by weight;
   c) heating the cellulosic feedstock as it travels through the volume and obtaining a heated moistened feedstock having a temperature of from about 50° C. to about 70° C. and having a relatively uniform temperature and moisture profile;
   d) subsequently subjecting the heated moistened feedstock to a downstream hydrolysis process in a steam explosion reactor to obtain an activated feedstock;
   e) subjecting the activated feedstock to an enzyme hydrolysis process to generate monomeric sugars; and
   g) subjecting the monomeric sugars to fermentation to generate ethanol.

2. The method of claim 1, wherein the volume comprises an impregnation chamber defined by chamber walls having an inner surface, and the impregnation chamber extends longitudinally along an axial length from an inlet to an outlet, and the cellulosic feedstock is urged through the chamber by a conveyance member.

3. The method of claim 1, wherein step (b) comprises adding moisture to increase the moisture content of the cellulosic feedstock from about 5-15 wt % to about 45-55 wt %.

4. The method of claim 2, wherein the plurality of injection points comprises a plurality of ports extending through the chamber wall commencing proximate the inlet and the method further comprising introducing moisture to the cellulosic feedstock at least during its initial travel through the impregnation chamber.

5. The method of claim 4, wherein the injection points are provided in a first third of the axial length of the impregnation chamber.

6. The method of claim 3, further comprising adding heated water as at least part of the moisture.

7. The method of claim 3, further comprising adding a catalyst with the moisture.

8. The method of claim 3, wherein step (c) comprises heating the cellulosic feedstock from less than about 30° Celsius at the inlet, to from about 50° to about 65° Celsius at the outlet.

9. The method of claim 1, wherein step (c) comprises heating the moisture prior to contacting the moisture with the feedstock.

10. The method of claim 2, wherein step (c) comprises indirectly heating the cellulosic feedstock by heating at least one of the chamber walls and the conveyance member.

11. The method of claim 2, wherein the conveyance member extends longitudinally through the impregnation chamber and is configured to urge the cellulosic feedstock axially through the impregnation chamber as the conveyance member rotates.

12. The method of claim 2, wherein the conveyance member comprises a rotary shaft extending longitudinally through the impregnation chamber and a plurality of paddles extending radially outwardly from the shaft, and the method further comprises rotating the shaft to urge the cellulosic feedstock axially through the impregnation chamber.

13. The method of claim 11, wherein the conveyance member includes moisture injection points and the method further comprises introducing moisture to the volume as the conveyance member rotates.

14. The method of claim 12, wherein the conveyance member includes a fluid conduit extending longitudinally through the shaft and a plurality of paddle ducts in communication with the fluid conduit and extending through the paddle to an outer surface thereof, and wherein the step of adding moisture to the cellulosic feedstock comprises injecting moisture into the feedstock through the paddle ducts.

15. The method of claim 2, wherein the conveyance member comprises a rotary shaft extending longitudinally through the impregnation chamber and a plurality of paddles extending radially outwardly from the shaft and the paddles are relative to the impregnation chamber to sweep at least a lower circumferential portion of the inner surface of the chamber walls when the feedstock is conveyed through the chamber.

16. The method of claim 2, wherein the conveyance member comprises a rotary shaft extending longitudinally through the impregnation chamber and a plurality of paddles extending radially outwardly from the shaft and the paddles are spaced and configured such that the lower circumferential portion of the chamber is swept along generally the entire axial length of the chamber as the feedstock is conveyed through the chamber.

17. The method of claim 1, wherein in the volume the cellulosic feedstock has a residence time of less than about ten minutes.

18. The method of claim 1, further comprising monitoring the moisture content of the cellulosic feedstock as it passes through the enclosed volume and the amount of moisture that is added is controlled to produce the heated moistened feedstock.

19. The method of claim 1, further comprising providing a feedstock having a moisture content of less than about 45 wt % comprising fibers that have a length in the range of about 4 mm to about 7 mm.

20. The method of claim 1, wherein the moisture content of the cellulosic feedstock is from about 5% to about 45% by weight.

21. A method for treating a cellulosic feedstock comprising:
   a) conveying the cellulosic feedstock having a moisture content through an enclosed volume, wherein the enclosed volume comprises (i) a shell defining a treatment chamber having a lower inner surface, the shell having an inlet and an outlet spaced longitudinally apart from the inlet to define an axial length, (ii) a conveyance member housed within the shell and configured to sweep the lower inner surface and, (iii) a plurality of injection ports provided in at least one of the shell and the conveyance member;
   b) adding moisture to the cellulosic feedstock simultaneously at multiple spaced-apart moisture injection points as the cellulosic feedstock travels through the volume to produce a moistened feedstock having a moisture content of from about 30% to about 60% by weight;
   c) heating the cellulosic feedstock as it travels through the volume and obtaining a heated moistened feedstock having a temperature of from about 50° C. to about 70° C. and having a relatively uniform temperature and moisture profile;
   d) subsequently subjecting the heated moistened feedstock to a downstream hydrolysis process in a steam explosion reactor to obtain an activated feedstock;
   e) subjecting the activated feedstock to an enzyme hydrolysis process to generate monomeric sugars; and
   g) subjecting the monomeric sugars to fermentation to generate ethanol.

22. The method of claim 21, wherein the volume comprises an impregnation chamber defined by chamber walls having an inner surface, and the impregnation chamber extends longitudinally along an axial length from an inlet to an outlet, and the cellulosic feedstock is urged through the chamber by a conveyance member.

23. The method of claim 21, wherein step (b) comprises adding moisture to increase the moisture content of the cellulosic feedstock from about 5-15 wt % to about 45-55 wt %.

24. The method of claim 15, wherein the plurality of injection points comprises a plurality of ports extending through the chamber wall commencing proximate the inlet and the method further comprising introducing moisture to the cellulosic feedstock at least during its initial travel through the impregnation chamber.

25. The method of claim 24, wherein the injection points are provided in a first third of the axial length of the impregnation chamber.

26. The method of claim 23, further comprising adding heated water as at least part of the moisture.

27. The method of claim 23, further comprising adding a catalyst with the moisture.

28. The method of claim 23, wherein step (c) comprises heating the cellulosic feedstock from less than about 30° Celsius at the inlet, to from about 50° to about 65° Celsius at the outlet.

29. The method of claim 21, wherein step (c) comprises heating the moisture prior to contacting the moisture with the feedstock.

30. The method of claim 15, wherein step (c) comprises indirectly heating the cellulosic feedstock by heating at least one of the chamber walls and the conveyance member.

31. The method of claim 15, wherein the conveyance member extends longitudinally through the impregnation chamber and is configured to urge the cellulosic feedstock axially through the impregnation chamber as the conveyance member rotates.

32. The method of claim 15, wherein the conveyance member comprises a rotary shaft extending longitudinally through the impregnation chamber and a plurality of paddles extending radially outwardly from the shaft, and the method further comprises rotating the shaft to urge the cellulosic feedstock axially through the impregnation chamber.

33. The method of claim 31, wherein the conveyance member includes moisture injection points and the method further comprises introducing moisture to the volume as the conveyance member rotates.

34. The method of claim 32, wherein the conveyance member includes a fluid conduit extending longitudinally through the shaft and a plurality of paddle ducts in communication with the fluid conduit and extending through the paddle to an outer surface thereof, and wherein the step of adding moisture to the cellulosic feedstock comprises injecting moisture into the feedstock through the paddle ducts.

35. The method of claim 15, wherein the conveyance member comprises a rotary shaft extending longitudinally through the impregnation chamber and a plurality of paddles extending radially outwardly from the shaft and the paddles are relative to the impregnation chamber to sweep at least a lower circumferential portion of the inner surface of the chamber walls when the feedstock is conveyed through the chamber.

36. The method of claim 15, wherein the conveyance member comprises a rotary shaft extending longitudinally through the impregnation chamber and a plurality of paddles extending radially outwardly from the shaft and the paddles are spaced and configured such that the lower circumferential portion of the chamber is swept along generally the entire axial length of the chamber as the feedstock is conveyed through the chamber.

37. The method of claim 21, wherein in the volume the cellulosic feedstock has a residence time of less than about ten minutes.

38. The method of claim 21, further comprising monitoring the moisture content of the cellulosic feedstock as it passes through the enclosed volume and the amount of moisture that is added is controlled to produce the heated moistened feedstock.

39. The method of claim 21, further comprising providing a feedstock having a moisture content of less than about 45 wt % comprising fibers that have a length in the range of about 4 mm to about 7 mm.

40. The method of claim 21, wherein the moisture content of the cellulosic feedstock is from about 5% to about 45% by weight.

* * * * *